(12) United States Patent
Tomoda et al.

(10) Patent No.: US 9,187,492 B2
(45) Date of Patent: Nov. 17, 2015

(54) PYRIPYROPENE DERIVATIVE HAVING ACAT2 INHIBITING ACTIVITY AND STABLE TO METABOLIZING ENZYMES

(75) Inventors: Hiroshi Tomoda, Sagamihara (JP); Tohru Nagamitsu, Sagamihara (JP); Daisuke Matsuda, Sagamihara (JP); Taichi Ohshiro, Sagamihara (JP); Masaki Ohtawa, Sagamihara (JP); Satoshi Omura, Sagamihara (JP)

(73) Assignee: School Juridical Person Kitasato Institute, Tokyo (JP)

( * ) Notice: Subject to any disclaimer, the term of this patent is extended or adjusted under 35 U.S.C. 154(b) by 195 days.

(21) Appl. No.: 13/638,332

(22) PCT Filed: Mar. 25, 2011

(86) PCT No.: PCT/JP2011/057336
§ 371 (c)(1),
(2), (4) Date: Dec. 11, 2012

(87) PCT Pub. No.: WO2011/122468
PCT Pub. Date: Oct. 6, 2011

(65) Prior Publication Data
US 2013/0085163 A1    Apr. 4, 2013

(30) Foreign Application Priority Data

Mar. 31, 2010 (JP) ................... 2010-082784

(51) Int. Cl.
*C07D 493/14* (2006.01)
*A61K 31/453* (2006.01)
*C07D 493/04* (2006.01)

(52) U.S. Cl.
CPC ............ *C07D 493/14* (2013.01); *A61K 31/453* (2013.01); *C07D 493/04* (2013.01)

(58) Field of Classification Search
CPC ......................... C07D 493/14; A61K 31/453
See application file for complete search history.

(56) References Cited

U.S. PATENT DOCUMENTS 8,519,128 B2 *  8/2013  Tomoda et al. ............... 544/310
2011/0184173 A1  7/2011  Tomoda et al.

FOREIGN PATENT DOCUMENTS

| EP | 2228376 A1 | 9/2010 |
|---|---|---|
| JP | 08269065 A | 10/1996 |
| WO | 2009081957 A1 | 7/2009 |
| WO | 2010150739 A1 | 12/2010 |

OTHER PUBLICATIONS

Tomoda et al., "Pyripyropenes, Novel ACAT Inhibitors Produced by *Aspergillus fumigatus* IV. Structure Elucidation of Pyripyropenes M to R", The Journal of Antibiotics, Mar. 1996, pp. 292-298, vol. 49, No. 3.
Ohshiro, T. et al., Selectivity of pyripyropene derivatives in inhibition toward Acyl-CoA: cholesterol acyltransferase 2, Journal of Antibiotics, 2008, pp. 503-508, vol. 61, No. 8.
Obata et al., "Structure-activity Relationships Study of Pyripyropenes: reversal of Cancer Cell Multidrug Resistance", The Journal of Antibiotics, Apr. 2000, No. 4, pp. 422-425, vol. 53.
Obata et al., "Chemical Modification and Structure-activity Relationships of Pyripyropenes 2. 1, 11-Cyclic Analogs", The Journal of Antibiotics, Nov. 1996, pp. 1149-1156, vol. 49, No. 11.
Libby, P., "The Forgotten Majority Unfinished Business in Cardiovascular Risk Reduction", J. Am. Col. Cardiol., 2005, pp. 1225-1228, vol. 46.
Meuwese, et al., "And then there were acyl coenzyme A: cholesterol acyl transferase inhibitors", Curr. Opin. Lipidol., 2006, pp. 426-431, vol. 17.
Chang, et al., "Human Acyl-CoA: Cholesterol Acyltransferase (ACAT) and its Potential as a Target for Pharmaceutical Intervention Against Atherosclerosis", Acta Biochimica et Biophysica Sinica, 2006, pp. 151-156, vol. 38, No. 3.
Farese, Jr., "The Nine Lives of ACAT Inhibitors", Arterioscler. Thromb. Vasc. Biol., 2006, pp. 1684-1686, vol. 26.
Bell, III, et al., "Dietary Fat Induced Alterations in Atherosclerosis Are Abolished by ACAT2-Deficiency in ApoB100 Only, LDLr / Mice", Arterioscler. Thromb. Vasc. Biol., 2007, pp. 1396-1402, vol. 27.

(Continued)

*Primary Examiner* — David K O Dell
(74) *Attorney, Agent, or Firm* — The Webb Law Firm

(57) ABSTRACT

A compound effective in prevention and treatment of arteriosclerosis with a mechanism different from that of statin drugs has the following formula or a pharmaceutically acceptable salt, solvate, or hydrate thereof:

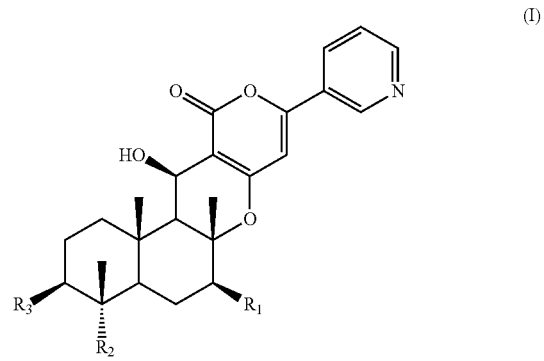

(I)

wherein $R_1$ is an aliphatic, alicyclic, or aromatic acyloxy group, or a group of the formula —O—CH($R_7$)—$R_8$ where $R_7$ is a lower alkoxy group and $R_8$ is an aryl group, and $R_2$ is carboxyl, a lower alkoxycarbonyl group, or an arylmethylcarbamoyl group, or a —$CH_2$-acyloxy group and $R_3$ is an aliphatic, alicyclic or aromatic acyloxy group, provided that at least one of $R_4$ and $R_3$ is a group other than acetoxy, or $R_2$ and $R_3$ taken together form a group of the formula —O—CH($R_5$)—O— where $R_5$ is an aryl group.

9 Claims, No Drawings

(56) References Cited

OTHER PUBLICATIONS

Tomoda, et al., "Pyripyropenes, Novel Inhibitors of Acyl-GoA: Cholesterol Acyltransferase Produced by *Aspergillus fumigatus*", Journal of Antibiotics, Feb. 1994, pp. 148-153, vol. 47, No. 2.

Lada, et al., "Identification of ACAT1- and ACAT2-specific inhibitors using a novel, cell-based fluorescence assay: individual ACAT uniqueness", Journal of Lipid Research, 2004, pp. 378-386, vol. 45.

Obata et al., "Chemical Modification and Structure-activity Relationships of Pyripyropenes, Modification at the Four Hydroxyl Groups", J. Antibiot., 1996, pp. 1133-1148, vol. 49.

Tomoda et al., "Biosynthesis of Pyripyropene A", J. Org. Chem., 1996, pp. 882-886, vol. 61.

Uelmen et al., "Tissue-specific Expression and Cholesterol Regulation of Acylcoenzyme A: Cholesterol Acyltransferase (ACAT) in Mice", J. Biol. Chem., 1995, pp. 26192-26201, vol. 270.

Bligh & Dyer, "A rapid method of total lipid extraction and purification", Can. J. Biochem. Physiol., 1959, pp. 911-917, vol. 37.

\* cited by examiner

PYRIPYROPENE DERIVATIVE HAVING ACAT2 INHIBITING ACTIVITY AND STABLE TO METABOLIZING ENZYMES

BACKGROUND OF THE INVENTION

1. Field of the Invention

The present invention relates to pyripyropene A derivatives having an extremely good inhibitory activity against cholesterol acyltransferase isozyme 2 (hereinafter abbreviated as ACAT2). More particularly, the present invention relates to pyripyropene A derivatives in which one or both of the 1- and 11-positions are substituted by an acyloxy group other than acetoxy group, the 11-position is substituted by carboxyl, an alkoxycarbonyl, or an arylcarbamoyl group, or the 1- and 11-positions are substituted by a cyclic acetal group.

2. Background Art Description of Related Art

The number of patients in Japan with hyperlipemia or arteriosclerosis which are associated with a high risk of high-mortality diseases such as myocardial infarction and cerebral apoplexy is said to be as many as thirty million, including subjects having no subjective symptoms. Even at the present time when the Guidelines for Prevention of Atherosclerotic Cardiovascular Diseases have been revised by the Japan Atherosclerosis Society, death due to these diseases ranks high among the causes of death in Japan. Hyperlipemia and arteriosclerosis are significant health problems not only in Japan but also in Europe and the Americas.

The drugs which are most widely used at present for prevention and treatment of arteriosclerosis are statin drugs which specifically inhibit hydroxy-3-methylglutaryl coenzyme A (hereinafter abbreviated as HMG-CoA) reductase. Statin drugs have been the most widely sold drugs in the world for 8 consecutive years from 2001. They are widely used, as demonstrated by the fact that two statin drugs ranked in the top thirty drugs having the highest worldwide sales in 2008. However, in actuality, it has been found that these drugs exhibit an effect on prevention of onset in only 30%-40% of patients and produce no suppression of cardiovascular diseases or the like in about half of patients who received therapy with such a drug (Non-Patent Document 1).

The reasons why HMG-CoA reductase inhibitors which are currently used as prophylactic or therapeutic agents for arteriosclerosis cannot sufficiently suppress cardiovascular diseases or similar diseases are thought to relate to the fact that the mechanism of onset of arteriosclerosis is complicated, the onset mostly being caused by heredity, diabetes, drugs, and other various factors acting in combination. Therefore, diagnosis and treatment of these diseases need to be based on the pathological conditions of each patient.

Accordingly, there is an urgent desire for the development of a drug having a new mechanism of activities which can be expected to have an effect on suppression of onset of disorders in the coronary artery or degeneration of lesions in the coronary artery and which is different from the mechanism of statin drugs. However, there has been almost no progress in development of a drug as a substitute for statin drugs.

Cholesterol acyltransferase (hereinafter abbreviated as ACAT) is an enzyme which catalyzes the introduction of an acyl group into cholesterol, and it is considered to be a target of drugs which are expected to be developed for treatment of statin-resistant arteriosclerosis or tailor-made treatment in accordance with individual pathological conditions. This enzyme has attracted attention for years as an important target molecule of a drug for prevention and treatment of arteriosclerosis, and a number of synthetic ACAT inhibitors have been developed. However, these inhibitors have not yet been put to clinical use due to side effects or insufficient effects (Non-Patent Document 2).

It has recently been revealed that ACAT exists in the form of two isozymes, ACAT1 and ACAT2, which have different in vivo functions and different locations from each other (Non-Patent Document 3). ACAT1 is widely found in many living cells and tissues and is highly expressed particularly in macrofages and smooth muscle cells. It takes part in arteriosclerosis by causing the formation of foam macrofage cells, which are a cause of arteriosclerosis. ACAT2 is expressed specifically in the small intestine and liver and is thought to take part in the absorption of dietary cholesterol and the secretion of very low-density lipoproteins in each of these organs. As the difference between ACAT1 and ACAT2 with respect to in vivo functions becomes clear, the importance of specifying its selectivity has been recognized in the development of new drugs targeted at ACAT.

It has been found that synthetic ACAT inhibitors, the development of which has been abandoned, have an activity which selectively inhibits ACAT1 (such as Wu-V-23) or which inhibits both ACAT1 and ACAT2 (such as avasimibe and pactimibe) (Non-Patent Document 4).

Taking the recently reported results of knockout mice (Non-Patent Document 5) into consideration, there is a strong expectation that a new drug will be developed from the family of selective ACAT2 inhibitors. It is reported that pyripyropene A having the formula shown below (Non-Patent Document 6) is a selective ACAT2 inhibitor (Non-Patent Document 7). However, up to the present time, there has been no research aimed at development of a new drug which is a selective ACAT2 inhibitor.

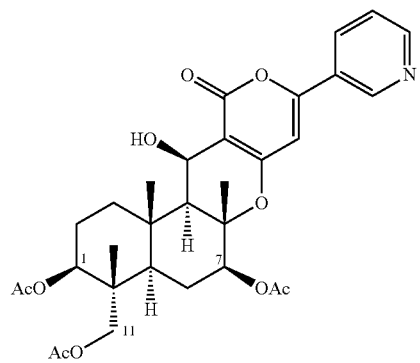

Pyripyropene A

It is disclosed in Patent Document 1 that pyripyropene derivatives in which the 1-, 7- and/or 11-positions of pyripyropene A are substituted by certain groups have an ACAT2-inhibiting activity. However, it is not disclosed or suggested in that document that ACAT2 inhibition is achieved without decomposition by metabolizing enzymes.

Non-Patent Document 1: Libby, J. Am. Col. Cardiol., Vol. 46, pp. 1225-1228, 2005;

Non-Patent Document 2: Meuwese et al., Cull. Opin. Lipidol., Vol. 17, pp. 426-431, 2006;

Non-Patent Document 3: Chang et al., Acta. Biochim. Biophys. Sin., vol. 38, pp. 151-156, 2006;

Non-Patent Document 4: Farese, Arterioscler. Thromb. Vasc. Biol., vol. 26, pp. 1684-1686, 2006;

Non-Patent Document 5: Bell et al., Arterioscler. Thromb. Vasc. Biol., vol. 27, pp. 1396-1402, 2007;

Non-Patent Document 6: Tomoda et al., J. Antibiot. Vol. 47, pp. 148-153, 1994;
Non-Patent Document 7: Lada et al., J. Lipid Res., vol. 45, pp. 378-386, 2004;
Patent Document 1: WO 2009/081957.

SUMMARY OF THE INVENTION

It is an object of the present invention to provide a compound which is effective as a prophylactic or therapeutic agent for arteriosclerosis with a mechanism which is different from that of statin drugs.

Another object of the present invention is to provide a compound which is useful as an effective prophylactic or therapeutic agent for arteriosclerosis by having a selective ACAT2-inhibiting ability and exhibiting a high activity without decomposition by metabolizing enzymes.

The present inventors found that certain novel pyripyropene derivatives are not susceptible to hydrolysis with a metabolizing enzyme and have an extremely high inhibitory activity against ACAT2, which has drawn attention as a target of a drug for prevention and treatment of arteriosclerosis, and they thereby accomplished the present invention.

The present invention is a compound having the following general formula (I) and a pharmaceutically acceptable salt, solvate, and hydrate thereof:

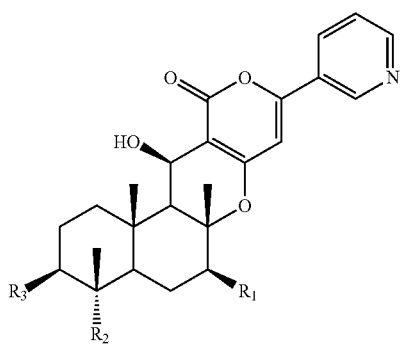

(I)

wherein
$R_1$ is an aliphatic, alicyclic or aromatic acyloxy group which may be substituted, or a group of the formula —O—CH($R_7$)—$R_8$ where $R_7$ is a lower alkoxy group and $R_8$ is an aryl group which may be substituted, and
$R_2$ and $R_3$ are either of the following:
$R_2$ is carboxyl, a lower alkoxycarbonyl group, or an arylmethylcarbamoyl group which may be substituted on its aromatic ring, or a group of the formula —CH$_2$—$R_4$— where $R_4$ is an aliphatic, alicyclic or aromatic acyloxy group which may be substituted, and $R_3$ is an aliphatic, alicyclic or aromatic acyloxy group which may be substituted, provided that at least one of $R_4$ and $R_3$ is a group other than acetoxy, or
$R_2$ and $R_3$ taken together form a group of the formula —O—CH($R_5$)—O— where $R_5$ is an aryl group which may be substituted.

In the description of the present invention, the aliphatic acyloxy group is preferably a lower alkyl carbonyloxy group. The term "lower alkyl" used herein means a straight- or branched-chain alkyl group having 1 to 6 carbon atoms and preferably 1 to 4 carbon atoms. Similarly, the term "lower alkoxy" means a straight- or branched-chain alkoxy group having 1 to 6 carbon atoms and preferably 1 to 4 carbon atoms.

Examples of a "lower alkylcarbonyloxy" include acetoxy, n-propionyloxy, propionyloxy, n-butyryloxy, i-butyryloxy, s-butyryloxy, t-butyryloxy, n-valeryloxy, neovaleryloxy, i-valeryloxy, t-valeryloxy, n-caproyloxy, and i-caproyloxy. A hydrogen atom on the lower alkylcarbonyloxy may be substituted by a substituent. Examples of the substituent include a halogen (F, Cl, Br or I), nitro, cyano, an amino group (including a mono- and di-(lower alkyl)amino), and a lower alkoxy.

The term "alicyclic acyloxy group" means a cycloalkylcarbonyloxy group having 4-7 ring carbon atoms. Specific examples include cyclopentylcarbonyloxy and cyclohexylcarbonyloxy. A hydrogen atom on the carbocyclic ring may be substituted by a substituent as exemplified above.

The term "aromatic acyloxy group" means an arylcarbonyloxy group. Examples of "aryl" include phenyl and naphthyl groups. Therefore, examples of the aromatic acyloxy group include benzoyloxy and naphthoyloxy groups.

The term "arylmethylcarbamoyl" means a group of the formula —CONH—CH$_2$-aryl wherein the aryl group may be a substituted aryl such as a substituted phenyl.

"Aryl" may be a substituted aryl group having one or more substituents on the aromatic ring. Examples of a substituent on an aromatic ring include a lower alkyl, a lower alkoxy, a halogen (F, Cl, Br or I), nitro, cyano, and an amino group (including a mono- and di-(lower alkyl)amino).

Specific examples of a substituted aryl for $R_5$ include o-methylphenyl, p-methoxyphenyl, o,o-dimethylphenyl, and o-fluorophenyl. Examples of a substituted aryl in an arylcarbonyloxy having a substituted aryl include p-cyanophenyl, p-nitrophenyl, and p-fluorophenyl. An example of a substituted aryl in an arylmethylcarbamoyl having a substituted aryl includes o,o-dimethoxyphenyl.

Pyripyropene derivatives according to the present invention are novel compounds which can be easily prepared, and they can selectively inhibit ACAT2 with their inhibitory activity being sustained in the living body due to their lack of susceptibility to hydrolysis by metabolizing enzymes. Therefore, these compounds are useful as drugs which are effective for prevention or treatment of arteriosclerosis.

DETAILED DESCRIPTION OF THE INVENTION

A compound of the above formula (I) according to the present invention encompasses compounds of the following formulas (II), (III), and (IV).

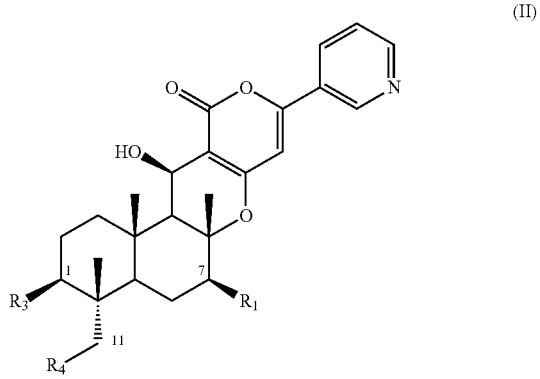

(II)

wherein $R_1$, $R_3$, and $R_4$ each represent a group selected from a lower alkylcarbonyloxy, a substituted or unsubstituted arylcarbonyloxy and preferably a substituted or unsubstituted benzoyloxy, and a cycloalkylcarbonyloxy, and wherein all or any two of $R_1$, $R_3$, and $R_4$ may be the same group with the exception that both $R_3$ and $R_4$ cannot be an acyloxy.

(III)

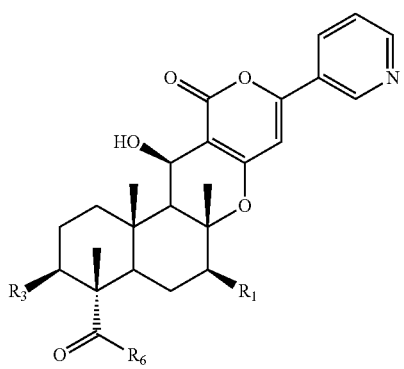

wherein $R_6$ is a hydroxyl group (OH), a lower alkoxy group or benzylamino or more generally an arylmehtylamino group which may be substituted on the aromatic ring, and $R_1$ and $R_3$ may be the same or different and each represent a group selected from a lower alkylcarbonyloxy, a substituted or unsubstituted arylcarbonyloxy, and a cycloalkylcarbonyloxy.

(IV)

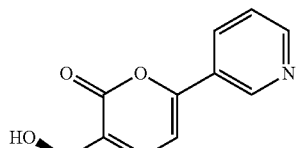

wherein $R_5$ is an aryl group which may be substituted, $R_1$ is a group selected from a lower alkylcarbonyloxy, a substituted or unsubstituted arylcarbonyloxy, and a cycloalkylcarbonyloxy or a group of the formula —O—CH($R_7$)—$R_8$ where $R_7$ is a lower alkoxy group and $R_8$ is an aryl group and preferably phenyl which may be substituted. Examples of a substituted phenyl for $R_8$ include o-methylphenyl, p-methoxyphenyl, o,o-dimethylphenyl, and o-fluorophenyl.

A compound of the above Formula (II) in which $R_1$ is an arylcarbamoyloxy group (e.g, benzoyloxy), $R_4$ is acetoxy, and $R_3$ is benzoyloxy can be prepared in accordance with the following scheme.

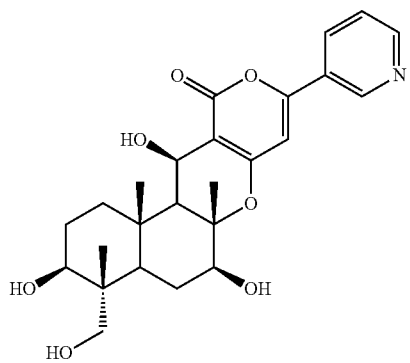

(a)

$\xrightarrow{(tBu)_2Si(OTf)_2}$

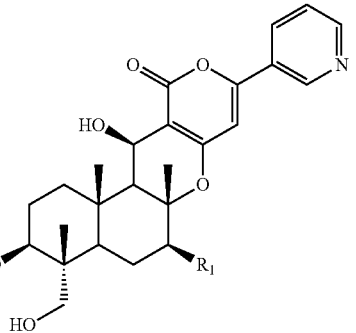

(b)

$\xrightarrow[\text{DMAP}]{\text{R*CO}_2\text{H condensation agent}}$ (c)

$\xrightarrow{\text{NH}_4\text{F}}$ (d)

$\xrightarrow[\text{DMAP}]{\text{Ac}_2\text{O, Et}_3\text{N}}$

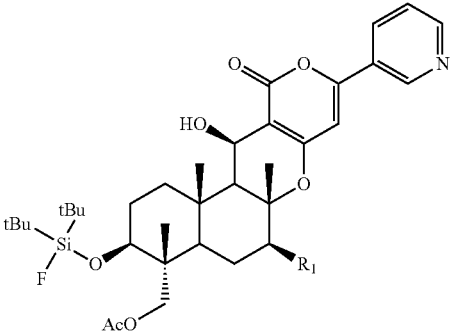

(e)

$\xrightarrow{\text{Et}_3\text{N·3HF}}$

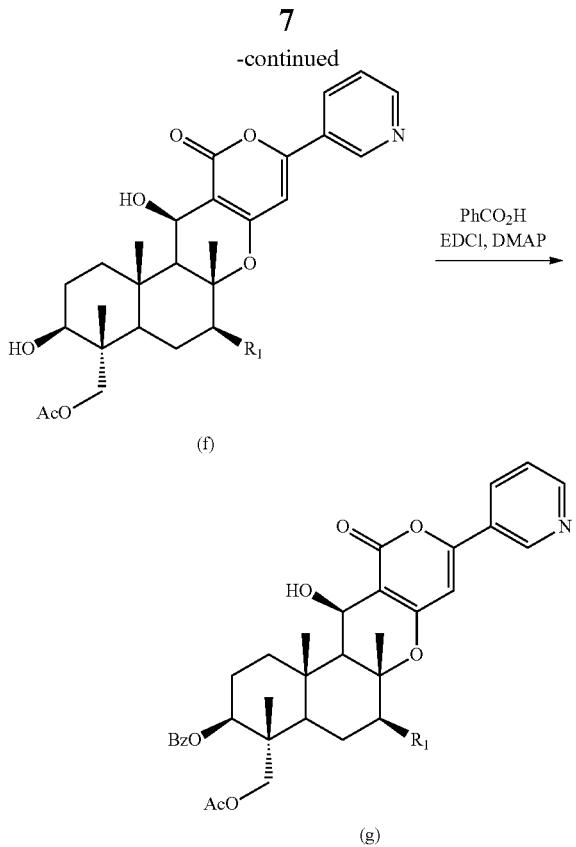

In the above scheme, R*CO₂H indicates the aromatic carboxylic acid such as benzoic acid which corresponds to the arylcarbonyloxy group $R_1$.

Compound (a) in the above scheme can be prepared in a conventional manner (see Obata et al., J. Antibiot., Vol. 49, pp. 1133-1148, 1996, for example).

The conversion of compound (a) into compound (b) can be carried out in the following manner Compound (a) is reacted with 1.2 equivalents of di-tert-butylsily-ditrifluoromethane sulfonate or di-tert-butylsilyl dichloride in the presence of 2.4 equivalents or more of an organic amine (preferably 2,6-lutidine) in dimethylformamide (solvent) for 1 h with ice cooling. The reaction mixture is subjected to conventional post-treatment to obtain compound (b).

The conversion of compound (b) into compound (c) can be carried out in the following manner Compound (b) is reacted for from 30 min to 2 days at room temperature in a solvent such as dichloromethane, dimethylformamide, tetrahydrofuran, acetonitrile or a mixture of these in the presence of 1 equivalent or more of the corresponding carboxylic acid R*CO₂H, 1 equivalent or more of a condensation agent (preferably 1-ethyl-3-(3-dimethylaminopropyl)carbodiimide hydrochloride or dicyclohexylcarbodiimide), and 0.5 equivalents or more of an organic base (preferably N,N-dimethylaminopyridine). The reaction mixture is subjected to conventional post-treatment to give compound (c).

The conversion of compound (c) into compound (d) can be carried out in the following manner Compound (c) is reacted for 3-5 h at room temperature in a solvent such as an alcohol (preferably methanol or ethanol) or tetrahydrofuran or acetonitrile or a mixture of these in the presence of 10 equivalents or more of ammonium fluoride. The reaction mixture is subjected to conventional post-treatment to give compound (d) as a primary product.

The conversion of compound (d) into compound (e) can be carried out in the following manner Compound (d) is reacted for from 30 min to 2 days at 0° C. or room temperature in a solvent such as dichloromethane, dimethylformamide, tetrahydrofuran, acetonitrile or a mixture of these in the presence of 1 equivalent or more of acetic anhydride, 1.5 equivalents or more of an organic amine (preferably triethylamine or diisopropylethylamine), and 0.5 equivalents or more of an organic base (preferably dimethylaminopyridine). The reaction mixture is subjected to conventional post-treatment to give compound (e).

In the above scheme, $R_4$ is depicted as acetoxy, but any acyloxy group other than acetoxy can be introduced as $R_4$ by replacing acetic anhydride by the corresponding acid anhydride when compound (d) is converted into compound (e).

The conversion of compound (e) into compound (f) can be carried out in the following manner Compound (e) is reacted for 1 h at room temperature in a solvent such as tetrahydrofuran, an alcohol (preferably methanol or ethanol) or acetonitrile or a mixture of these in the presence of 1 equivalent or more of a fluorine reagent (preferably triethylamine trihydrofluoride or tetrabutylammonium fluoride). The reaction mixture is subjected to conventional post-treatment to give compound (f).

The conversion of compound (f) into compound (g) can be carried out in the following manner. Compound (f) is reacted for from 30 min to 2 days at room temperature in a solvent such as dichloromethane, dimethylformamide, tetrahydrofuran, acetonitrile or a mixture of these in the presence of 1 equivalent or more of benzoic acid, 1 equivalent or more of a condensation agent (preferably 1-ethyl-3-(3-dimethylaminopropyl)carbodiimide hydrochloride or dicyclohexylcarbodiimide), and 0.5 equivalents or more of an organic base (preferably dimethylaminopyridine). The reaction mixture is subjected to conventional post-treatment to give compound (g).

In the above scheme, $R_3$ is depicted as benzoyloxy, but any arylcarbonyloxy group other than benzoyloxy can be introduced as $R_3$ by replacing benzoic acid by the corresponding aryl carboxylic acid (e.g., a substituted benzoic acid) when compound (f) is converted into compound (g). It is also possible to prepare a compound in which $R_3$ is an aliphatic acyloxy group, e.g., a lower alkylcarbonyloxy group such as acetoxy or an alicyclic acyloxy group, e.g., a cycloalkylcarbonyloxy group by using an aliphatic or alicyclic carboxylic acid (e.g., acetic acid or cyclohexylcarboxylic acid) in place of benzoic acid.

A compound of the above Formula (III) in which $R_6$ is 2,4-dimethoxybenzylamino and $R_3$ is acetoxy can be prepared in accordance with the following scheme starting from compound (d) shown in the above scheme.

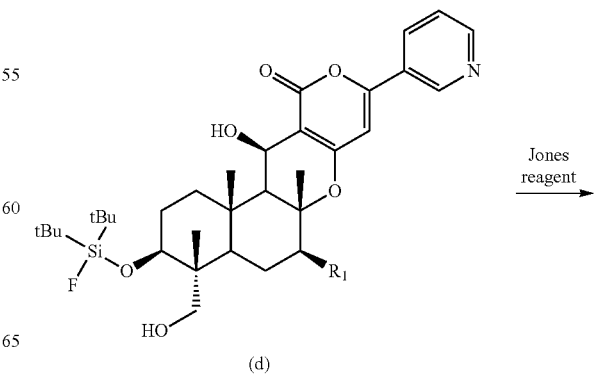

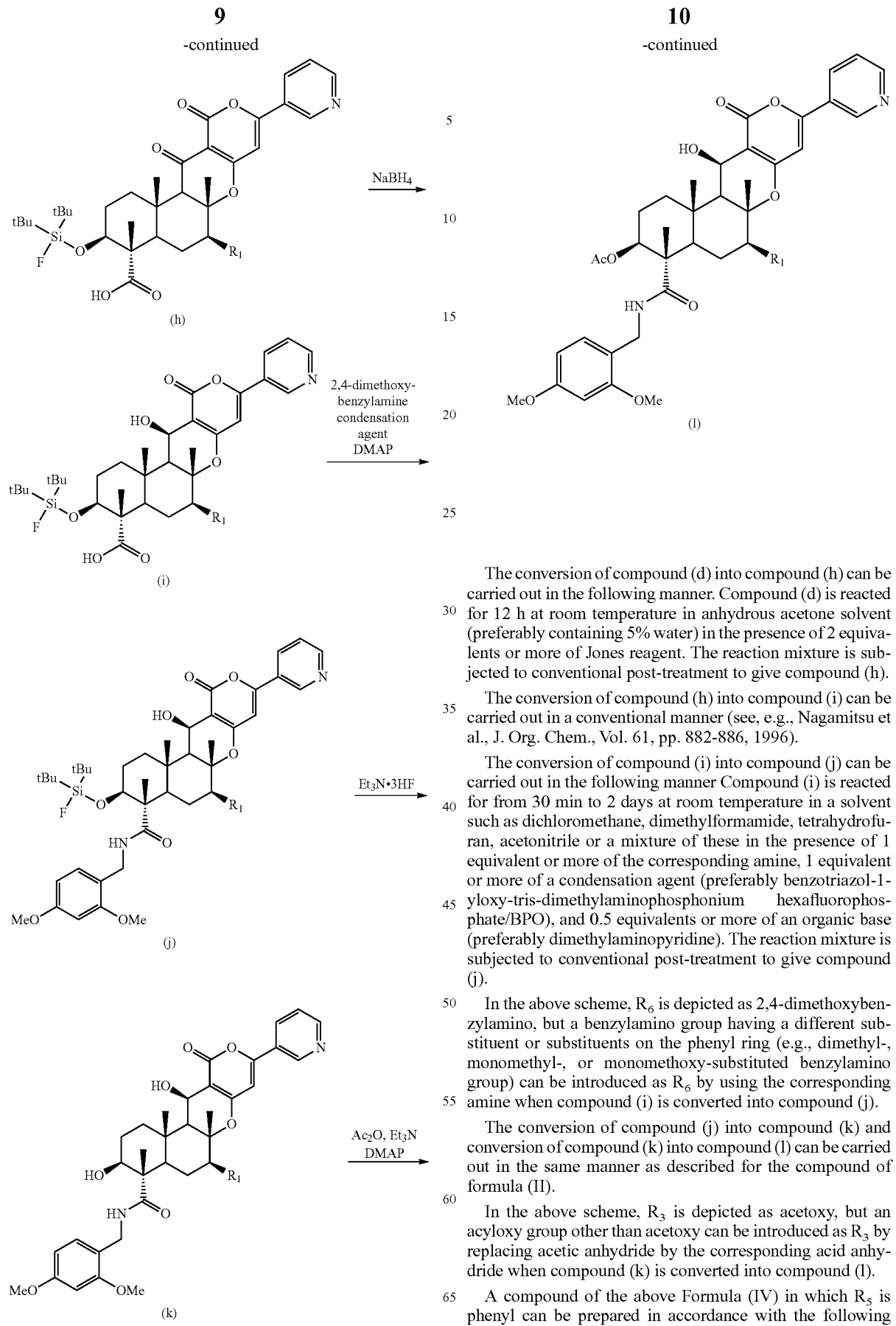

The conversion of compound (d) into compound (h) can be carried out in the following manner. Compound (d) is reacted for 12 h at room temperature in anhydrous acetone solvent (preferably containing 5% water) in the presence of 2 equivalents or more of Jones reagent. The reaction mixture is subjected to conventional post-treatment to give compound (h).

The conversion of compound (h) into compound (i) can be carried out in a conventional manner (see, e.g., Nagamitsu et al., J. Org. Chem., Vol. 61, pp. 882-886, 1996).

The conversion of compound (i) into compound (j) can be carried out in the following manner Compound (i) is reacted for from 30 min to 2 days at room temperature in a solvent such as dichloromethane, dimethylformamide, tetrahydrofuran, acetonitrile or a mixture of these in the presence of 1 equivalent or more of the corresponding amine, 1 equivalent or more of a condensation agent (preferably benzotriazol-1-yloxy-tris-dimethylaminophosphonium hexafluorophosphate/BPO), and 0.5 equivalents or more of an organic base (preferably dimethylaminopyridine). The reaction mixture is subjected to conventional post-treatment to give compound (j).

In the above scheme, $R_6$ is depicted as 2,4-dimethoxybenzylamino, but a benzylamino group having a different substituent or substituents on the phenyl ring (e.g., dimethyl-, monomethyl-, or monomethoxy-substituted benzylamino group) can be introduced as $R_6$ by using the corresponding amine when compound (i) is converted into compound (j).

The conversion of compound (j) into compound (k) and conversion of compound (k) into compound (l) can be carried out in the same manner as described for the compound of formula (II).

In the above scheme, $R_3$ is depicted as acetoxy, but an acyloxy group other than acetoxy can be introduced as $R_3$ by replacing acetic anhydride by the corresponding acid anhydride when compound (k) is converted into compound (l).

A compound of the above Formula (IV) in which $R_5$ is phenyl can be prepared in accordance with the following scheme.

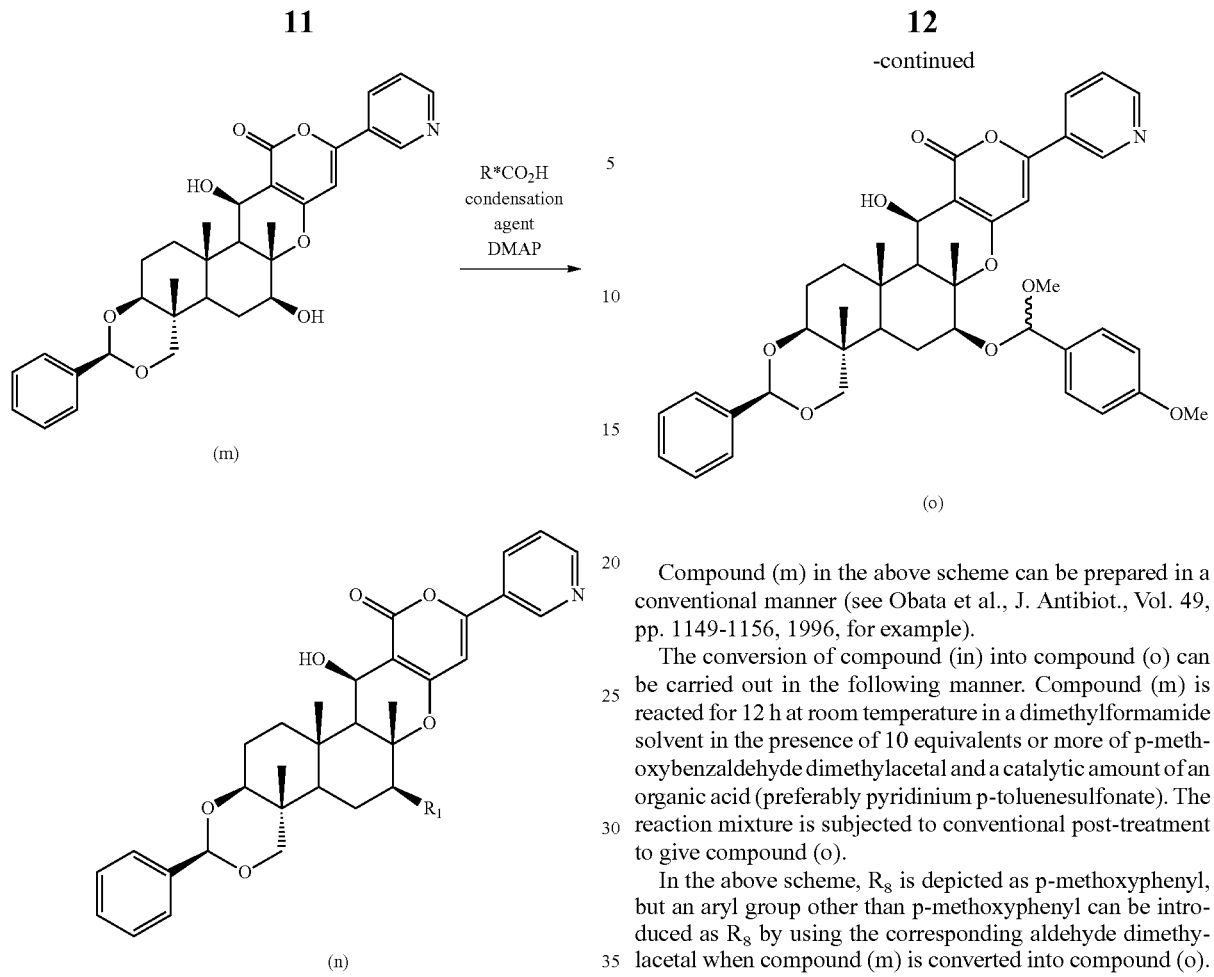

In the above scheme, R*CO₂H indicates the carboxylic acid corresponding to R₁.

Compound (m) in the above scheme can be prepared in a conventional manner (see Obata et al., J. Antibiot., Vol. 49, pp. 1149-1156, 1996, for example).

The conversion of compound (m) into compound (n) can be carried out in the same manner as described for the compound of formula (II).

A compound of the above Formula (IV) in which R₁ is a group of the formula —O—CH(R₇)—R₈ where R₇ is methoxy and R₈ is p-methoxyphenyl and R₅ is phenyl can be prepared in accordance with the following scheme.

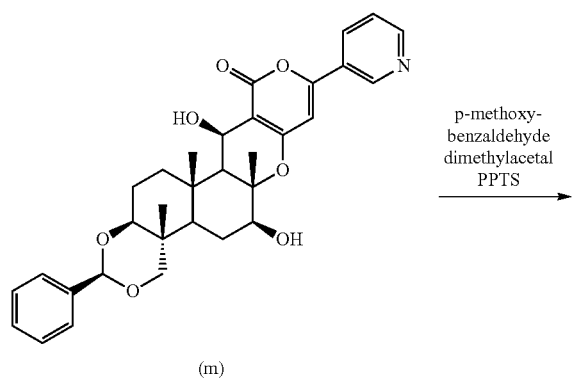

Compound (m) in the above scheme can be prepared in a conventional manner (see Obata et al., J. Antibiot., Vol. 49, pp. 1149-1156, 1996, for example).

The conversion of compound (m) into compound (o) can be carried out in the following manner. Compound (m) is reacted for 12 h at room temperature in a dimethylformamide solvent in the presence of 10 equivalents or more of p-methoxybenzaldehyde dimethylacetal and a catalytic amount of an organic acid (preferably pyridinium p-toluenesulfonate). The reaction mixture is subjected to conventional post-treatment to give compound (o).

In the above scheme, R₈ is depicted as p-methoxyphenyl, but an aryl group other than p-methoxyphenyl can be introduced as R₈ by using the corresponding aldehyde dimethylacetal when compound (m) is converted into compound (o).

A compound according to the present invention has a high inhibitory activity against ACAT2. Therefore, a compound according to the present invention can be used for prevention and treatment of arteriosclerosis in animals including human beings.

The present invention also provides an ACAT2 inhibitor comprising as an active ingredient the above-described compound or a pharmaceutically acceptable salt, solvate, or hydrate thereof, and a pharmaceutical composition for ACAT2 inhibition comprising the above-described compound or a pharmaceutically acceptable salt, solvate, or hydrate thereof and a pharmaceutically acceptable carrier.

The pharmaceutical composition according to the present invention can be formulated by any method known to those skilled in the art. For example, a compound according to the present invention may be combined with a pharmaceutically acceptable carrier such as one or more ingredients selected from sterilized water, physiological saline, vegetable oils, emulsifiers, suspending agents, surfactants, stabilizers, flavors, excipients, vehicles, preservatives, binders, and the like and mixed to form a composition in a unit dosage form which is required for generally accepted pharmaceutical practice.

For oral administration, a compound according to the present invention or its salt can be formulated in the form of a tablet, pill, sugar-coated tablet, capsule, liquid, gel, syrup, slurry, suspension, powder, or the like by mixing it with a pharmaceutically acceptable carrier which is well known in the art.

Any carrier which has heretofore been known in the art can be widely used. Examples of such a carrier include excipients such as lactose, sucrose, sodium chloride, glucose, urea, starch, calcium carbonate, kaolin, crystalline cellulose, and silica; binders such as water, ethanol, propanol, simple syrup, glucose solution, starch solution, gelatine solution, carboxymethylcellulose, shellac, methylcellulose, potassium phosphate, and polyvinylpyrrolidone; disintegrating agents such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose; disintegration suppressors such as sucrose, stearin cacao butter, and hydrogenated oils; absorbefacients such as quaternary ammonium salts and sodium lauryl sulfate; humectants such as glycerin and starch; adsorbents such as starch, lactose, kaolin, bentonite, and colloidal silica; lubricants such as purified talc, stearic acid salts, boric acid powder, and polyethylene glycol; and the like. In addition, tablets may be in the form of tablets having a conventional coating, such as sugar-coated tablets, gelatine-encapsulated tablets, enteric-coated tablets, film-coated tablets, or multi-coated tablets with two or more coating layers.

For parenteral administration, a compound according to the present invention or its salt can be formulated in accordance with a conventional formulating practice using a pharmaceutically acceptable vehicle which is well known in the art as a carrier. Examples of a water-soluble vehicle for use in injections include physiological saline and isotonic solutions containing glucose or other adjuvant such as D-sorbitol, D-mannose, D-mannitol, or sodium chloride. They may be used along with a suitable solubilizer, for example, an alcohol such as ethanol, a polyhydric alcohol such as propylene glycol or polyethylene glycol, or a nonionic surfactant such as polysolvate 80™ or HCO-50. An oily vehicle includes sesame oil and soybean oil, and it may be used along with a solubilizer such as benzyl benzoate or benzyl alcohol. In addition, a buffer such as a phosphate buffer solution or a sodium acetate buffer solution, a soothing agent such as procaine hydrochloride, a stabilizer such as benzyl alcohol or phenol, and an antioxidant may be added. An injection which was prepared is usually packaged in appropriate ampoules.

An appropriate route of administration of a pharmaceutical composition according to the present invention includes but is not limited to oral, intrarectal, mucosal, or intraintestinal administration and intramuscular, subcutaneous, intramedullary, intrathecal, direct intraventricular, intravenous, intravitreous, intraperitoneal, intranasal, or intraocular injection. The route of administration can be appropriately selected depending on the patient's age, condition, and other medicines which are also administered to the patient.

The dose of a pharmaceutical composition according to the present invention in each administration can be selected in the range from 0.001 mg to 10 mg per kg of body weight. Alternatively, the dose in each administration can be selected in the range from 0.1 mg to 100 mg. The dose is not necessarily limited to these ranges. Administration can be carried out once or multiple times a day, or it may be carried out once in a plurality of days. The dose and dosage regimen can be suitably selected by the accompanying medical practitioner in view of the body weight, age, and condition of a patient, and other medicines which are also administered to the patient.

A compound according to the present invention has an improved ACAT2-inhibiting activity and is useful as a therapeutic or prophylactic agent for obesity, adiposis, hyperlipidemia, hypercholesterolemia, disorder of lipid metabolism, arteriosclerosis, or hypertension. In addition, a pharmaceutical composition containing a compound according to the present invention or its pharmacologically acceptable salt, its pharmacologically acceptable ester, or other pharmacologically acceptable derivative thereof as an active ingredient is useful as a prophylactic or therapeutic drug for diseases relating to arteriosclerosis.

EXAMPLES

The following examples and preparations are intended to illustrate the present invention, but the present invention is not limited thereto.

Example 1

7-O-p-cyanobenzoyl-1,7-dideacetyl-1-O-isobutyrylpyripyropene A (PRD 119)

a) Preparation of 1,11-O-(di-tert-butylsilylene)-1,7,11-trideacetylpyripyropene A (b)

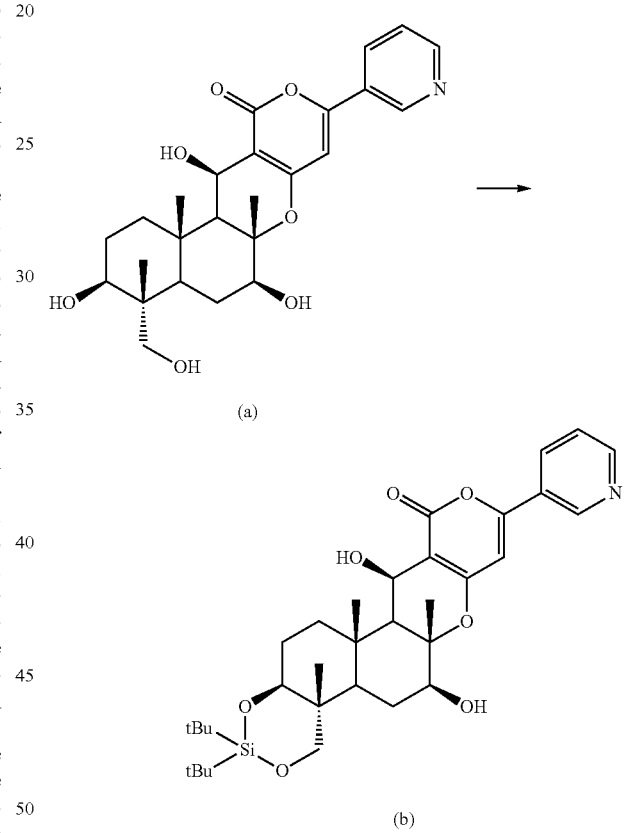

In an argon atmosphere, 2,6-lutidine (103 mL, 0.88 mmol) and $^tBu_2Si(OTf)_2$ (161 ml, 0.44 mmol) were added to a solution in dried DMF (4 mL) of a (168 mg, 0.367 mmol) prepared by the method of Obata et al., (J. Antibiot., vol. 49, pp. 1149-1156, 1996) and stirred for 0.5 h at 0° C. MeOH was added to terminate the reaction. EtOAc was added to the reaction mixture, and the organic layer was washed with 1N HCl and water and dried over anhydrous sodium sulfate. The solution was filtered, and the filtrate was dried onver anhydrous sodium sulfate and concentrated in vacuo. The resulting residue was purified by neutral flash silica gel column chromatography (3×10, MeOH in $CH_2Cl_2$ 0-3%) to give b (220 mg, quantitative) as a white foam.

$^1$H NMR (CDCl$_3$, 300 MHz) δ8.99 (d, 1H, H-2", J=2.4 Hz), 8.68 (dd, 1H, H-6", J=1.5, 4.8 Hz), 8.13-8.09 (m, 1H,

H-4"), 7.44-7.40 (m, 1H, H-5"), 6.50 (s, 1H, H-5'), 5.31 (t, 1H, H-13, J=3.0 Hz), 3.93-3.73 (m, 4H, H-1, 7, 11), 3.26 (br s, 1H, OH-13), 2.85 (br s, 1H, OH-7), 2.18-1.26 (m, 8H, H-2, 3, 5, 8, 9), 1.66 (s, 3H, Me), 1.40 (s, 3H, Me), 1.14 (s, 3H, Me), 1.09 (s, 9H, $^t$Bu), 1.05 (s, 911, $^t$Bu).

FAB-LRMS m/z 727 (MH$^+$); FAB-HRMS (m-NBA) calcd. for C$_{41}$H$_{50}$N$_2$O$_8$Si 727.3415 (MH$^+$), found 727.3428 (MH$^+$).

c) Preparation of 7-O-p-cyanobenzoyl-1-(fluoro-di-tert-butylsilyl)-1,7,11-trideacetylpyripyropene A (q)

b) Preparation of 7-O-p-cyanobenzoyl-1,11-O-(di-tert-butylsilylene)-1,7,11-trideacetylpyripyropene A (p)

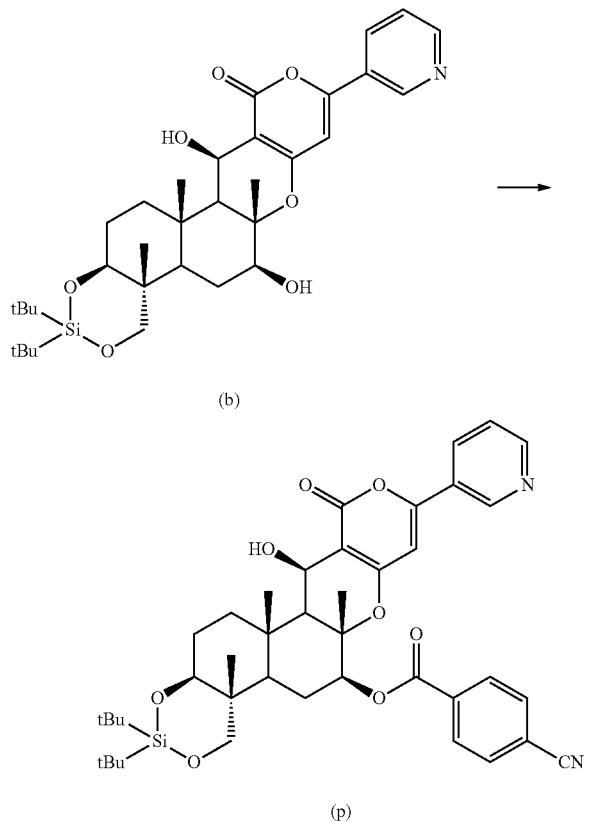

(b)

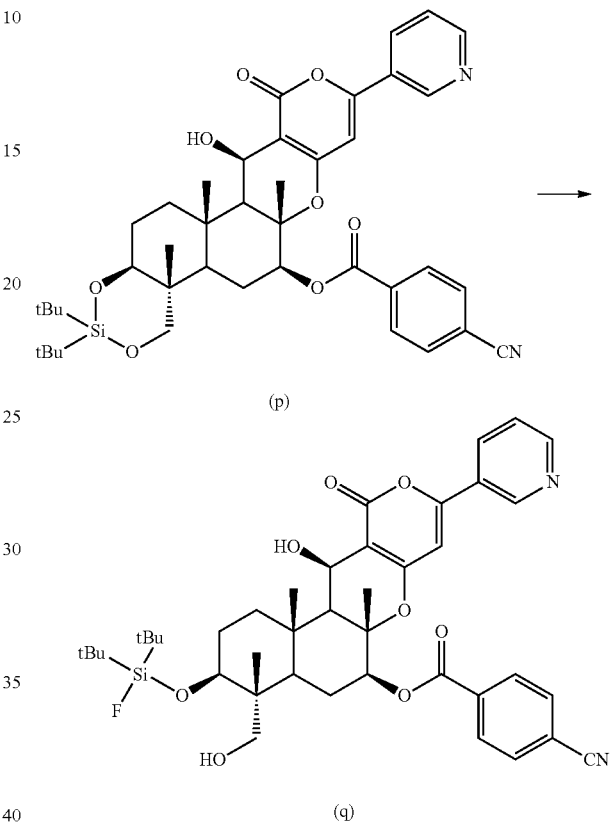

(p)

(p)

(q)

In a nitrogen atmosphere, p-cyanobenzoic acid (89.0 mg, 0.611 mmol), EDCI (146 mg, 0.764 mmol), and DMAP (62.0 mg, 509 μmol) were added to a solution of b (304 mg, 509 μmol) in CH$_2$Cl$_2$ (6.0 mL) and stirred for 1 h at room temperature. MeOH was added to the reaction mixture to terminate the reaction. The reaction mixture was diluted with EtOAc, and the organic layer was washed with water and dried over anhydrous sodium sulfate. The resulting residue was purified by neutral flash silica gel column chromatography (3.5×10, MeOH in CH$_2$Cl$_2$ 0-1.5%) to give p (348 mg, 94%) as a white foam.

$^1$H NMR (CDCl$_3$, 300 MHz) δ8.97 (dd, 1H, H-2", J=0.6, 1.5 Hz), 8.67 (dd, 1H, H-6", J=1.8, 4.8 Hz), 8.22 (d, 2H, H—Ar, J=8.4 Hz), 8.09-8.05 (m, 1H, H-4"), 7.81 (d, 2H, H—Ar, J=8.4 Hz), 7.41-7.29 (m, 1H, H-5"), 6.40 (s, 1H, H-5'), 5.28-5.25 (m, 1H, H-7), 5.03 (d, 1H, H-13, J=4.2 Hz), 3.95 (dd, 1H, H-1, J=4.5, 11.4 Hz), 3.82 (d, 2H, H-11), 3.23 (br s, 1H, OH-13), 2.23-1.37 (m, 8H, H-2, 3, 5, 8, 9), 1.85 (s, 3H, Me), 1.48 (s, 3H, Me), 1.15 (s, 3H, Me), 1.10 (s, 9H, $^t$Bu), 1.04 (s, 9H, $^t$Bu);

To a solution of p (320 mg, 441 μmol) in MeOH (5.0 mL) was added NH$_4$F (162 mg, 4.41 mmol), and the mixture was stirred for 3 h at room temperature. The reaction mixture was diluted by addition of EtOAc, and the organic layer was washed with water and dried over anhydrous sodium sulfate. The solution was filtered, and the filtrate was concentrated in vacuo. The resulting residue was purified by neutral flash silica gel column chromatography (3×10, MeOH in CH$_2$Cl$_2$ 0.5-1.5%) to give q (265 mg, 81%) as a white foam.

[α]$^{24}$$_D$+101.07 (c 1.0, CHCl$_3$);

IR (KBr) 3456, 2942, 2890, 2862, 2235, 1716, 1643, 1579, 1475, 1274, 1112 cm$^{-1}$;

$^1$H NMR (CDCl$_3$, 300 MHz) δ8.97 (d, 1H, H-2", J=2.4 Hz), 8.65 (dd, 1H, H-6", J=1.8, 5.1 Hz), 8.21 (d, 2H, H—Ar, J=8.7 Hz), 8.09-8.04 (m, 1H, H-4"), 7.78 (d, 2H, H—Ar, J=8.7 Hz), 7.39-7.35 (m, 1H, H-5"), 6.45 (s, 1H, H-5'), 5.36 (dd, 1H, H-7, J=4.8, 10.8 Hz), 5.03 (d, 1H, H-13, J=3.0 Hz), 4.17 (dd, 1H-1, H-1, J=7.8, 8.4 Hz), 3.60 (dd, 1H, H-11a, J=3.6, 10.5 Hz), 3.31 (dd, 1H, H-11b, J=3.6, 10.5 Hz), 3.03 (br s, 1H, OH-13), 2.17-1.09 (m, 8H, H-2, 3, 5, 8, 9), 1.85 (s, 3H, Me), 1.47 (s, 3H, Me), 1.07-1.05 (m, 18H, $^t$Bu×2), 0.74 (s, 3H, Me);

$^{13}$C NMR (CDCl$_3$, 100 MHz) δ164.05, 163.90, 162.11, 157.22, 151.42, 146.76, 134.00, 132.93, 132.28, 130.16, 127.11, 123.60, 117.82, 116.62, 103.12, 99.31, 83.46, 83.26, 79.91, 73.73, 63.91, 60.08, 54.70, 44.02, 43.28, 40.64, 37.75, 36.34, 29.01, 27.70, 27.17, 27.06, 26.29, 25.45, 20.66, 20.50, 20.28, 20.13, 17.51, 16.68, 12.72;

ESI-LRMS m/z 769 (M+Na$^+$); ESI-HRMS (MeOH) calcd. for C$_{41}$H$_{51}$FN$_2$NaO$_{11}$Si 769.3296 (M+Na$^+$), found 769.3261 (M+Na$^+$).

d) Preparation of 7-O-p-cyanobenzoyl-1,7-dideacetylpyripyropene A (PRD 118)

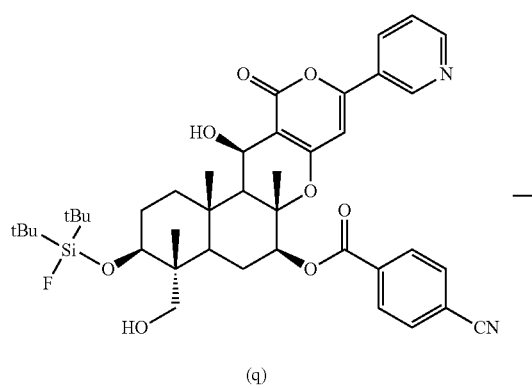

(q)

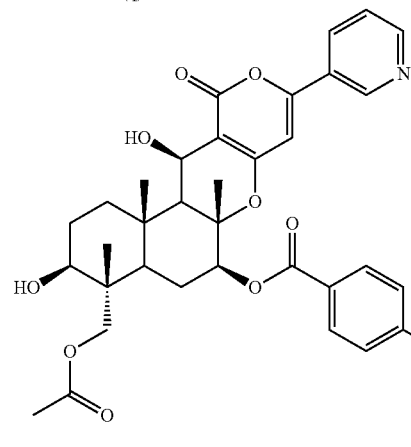

(PRD118)

In a nitrogen atmosphere, Ac$_2$O (101 μL, 1.07 mmol), Et$_3$N (149 μL, 1.07 mmol), and DMAP (10.5 mg, 185.8 mmol) were added to a solution of q (320 mg, 429 μmol) in CH$_2$Cl$_2$ (4.3 mL) and stirred for 1 h at 0° C. MeOH was added to the reaction mixture to terminate the reaction. EtOAc was then added for dilution, and the organic layer was washed with water and dried over anhydrous sodium sulfate. The solution was filtered, and the filtrate was concentrated in vacuo. The resulting residue was dissolved in THF (5.0 mL), and after Et$_3$N.3HF (140 μL, 0.858 mmol) was added, the mixture was stirred for 1 h at room temperature. The reaction mixture was concentrated in vacuo, and the resulting residue was purified by neutral flash silica gel column chromatography (1.5×10+ 1.5, MeOH in CH$_2$Cl$_2$ 4%) to give PRD 118 (275 mg, 2 steps, quantitative) as a white foam.

$^1$H NMR (CDCl$_3$, 400 MHz) δ8.96 (d, 1H, J=2.0 Hz), 8.66 (dd, 1H, H-6", J=1.6, 4.4 Hz), 8.23 (d, 2H, H—Ar, J=8.4 Hz), 8.08-8.05 (m, 1H, H-4"), 7.82 (d, 2H, H—Ar, J=8.4 Hz), 7.41-7.38 (m, 1H, H-5"), 6.42 (s, 1H, H-5'), 5.31-5.28 (m, 1H, H-7), 5.05 (d, 1H, H-13, J=1.6 Hz), 4.23 (d, 1H, H-11a, J=12.0 Hz), 3.75 (d, 1H, H-11b, J=12.0 Hz), 3.53 (dd, 1H, H-1, J=6.0, 10.4 Hz), 2.82 (br s, 1H, OH-13), 2.36 (br s, 1H, OH-1), 2.21-1.17 (m, 8H, H-2, 3, 5, 8, 9), 2.15 (s, 3H, Ac), 1.88 (s, 3H, Me), 1.49 (s, 3H, Me), 0.85 (s, 3H, Me);

ESI-LRMS m/z 651 (M+Na$^+$); ESI-HRMS (MeOH) calcd. for C$_{35}$H$_{36}$N$_2$NaO$_9$ 651.2319 (M+Na$^+$), found 651.2231 (M+Na$^+$).

e) Preparation of 7-O-p-cyanobenzoyl-1,7-dideacetyl-1-O-isobutyrylpyripyropene A (PRD 119)

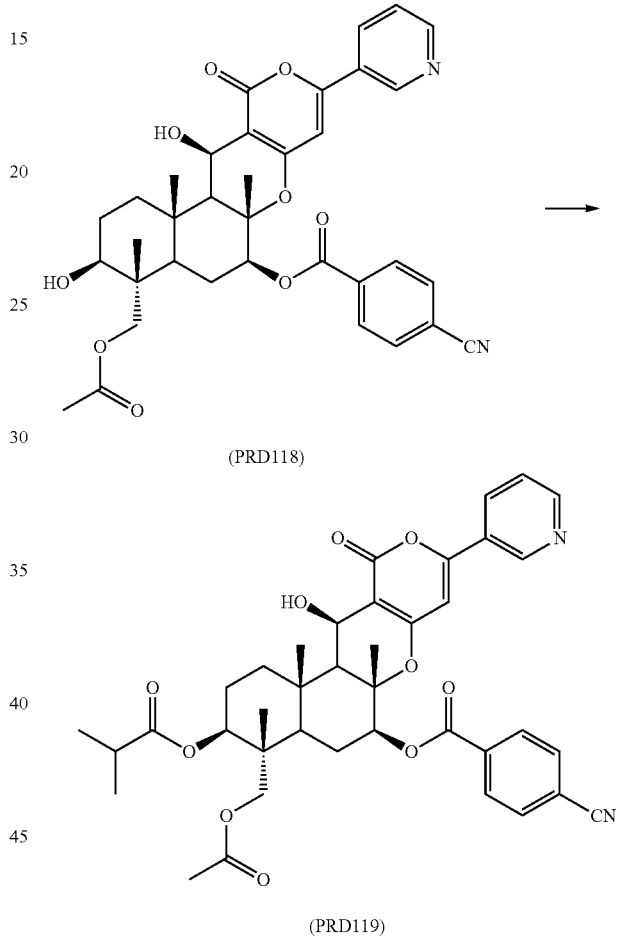

(PRD118)

(PRD119)

In a nitrogen atmosphere, isobutyric anhydride (7.8 μL, 46.7 μmol), Et$_3$N (13 μL, 93.6 μmol, and a catalytic amount of DMAP were added to a solution of PRD 118 (15.0 mg, 23.4 μmol) in CH$_2$Cl$_2$ (0.5 mL) and stirred for 30 min at room temperature. MeOH was added to the reaction mixture to terminate the reaction, and EtOAc was then added for dilution. The organic layer was washed with water and dried over anhydrous sodium sulfate. The resulting residue was purified by neutral flash silica gel column chromatography (1×4, MeOH in CH$_2$Cl$_2$ 0.5-1.5%) to give PRD 119 (16.3 mg, 99%) as a white foam.

$^1$H NMR (CDCl$_3$, 400 MHz) δ8.96 (dd, 1H, H-2", J=0.8, 2.4 Hz), 8.67 (dd, 1H, H-6", J=1.6, 2.4 Hz), 8.21 (d, 2H, H—Ar, J=8.4 Hz), 8.08-8.05 (m, 1H, H-4"), 7.80 (d, 2H, H—Ar, J=8.4 Hz), 7.38 (ddd, 1H, H-5", J=1.2, 5.2, 5.6 Hz), 6.40 (s, 1H, H-5'), 5.27 (dd, 1H, H-7, J=5.2, 116 Hz), 5.04 (d, 1H, H-13, J=3.6 Hz), 4.83 (dd, 1H, H-1, J=5.2, 11.6 Hz), 3.78

(d, 1H, H-11a, J=12.0 Hz), 3.75 (d, 1H, H-11b, J=12.0 Hz), 3.01 (br s, 1H, OH-13), 2.58 (q, 1H, COCHMe$_2$, J=6.8 Hz), 2.21-1.17 (m, 14H, H-2, 3, 5, 8, 9, Me×2), 2.15 (s, 3H, Ac), 1.88 (s, 3H, Me), 1.49 (s, 3H, Me), 0.85 (s, 3H, Me);

ESI-LRMS m/z 699 (MH$^+$); ESI-HRMS (TFA-Na) calcd. for C$_{39}$H$_{43}$N$_2$O$_{10}$ 699.2918 (MH$^+$), found 699.2903 (MH$^+$)

Example 2

Preparation of 7-O-p-cyanobenzoyl-1,7-dideacetyl-1-O-benzoylpyripyropene A (PRD 121)

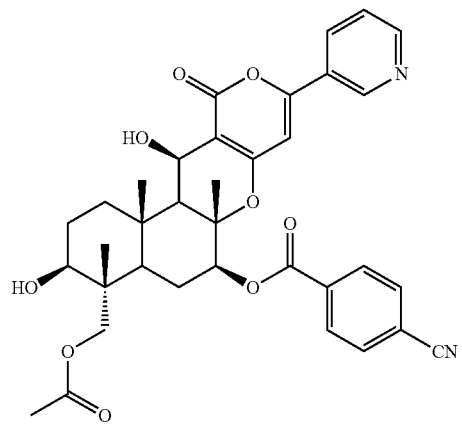

(PRD118)

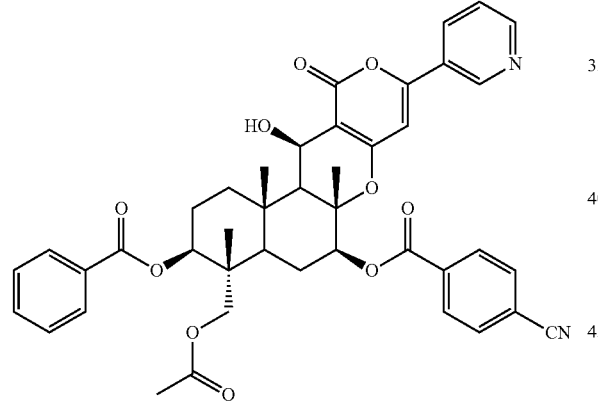

(PRD121)

In a nitrogen atmosphere, benzoic anhydride (13.4 μL, 80.2 μmol), Et$_3$N (11.3 μL, 80.2 μmol), and a catalytic amount of DMAP were added to a solution of PRD 118 (15.0 mg, 23.4 μmol) in CH$_2$Cl$_2$ (0.5 mL) and stirred for 1 h at 0° C. MeOH was added to the reaction mixture to terminate the reaction, and EtOAc was then added for dilution. The organic layer was washed with water and dried over anhydrous sodium sulfate. The resulting residue was purified by preparative TLC (CH$_2$Cl$_2$:MeOH=20:1) to give PRD 121 (12.7 mg, 74%) as a white foam.

$^1$H NMR (CDCl$_3$, 400 MHz) δ8.96 (dd, 1H, H-2'', J=0.8, 2.4 Hz), 8.67 (dd, 1H, H-6'', J=1.6, 4.8 Hz), 8.21 (d, 2H, H—Ar, J=8.8 Hz), 8.09-8.06 (m, 1H, H-5''), 8.02-7.99 (m, 2H, H—Ar), 7.80 (d, 2H, H—Ar, J=8.8 Hz), 7.59-7.55 (m, 1H, H—Ar), 7.46-7.40 (m, 2H, H—Ar), 7.39-7.37 (m, 1H, H-4'), 6.41 (s, 1H, H-5'), 5.31-5.27 (m, 1H, H-7), 5.11 (dd, 1H, H-1, J=4.4, 11.6 Hz), 5.07 (d, 1H, H-13, J=2.0 Hz), 3.84 (d, 1H, H-11a, J=7.2 Hz), 3.82 (dd, 1H, H-11b, J=7.2 Hz), 3.02 (br s, 1H, OH-13), 2.25-1.23 (m, 8H, H-2, 3, 5, 8, 9), 2.13 (s, 3H, Ac), 1.87 (s, 3H, Me), 1.55 (s, 3H, Me), 1.08 (s, 3H, Me);

ESI-LRMS m/z 755 (M+Na$^+$); ESI-HRMS (MeOH) calcd. for C$_{42}$H$_{40}$N$_2$NaO$_{10}$ 755.2581 (M+Na$^+$), found 755.2587 (M+Na$^+$).

Example 3

Preparation of 7-O-p-cyanobenzoyl-1,7-dideacetyl-11-O-isobutyrylpyripyropene A (PRD 081)

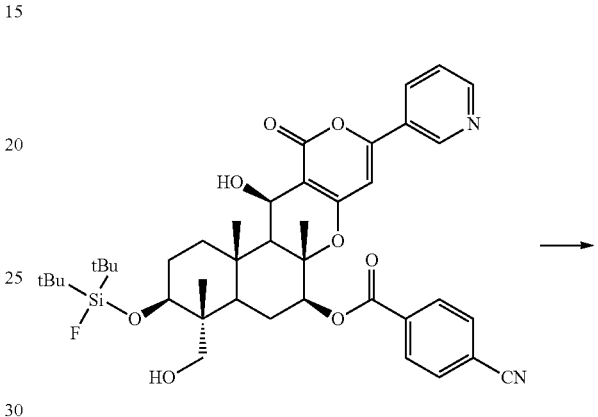

(q)

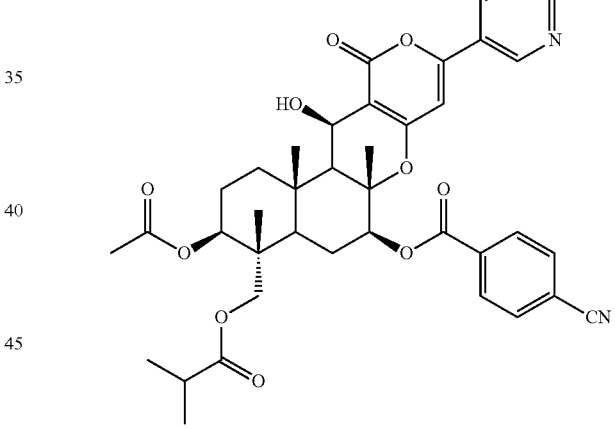

(PRD081)

In a nitrogen atmosphere, isobutyric anhydride (101 μL, 1.07 mmol), Et$_3$N (149 μL, 1.07 mmol), and DMAP (10.5 mg, 85.8 μmol) were added to a solution of q (39.9 mg, 53.5 μmol) in MeCN (1.0 mL) and stirred for 1 h at 0° C. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×4, MeOH in CH$_2$Cl$_2$ 0.5-1.5%), and the fractions containing the product were concentrated. The resulting residue was dissolved in THF (0.5 mL), and after addition of TBAF (100 μL, 1.0 M solution in THF, 0.100 mmol) and AcOH (5.7 μL, 0.100 mmol), the mixture was stirred for 30 min at room temperature. The reaction mixture was concentrated in vacuo, and the resulting residue was purified by neutral flash silica gel column chromatography (1×5, MeOH in CH$_2$Cl$_2$ 2-4%), and the fractions containing the product were concentrated. The resulting residue was dissolved in MeCN (0.5 mL), and Ac$_2$O (6.5 µL, 68.2 µmol), Et$_3$N (19.1 µL, 0.136 mmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×4, MeOH in CH$_2$Cl$_2$ 0.5-1.5%) to give PRD 081 (22.2 mg, 3 steps, 85%) as a white foam.

$^1$H NMR (CDCl$_3$, 400 MHz) δ8.90 (br s, 1H, H-2'), 8.61 (brs, 1H, H-6"), 8.12 (d, 2H, H—Ar, J=8.8 Hz), 8.02 (br s, 1H, H-4"), 7.72 (d, 2H, H—Ar, J=8.8 Hz), 7.34 (m, 1H, H-5"), 6.44 (s, 1H, H-5'), 5.17 (dd, 1H-1, H-7, J=5.2, 11.6 Hz), 4.97 (d, 1H-1, H-13, J=4.0 Hz), 4.75 (dd, 1H, H-1, J=5.2, 11.6 Hz), 3.71 (d, 1H, H-11a, J=12.0 Hz), 3.65 (d, 1H, H-11b, J=12.0 Hz), 2.56 (q, 1H-1, COC$\underline{H}$Me$_2$, J=6.8 Hz), 2.15-1.10 (m, 14H, H-2, 3, 5, 8, 9, Me×2), 1.98 (s, 3H, Ac), 1.78 (s, 3H, Me), 1.43 (s, 3H, Me), 0.85 (s, 3H, Me);

ESI-LRMS m/z 699 (MH$^+$); ESI-HRMS (TFA-Na) calcd. for C$_{39}$H$_{43}$N$_2$O$_{10}$ 699.2918 (MH$^+$), found 699.2914 (MH$^+$).

Example 4

Preparation of 7-O-p-cyanobenzoyl-7,11-dideacetyl-11-O-benzoylpyripyropene A (PRD 143)

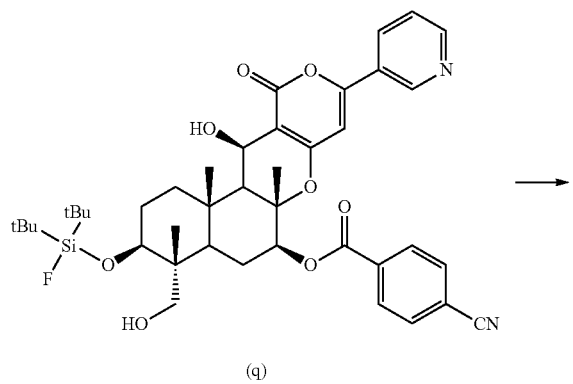

(q)

In a nitrogen atmosphere, Bz$_2$O (9.1 mg, 40.2 µmol), Et$_3$N (5.6 µL, 4.02 µmol), and a catalytic amount of DMAP were added to a solution of q (20.0 mg, 26.8 µmol) in CH$_2$Cl$_2$ (0.5 mL) and stirred for 3 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was dissolved in THF (0.5 mL), and after addition of Et$_3$N.3HF (6.6 mL, 40.2 mmol), the mixture was stirred for 30 min at room temperature. The reaction mixture was concentrated in vacuo, the resulting residue was purified by preparative TLC (CH$_2$Cl$_2$:MeOH=15:1), and the fractions containing the product were concentrated. The resulting residue was dissolved in CH$_2$Cl$_2$ (0.5 mL), and Ac$_2$O (2.4 µL, 25.4 µmol), Et$_3$N (7.1 µL, 51.0 µmol), and a catalytic amount of DMAP were added to the solution and stirred for 0.5 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×4, MeOH in CH$_2$Cl$_2$ 0-1.5%) to give PRD 143 (10.6 mg, 3 steps, 54%) as a white foam.

$^1$H NMR (CDCl$_3$, 400 MHz) δ8.98 (dd, 1H, H-2", J=0.8, 2.4 Hz), 8.67 (dd, 1H, H-6", J=1.6, 4.8 Hz), 8.14 (d, 2H, H—Ar, J=6.8 Hz), 8.09-8.06 (m, 3H, H-4", Ar), 7.67 (d, 2H, H—Ar, J=6.8 Hz), 7.34-7.30 (m, 1H, H—Ar), 7.20-7.16 (m, 2H, H—Ar), 7.07-7.02 (m, 1H, H-5'), 6.38 (s, 1H, H-5'), 5.25 (dd, 1H, H-7, J=4.8, 12.0 Hz), 5.02 (dd, 1H, H-13, J=2.4, 4.0 Hz), 4.92 (dd, 1H, H-1, J=4.8, 11.6 Hz), 4.09-4.07 (m, 2H, H-11), 2.95 (br d, 1H, OH-13, J=2.4 Hz), 2.24-1.21 (m, 8H, H-2, 3, 5, 8, 9), 2.08 (s, 3H, Ac), 1.85 (s, 3H-1, Me), 1.53 (s, 3H, Me), 1.00 (s, 3H, Me);

ESI-LRMS m/z 755 (M+Na$^+$); ESI-HRMS (TFA-Na) calcd. for C$_{42}$H$_{40}$N$_2$NaO$_{10}$ 755.2581 (M+Na$^+$), found 755.2574 (M+Na$^+$).

Example 5

Preparation of 7-O-cyclohexanecarbonyl-1,11-O-diisobutyryl-1,7,11-trideacetylpyripyropene A (PRD 074)

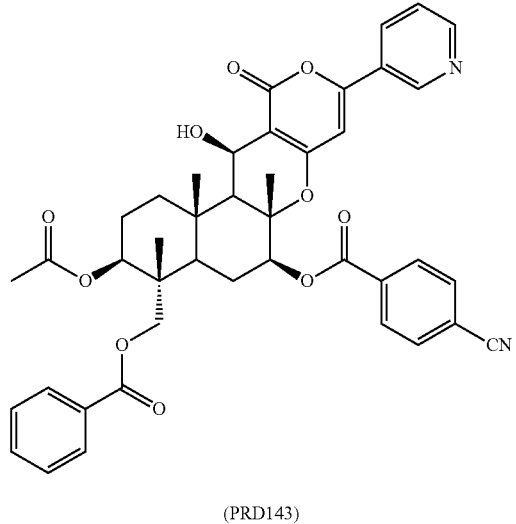

(PRD143)

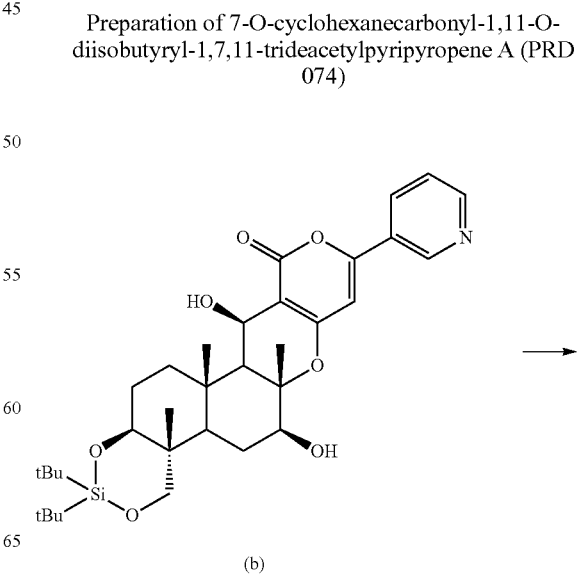

(b)

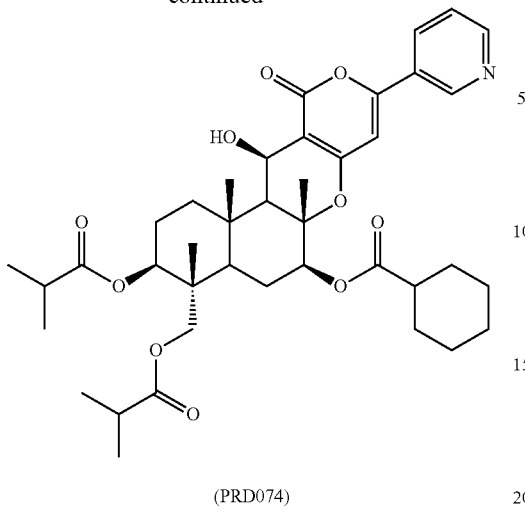

(PRD074)

In a nitrogen atmosphere, cyclohexanecarboxylic acid (3.7 μL, 40.2 μmol), EDCl (7.2 mg, 37.7 μmol), and a catalytic amount of DMAP were added to a solution of b (15.0 mg, 25.1 μmol) in $CH_2Cl_2$ (0.5 mL) and stirred for 2 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was roughly purified by neutral flash silica gel column chromatography (1×4, MeOH in $CH_2Cl_2$ 0-1.5%), and the fractions containing the product were concentrated. The resulting residue was dissolved in THF (0.5 mL), and after addition of $Et_3N.3HF$ (18.0 μL, 113 μmol), the mixture was stirred for 30 min at room temperature. The reaction mixture was concentrated in vacuo, and the resulting residue was roughly purified by neutral flash silica gel column chromatography (1×5+1, MeOH in $CH_2Cl_2$ 3-10%), and the fractions containing the product were concentrated. The resulting residue was dissolved in DMF (0.5 mL), and isobutyric anhydride (11.0 μL, 67.8 μmol), $Et_3N$ (19.0 μL, 136 μmol), and a catalytic amount of DMAP were added to the solution and stirred for 45 min at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×4, MeOH in $CH_2Cl_2$ 0-1.5%) to give PRD 074 (10.6 mg, 3 steps, 60%) as a white foam.

$^1$H NMR ($CDCl_3$, 300 MHz) δ9.00 (dd, 1H, H-2", J=0.6, 1.5 Hz), 8.69 (dd, 1H, H-6", J=1.5, 4.8 Hz), 8.09 (dt, 1H, H-4", J=2.1 8.1 Hz), 7.41 (ddd, 1H, H-5", J=0.6, 1.2, 4.8 Hz), 6.38 (s, 1H, H-5'), 5.01-4.97 (m, 211, H-7, 13), 4.78 (dd, 1H, H-1, J=2.7, 9.0 Hz), 3.77 (d, 1H, H-11a, J=12.0 Hz), 3.68 (d, 1H, H-11b, J=12.0 Hz), 2.92 (br d, 1H-1, OH-13, J=2.7 Hz), 2.61-2.51 (m, 2H, $COCHMe_2$), 2.48-2.36 (m, 1H, COC $HC_6H_{10}$), 2.19-1.21 (m, 30H, H-2, 3, 5, 8, 9, Me×4, COCH $C_6H_{10}$), 1.70 (s, 3H, Me), 1.45 (s, 3H, Me), 0.91 (s, 3H, Me);

ESI-LRMS m/z 730 (M+Na$^+$); ESI-HRMS (TFA-Na) calcd. for $C_{40}H_{53}NNaO_{10}$ 730.3567 (M+Na$^+$), found 730.3554 (M+Na$^+$).

Example 6

Preparation of 7-O-p-nitrobenzoyl-1,11-O-diisobutyryl-1,7,11-trideacetylpyripyropene A (PRD 079)

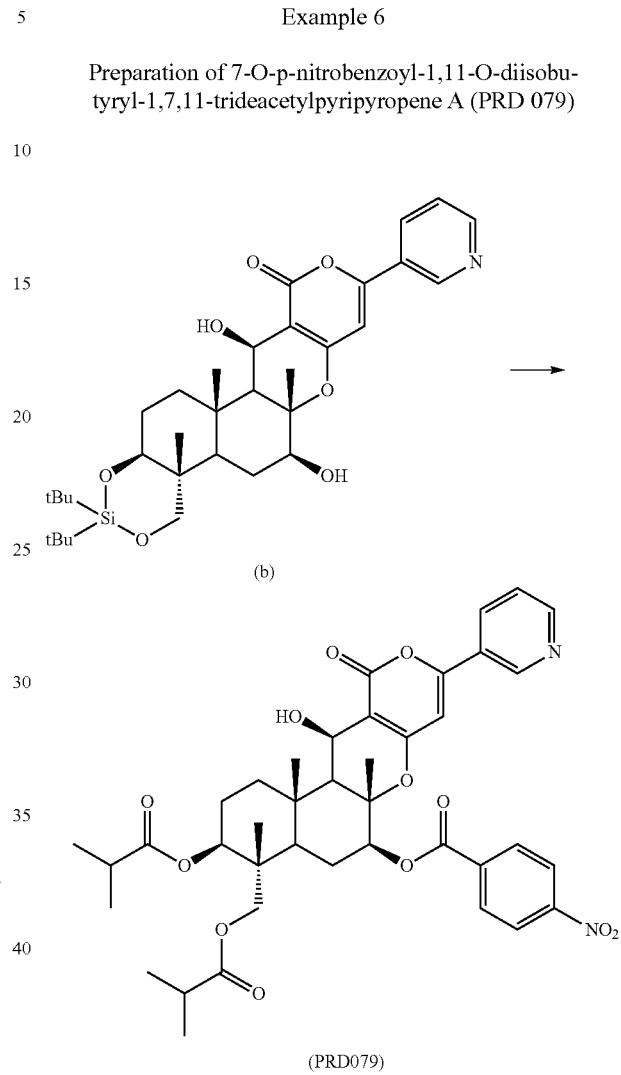

(PRD079)

In a nitrogen atmosphere, p-nitrobenzoic acid (23.0 mg, 0.138 mmol), EDCl (21.0 mg, 0.111 mmol), and a catalytic amount of DMAP were added to a solution of b (55.0 mg, 92.1 μmol) in $CH_2Cl_2$ (1.5 mL) and stirred for 2 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was roughly purified by neutral flash silica gel column chromatography (1×15, MeOH in $CH_2Cl_2$ 0-1.5%), and the fractions containing the product were concentrated. The resulting residue was dissolved in THF (1.0 mL), and after addition of $Et_3N.3HF$ (39.0 μL, 241 μmol, the mixture was stirred for 30 min at room temperature. The reaction mixture was concentrated in vacuo, and the resulting residue was roughly purified by neutral flash silica gel column chromatography (1×5+1, MeOH in $CH_2Cl_2$ 3-10%), and the fractions containing the product were concentrated. The resulting residue was dissolved in DMF (1.0 mL), and isobutyric anhydride (40.0 μL, 241 μmol), $Et_3N$ (67.0 μL, 482 μmol), and a catalytic amount of DMAP were added to the solution and stirred for 30 min at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1.5×5, MeOH in CH$_2$Cl$_2$ 0-1.5%) to give PRD 079 (37.0 mg, 3 steps, 60%) as a white foam.

$^1$H NMR (CDCl$_3$, 300 MHz) δ8.96 (dd, 1H, H-2", J=1.8 Hz), 8.67 (dd, 1H, H-6", J=1.5, 4.8 Hz), 8.33 (d, 2H, H—Ar, J=12.0 Hz), 8.27 (d, 2H, H—Ar, J=12.0 Hz), 8.08-8.04 (m, 1H, H-4"), 7.40-7.36 (m, 1H, H-5"), 6.40 (s, 1H, 11-5'), 5.26 (dd, 1H, H-7, J=4.8, 11.1 Hz), 5.05 (d, 1H, H-13, J=1.8 Hz), 4.84 (dd, 1H, H-1, J=5.1, 11.1 Hz), 3.75 (s, 2H, H-11), 3.00 (br s, 1H, OH-13), 2.64 (q, 1H, COCH, J=7.2 Hz), 2.54 (q, 1H, COCH, J=6.9 Hz), 2.24-1.18 (m, 8H, H-2, 3, 5, 8, 9), 1.87 (s, 3H, Me), 1.52 (s, 3H, Me), 0.94 (s, 3H, Me), 1.30-1.21 (m, 12H, Me×4);

ESI-LRMS m/z 769 (M+Na$^+$); ESI-HRMS (TFA-Na) calcd. for C$_{40}$H$_{46}$N$_2$NaO$_{12}$ 769.2948 (M+Na$^+$), found 769.2941 (M+Na$^+$).

Example 7

Preparation of 7-O-p-cyanobenzoyl-1,11-O-dibenzoyl-1,7,11-trideacetylpyripyropene A (PRD 166)

a) Preparation of 7-O-p-cyanoberizoyl-1,7,11-trideacetylpyripyropene A (r)

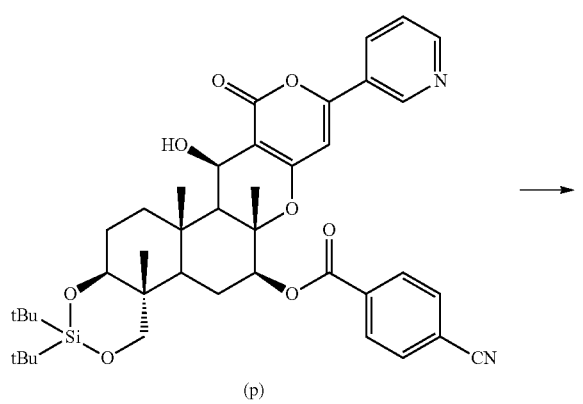

(p)

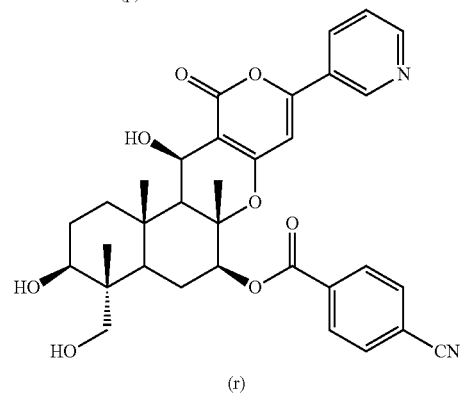

(r)

In the same manner as in Example 5, r (136 mg, 79%) was prepared from p (215 mng, 0.296 mmol).

$^1$H NMR (DMSO-d6, 300 MHz) δ9.00 (dd, 1H, H-2", J=0.6, 2.4 Hz), 8.62 (dd, 1H, H-6", J=1.5, 4.5 Hz), 8.22-8.17 (m, 3H, H-4", Ar), 8.07-8.03 (m, 2H, H—Ar), 7.49-7.44 (m, 1H, H-5"), 6.84 (s, 1H, H-5'), 5.44 (d, 1H, OH-11, J=4.5 Hz), 5.18 (dd, 1H, H-7, J=4.8, 11.4 Hz), 4.80 (dd, 1H, H-13, J=3.3, 5.4 Hz), 4.52 (t, 1H, OH-1, J=1.5 Hz), 4.26 (d, 1H, OH-13, J=2.1 Hz), 3.46 (dd, 1H, H-11a, J=5.4, 10.8 Hz), 3.36-3.27 (m, 1H, H-1), 3.01 (dd, 1H, H-11b, J=4.5, 10.8 Hz), 2.07-1.32 (m, 8H, H-2, 3, 5, 8, 9), 1.80 (s, 3H, Me), 1.34 (s, 3H, Me), 0.58 (s, 3H, Me);

FAB-LRMS m/z 587 (MH$^+$).

b) Preparation of 7-O-p-cyanobenzoyl-1,11-O-dibenzoyl-1,7,11-trideacetylpyripyropene A (PRD 166)

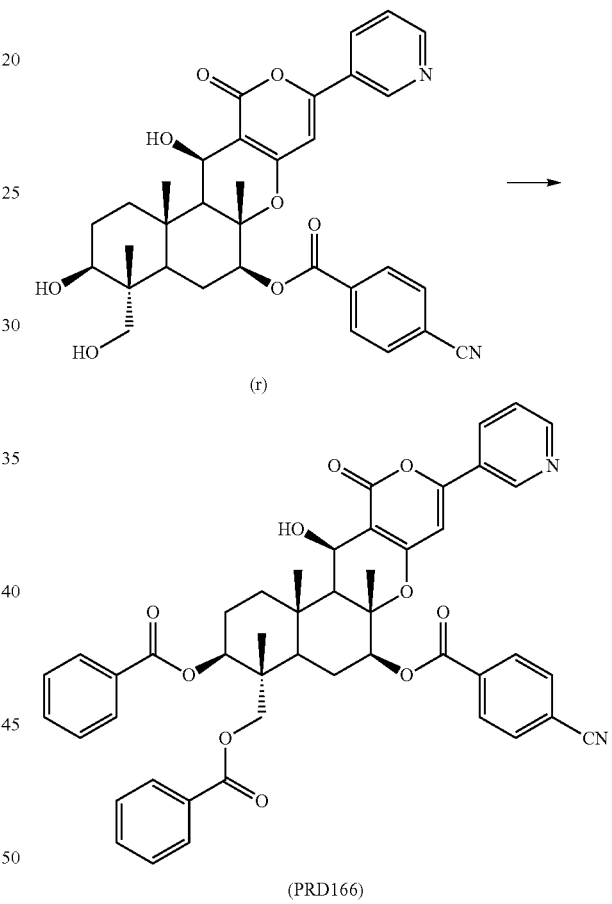

(PRD166)

In a nitrogen atmosphere, Bz$_2$O (23.2 mg, 102 μmol), Et$_3$N (28.5 μL, 205 μmol), and a catalytic amount of DMAP were added to a solution of r (20.0 mg, 34.1 mmol) in CH$_2$Cl$_2$ (0.5 mL) at 0° C. and stirred for 4 h at room temperature. MeOH was added to the reaction mixture to terminate the reaction, and EtOAc was then added. The organic layer was washed with water and dried over anhydrous sodium sulfate. The solution was filtered, and the filtrate was dried over anhydrous sodium sulfate and concentrated in vacuo. The resulting residue was purified by neutral flash silica gel column chromatography (1×3, MeOH in CH$_2$Cl$_2$ 0-2%) to give PRD 166 (24.3 mg, 90%) as a white foam.

$^1$H NMR (CDCl$_3$, 400 MHz) δ8.95 (dd, 1H, H-2", J=0.8, 2.0 Hz), 8.66 (dd, 1H, H-6", J=1.6, 4.8 Hz), 8.19 (d, 2H,

H—Ar, J=4.8 Hz), 8.08-8.01 (m, 5H, H—Ar), 7.78 (d, 2H, H—Ar, J=4.8 Hz), 7.59-7.53 (m, 2H, H-5", Ar), 7.46-7.42 (m, 4H, Ar), 7.39-7.35 (m, 1H, H-4"), 6.38 (s, 1H, H-5'), 5.25 (ddd, 2H-1, J=4.8, 5.2, 11.6 Hz), 5.06 (dd, 1H, H-13, J=2.4, 4.0 Hz), 4.22 (d, 1H, H-11a, J=12.0 Hz), 4.10 (d, 1H, H-11b, J=12.0 Hz), 3.05 (br d, 1H, OH-13, J=2.4 Hz), 2.30-1.52 (m, 8H, H-2, 3, 5, 8, 9), 1.87 (s, 3H, Me), 1.58 (s, 3H, Me), 1.17 (s, 3H, Me);

ESI-LRMS m/z 795 (MH⁺); ESI-HRMS (TFA-Na) calcd. for $C_{47}H_{43}N_2O_{10}$ 795.2918 (MH⁺), found 795.2916 (MH⁺).

Example 8

Preparation of 7-O-p-cyanobenzoyl-1,11-O-dihexanoyl-1,7,11-trideacetylpyripyropene A (PRD 167)

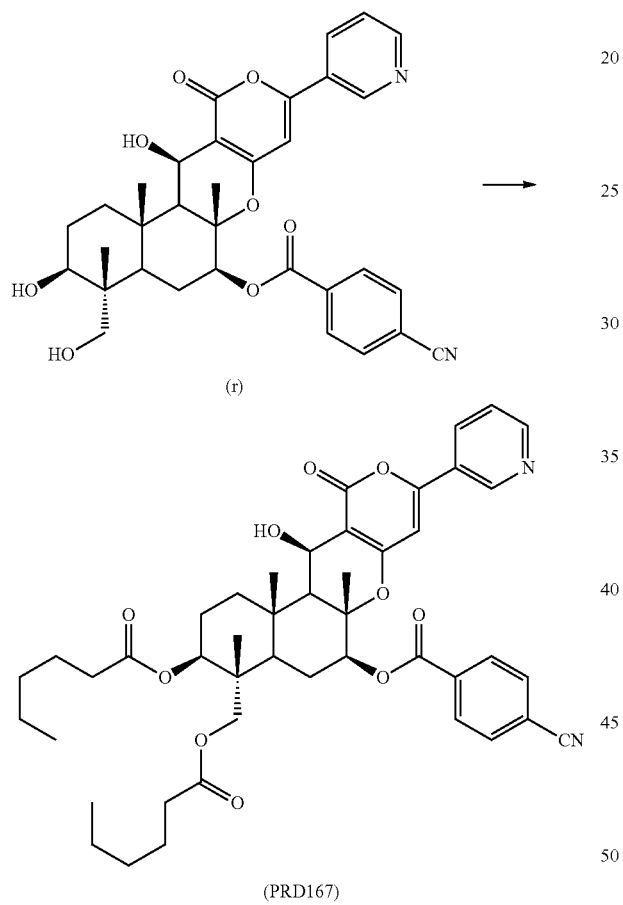

(PRD167)

In a nitrogen atmosphere, n-hexanoic anhydride (23.6 μL, 102. μmol), Et₃N (28.5 μL, 205 μmol), and a catalytic amount of DMAP were added to a solution of r (20.0 mg, 34.1 mmol) in CH₂Cl₂ (0.5 mL) at 0° C. and stirred for 3 h at room temperature. MeOH was added to the reaction mixture to terminate the reaction, and EtOAc was then added. The organic layer was washed with water and dried over anhydrous sodium sulfate. The solution was filtered, and the filtrate was dried over anhydrous sodium sulfate and concentrated in vacuo. The resulting residue was purified by preparative TLC (CH₂Cl₂:MeOH=30:1×2) to give PRD 167 (29.7 mg, quantitative) as a white foam.

¹H NMR (CDCl₃, 400 MHz) δ8.96 (dd, 1H, H-2", J=0.8, 2.4 Hz), 8.67 (dd, 1H, H-6", J=1.6, 5.2 Hz), 8.20 (d, 2H, H—Ar, J=8.8 Hz), 8.06 (ddd, 1H, H-5", J=1.6, 2.4, 8.4 Hz), 7.80 (d, 2H, H—Ar, J=8.8 Hz), 7.38 (ddd, 1H, H-5", 0.8, 4.8, 8.0 Hz), 6.40 (s, 1H, H-5'), 5.27 (dd, 1H, H-7, J=5.2, 11.6 Hz), 5.04 (dd, 1H, H-13, J=2.4, 4.0 Hz), 4.83 (dd, 1H, H-1, J=4.8, 11.6 Hz), 3.78 (d, 1H, H-11a, J=12.0 Hz), 3.73 (d, 1H, H-11b, J=12.0 Hz), 3.03 (br d, 1H, OH-13, J=1.6 Hz), 2.38 (dt, 2H, COC$\underline{H}_2$, J=2.0, 7.2 Hz), 2.29 (dt, 2H, COCH₂, J=2.0, 8.0 Hz), 2.21-1.42 (m, 12H, H-2, 3, 5, 8, 9, hexanoyl), 1.85 (s, 3H, Me), 1.50 (s, 3H, Me), 1.36-1.26 (m, 7H, H-Me, hexanoyl), 0.92-0.88 (m, 10H, hexanoyl);

ESI-LRMS m/z 805 (M+Na⁺); ESI-HRMS (TFA-Na) calcd. for $C_{45}H_{54}N_2NaO_{10}$ 805.3676 (M+Na⁺), found 805.3672 (M+Na⁺).

Example 9

Preparation of 11-O-benzoyl-11-deacetylpyripyropene A (PRD 177)

a) Preparation of 1,11-O-(di-tert-butylsilylene)-1,11-dideacetylpyripyropene A (s)

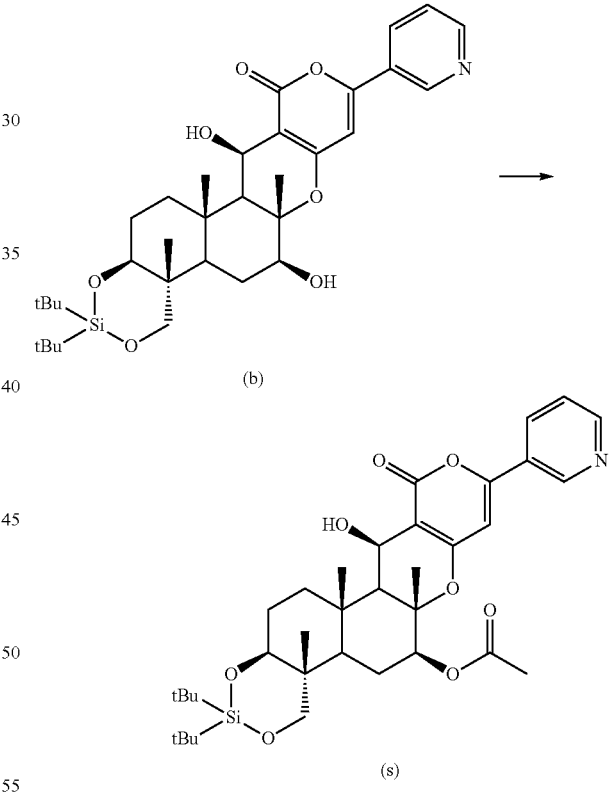

In a nitrogen atmosphere, Ac₂O (61 μL, 0.654 mmol), Et₃N (179 μL, 1.29 mmol), and DMAP (7.2 mg, 58.6 μmol) were added to a solution of b (350 mg, 586 μmol) in CH₂Cl₂ (6.0 mL) and stirred for 1 h at 0° C. MeOH was added to the reaction mixture to terminate the reaction. EtOAc was then added for dilution, and the organic layer was washed with water and dried over anhydrous sodium sulfate. The reaction mixture was concentrated in vacuo, and the resulting residue was purified by neutral flash silica gel column chromatography (2×10, MeOH in CH₂Cl₂ 0-1.5%) to give s (361 mg, 96%) as a white foam.

$^1$H NMR (CDCl$_3$, 400 MHz) δ9.01 (d, 1H, H-2", J=2.4 Hz), 8.68 (dd, 1H, H-6", J=1.2, 4.8 Hz), 8.11-8.08 (m, 1H, H-4"), 7.40 (dd, 1H, H-5", J=5.2, 8.4 Hz), 6.44 (s, 1H, H-5'), 5.00-4.97 (m, 2H, H-7, 13), 3.90 (dd, 1H, H-1, J=4.0, 11.2 Hz), 3.81 (d, 1H, H-11a, J=10.4 Hz), 3.70 (d, 1H, H-11b, J=10.4 Hz), 2.92 (br s, 1H, OH-13), 2.18-1.32 (m, 8H, H-2, 3, 5, 8, 9), 2.17 (s, 3H, Ac), 1.68 (s, 3H, Me), 1.41 (s, 3H, Me), 1.12 (s, 3H, Me), 1.09 (s, 9H, $^t$Bu), 1.04 (s, 9H, $^t$Bu);

ESI-LRMS m/z 662 (M+Na$^+$); ESI-HRMS (MeOH) calcd. for C$_{35}$H$_{49}$NNaO$_8$Si 662.3125 (M+Na$^+$), found 662.3136 (M+Na$^+$).

b) Preparation of 1-(fluoro-di-tert-butylsilyl)-1,11-dideacetylpyripyropene A (t)

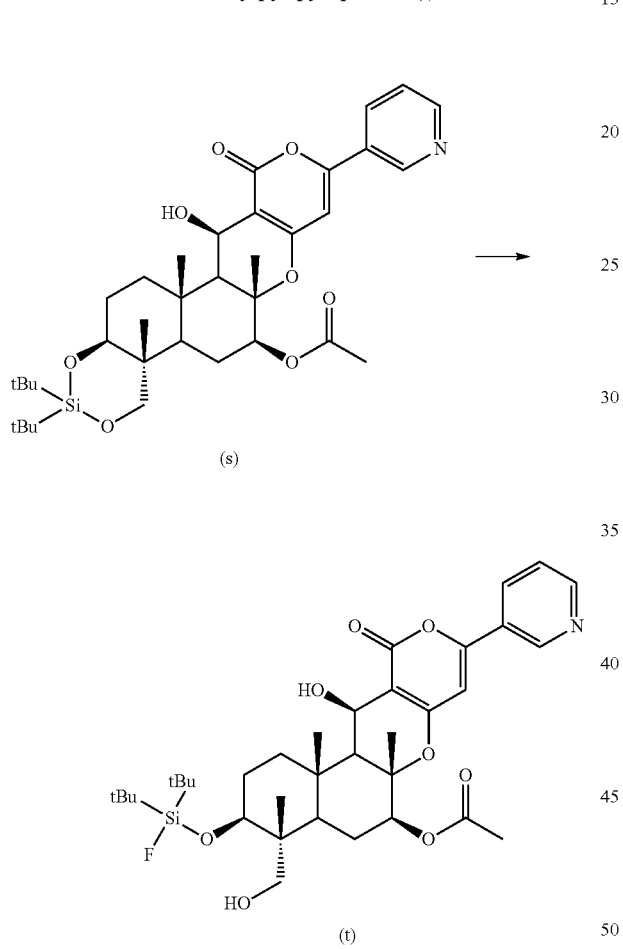

(s)

(t)

In the same manner as in Example 1-c), t (271 mg, 78%) was prepared from s (350 mg, 547 μmol) as a white foam.

$^1$H NMR (CDCl$_3$, 300 MHz) δ9.02 (br s, 1H, H-2"), 8.67 (br d, 1H, H-6", J=4.5 Hz), 8.12-8.08 (m, 1H, H-4"), 7.40 (dd, 1H, H-5", J=4.8, 7.8 Hz), 6.49 (s, 1H, H-5'), 5.07 (dd, 1H, H-7, J=4.8, 7.5 Hz), 4.99 (d, 1H, H-13, J=2.7 Hz), 4.16 (t, 1H, H-1, J=7.8 Hz), 3.56 (d, 1H, H-11a, J=10.8 Hz), 3.31 (d, 1H, H-11b, J=10.8 Hz), 3.18 (br s, 1H, OH-13), 2.53 (br s, 1H, OH-13), 2.12-1.12 (m, 8H, H-2, 3, 5, 8, 9), 2.17 (s, 3H, Ac), 1.71 (s, 3H, Me), 1.42 (s, 3H, Me), 1.05-1.03 (m, 18H, $^t$Bu× 2), 0.71 (s, 3H, Me);

ESI-LRMS m/z 682 (M+Na$^+$); ESI-HRMS (TFA-Na) calcd. for C$_{35}$H$_{50}$FNNaO$_8$Si 682.3187 (M+Na$^+$), found 682.3192 (M+Na$^+$).

c) Preparation of 11-O-benzoyl-11-deacetylpyripyropene A (PRD 177)

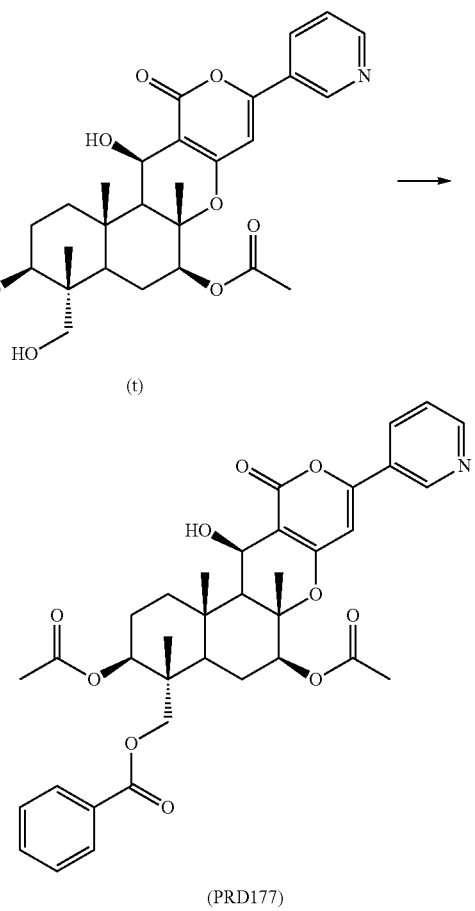

(t)

(PRD177)

In a nitrogen atmosphere, benzoic acid (13.9 mg, 68.3 μmol), EDCl (29.0 mg, 91.0 μmol), and a catalytic amount of DMAP were added to a solution of t (50.0 mg, 45.5 μmol) in CH$_2$Cl$_2$ (0.75 mL) and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was dissolved in THF (0.6 mL), and after addition of Et$_3$N.3HF (11.1 μL, 68.3 μmol), the mixture was stirred for 30 min at room temperature. The reaction mixture was concentrated in vacuo, the resulting residue was roughly purified by neutral flash silica gel column chromatography (1×4, MeOH in CH$_2$Cl$_2$ 0-3%), and the fractions containing the product were concentrated. The resulting residue was dissolved in CH$_2$Cl$_2$ (0.5 mL), and Ac$_2$O (4.6 μL, 48.5 μmol), Et$_3$N (7.4 μL, 52.8 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1×2) to give PRD 177 (26.8 mg, 3 steps, 92%) as a white foam.

$^1$H NMR (CDCl$_3$, 270 MHz) δ9.00 (d, 1H, H-2", J=1.7 Hz), 8.68 (dd, 1H, H-6", J=1.7, 4.6 Hz), 8.10-8.01 (m, 3H, H-4", Ar), 7.54-7.37 (m, 4H, H-5", Ar), 6.43 (s, 1H, H-5'), 4.99-4.85 (m, 2H, H-7, 13), 4.87 (dd, 1H, H-11, J=5.0, 11.2 Hz), 4.10 (d, 1H, H-11a, J=12.0 Hz), 4.07 (d, 1H, H-11b, J=12.0 Hz), 2.95 (br s, 1H, OH-13), 2.20-0.87 (m, 8H, H-2, 3, 5, 8, 9), 2.14 (s, 3H, Ac), 2.06 (s, 3H, Ac), 1.70 (s, 311, Me), 1.47 (s, 3H, Me), 0.98 (s, 3H, Me);

ESI-LRMS m/z 668 (M+Na$^+$); ESI-HRMS (TFA-Na) calcd. for C$_{36}$H$_{39}$NNaO$_{10}$ 668.2472 (M+Na$^+$), found 668.2456 (M+Na$^+$).

Example 10

Preparation of 1,11-O-diisobutyryl-1,11-dideacetylpyripyropene A (PRD 187)

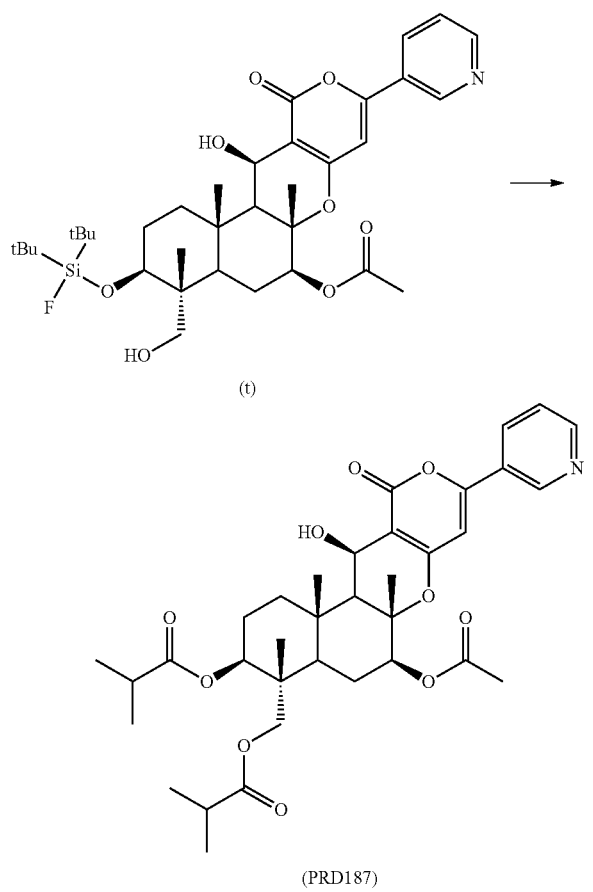

(PRD187)

In a nitrogen atmosphere, Et$_3$N.3HF (4.9 μL, 30.3 μmol, was added to a solution of t (20.0 mg, 30.3 μmol in THF (0.5 mL) and stirred for 30 min at room temperature. The reaction mixture was concentrated in vacuo, the resulting residue was roughly purified by neutral flash silica gel column chromatography (1×4+1, MeOH in CH$_2$Cl$_2$ 3-10%), and the fractions containing the product were concentrated. The resulting residue was dissolved in DMF (0.5 mL), and isobutyric anhydride (15.0 μL, 91.0 μmol), Et$_3$N (25.0 μL, 182 μmol), and a catalytic amount of DMAP were added to the solution and stirred for 30 min at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1.5×5, MeOH in CH$_2$Cl$_2$ 01.5%) to give PRD 187 (19.3 mg, 2 steps, quantitative) as a white foam.

$^1$H NMR (CDCl$_3$, 400 MHz) δ9.01 (dd, 1H, H-2", J=0.8, 2.4 Hz), 8.69 (dd, 1H, H-6", J=1.6, 5.2 Hz), 8.10 (ddd, 1H, H-4", J=1.6, 2.4, 8.0 Hz), 7.40 (ddd, 1H, H-5", J=1.2, 4.8, 8.0 Hz), 6.46 (s, 1H, H-5'), 5.02-5.00 (m, 2H, H-7, 13), 4.79 (dd, 1H, H-1, J=5.2, 11.6 Hz), 3.75 (d, 1H, H-11a, J=12.0 Hz), 3.73 (d, 1H, H-11b, J=12.0 Hz), 2.94 (br d, 1H, OH-13, J=2.0 Hz), 2.58 (q, 1H, COCH, J=6.8 Hz), 2.53 (q, 1H, COCH, J=6.8 Hz), 2.19-1.14 (m, 20H, H-2, 3, 5, 8, 9, Me×4), 2.16 (s, 3H, Ac), 1.70 (s, 3H, Me), 1.45 (s, 3H, Me), 0.91 (s, 3H, Me);

ESI-LRMS m/z 662 (M+Na$^+$); ESI-HRMS (TFA-Na) calcd. for C$_{35}$H$_{45}$NNaO$_{10}$ 662.2941 (M+Na$^+$), found 662.2932 (M+Na$^+$).

Example 11

Preparation of 1,11-O-benzylidene-7-O-cyclohexanecarbonyl-1,7,11-trideacetylpyripyropene A (PRD 080)

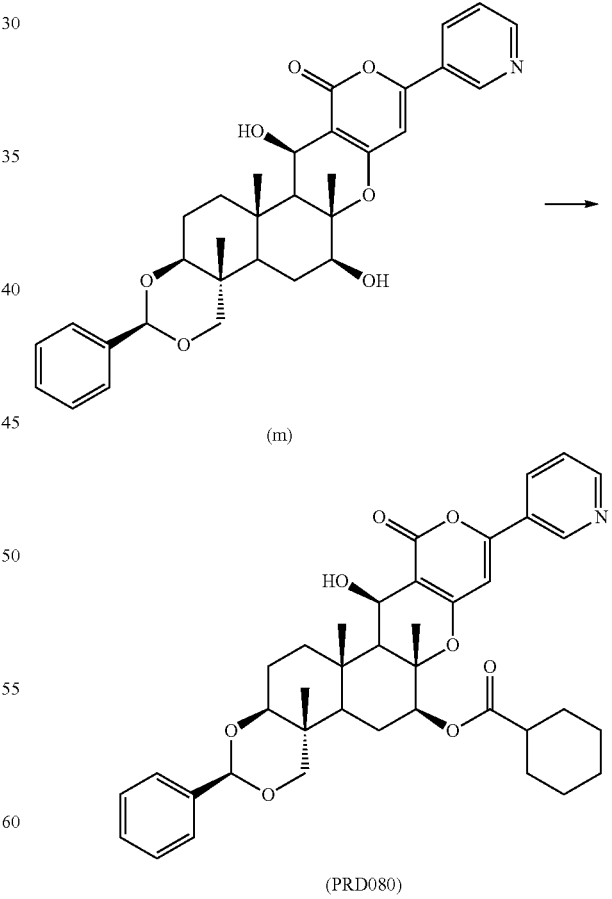

(PRD080)

In a nitrogen atmosphere, cyclohexanecarboxylic acid (6.8 μL, 0.110 mmol), EDCl (31.6 mg, 0.165 mmol), and a catalytic amount of DMAP were added to a solution in CH$_2$Cl$_2$ (1.5 mL) of m (30.0 mg, 55.0 μmol) obtained by the method of Obata et al. (J. Antibiot., Vol. 49, pp. 1149-1156, 1996) and stirred for 3 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC ($CH_2Cl_2$: MeOH=20:1×2) to give PRD 080 (34.2 mg, 95%) as a white foam.

$^1$H NMR ($CDCl_3$, 400 MHz) δ9.01 (dd, 1H, H-2", J=0.4, 2.0 Hz), 8.69 (dd, 1H, H-6", J=1.2, 4.8 Hz), 8.11-8.08 (m, 1H, H-4"), 7.52-7.49 (m, 2H, H—Ar), 7.42-7.27 (m, 4H, H-5", Ar), 6.39 (s, 1H, H-5'), 5.54 (s, 1H, ArC$\underline{H}$), 5.05-5.00 (m, 2H, H-7, 13), 3.88 (d, 1H, H-11a, J=10.4 Hz), 3.52-3.46 (m, 2H, H-11b, 1), 3.07 (br s, 1H, OH-13), 2.45-2.40 (m, 1H, H—COC$\underline{H}$($CH_2$)$_5$), 2.24 (dd, 1H, H-3a, J=3.2, 10.4 Hz), 2.03-1.18 (m, 17H, H-2, 3b, 5, 8, 9, cyclohexyl), 1.71 (s, 3H, Me), 1.47 (s, 3H, Me), 1.24 (s, 3H, Me);

ESI-LRMS m/z 678 (M+Na$^+$); ESI-HRMS (TFA-Na) calcd. for $C_{39}H_{45}NNaO_8$ 678.3043 (M+Na$^+$), found 678.3066 (M+Na$^+$).

Example 12

Preparation of 1,11-O-benzylidene-7-O-benzoyl-1,7,11-trideacetylpyripyropene A (PRD 122)

DMAP were added to a solution of m (15.0 mg, 27.5 μmol) in $CH_2Cl_2$ (0.5 mL) and stirred for 4 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC ($CH_2Cl_2$:MeOH=20:1) to give PRD 122 (17.8 mg, quantitative) as a white foam.

$^1$H NMR ($CDCl_3$, 400 MHz) δ8.97 (dd, 1H, H-2", J=0.4, 2.0 Hz), 8.66 (dd, 1H, H-6", J=1.6, 4.8 Hz), 8.15-8.12 (m, 2H, H—Ar), 8.08-8.05 (m, 1H, H-4"), 7.65-7.60 (m, 1H, H—Ar), 7.53-7.49 (m, 4H, 11-5", Ar), 7.40-7.34 (m, 4H, H—Ar), 6.43 (s, 1H, H-5'), 5.56 (s, 1H, C$\underline{H}$Ar), 5.31-5.28 (m, 1H, H-7), 5.04 (d, 1H, H-13, J=4.0 Hz), 3.91 (d, 1H, H-11a, J=10.4 Hz), 3.56-3.43 (m, 2H, H-11b, 1), 3.02 (br s, 1H, OH-13), 2.29 (d, 1H, H-3a, J=13.2 Hz), 2.04-1.20 (m, 7H, H-2, 3b, 5, 8, 9), 1.87 (s, 3H, Me), 1.53 (s, 3H, Me), 1.26 (s, 3H, Me);

ESI-LRMS m/z 672 (M+Na$^+$); ESI-HRMS (TFA-Na) calcd. for $C_{39}H_{39}NaNO_8$ 672.2573 (M+Na$^+$), found 675.2587 (M+Na$^+$).

Example 13

Preparation of 1,11-O-benzylidene-1,11-dideacetylpyripyropene A (PRD 186)

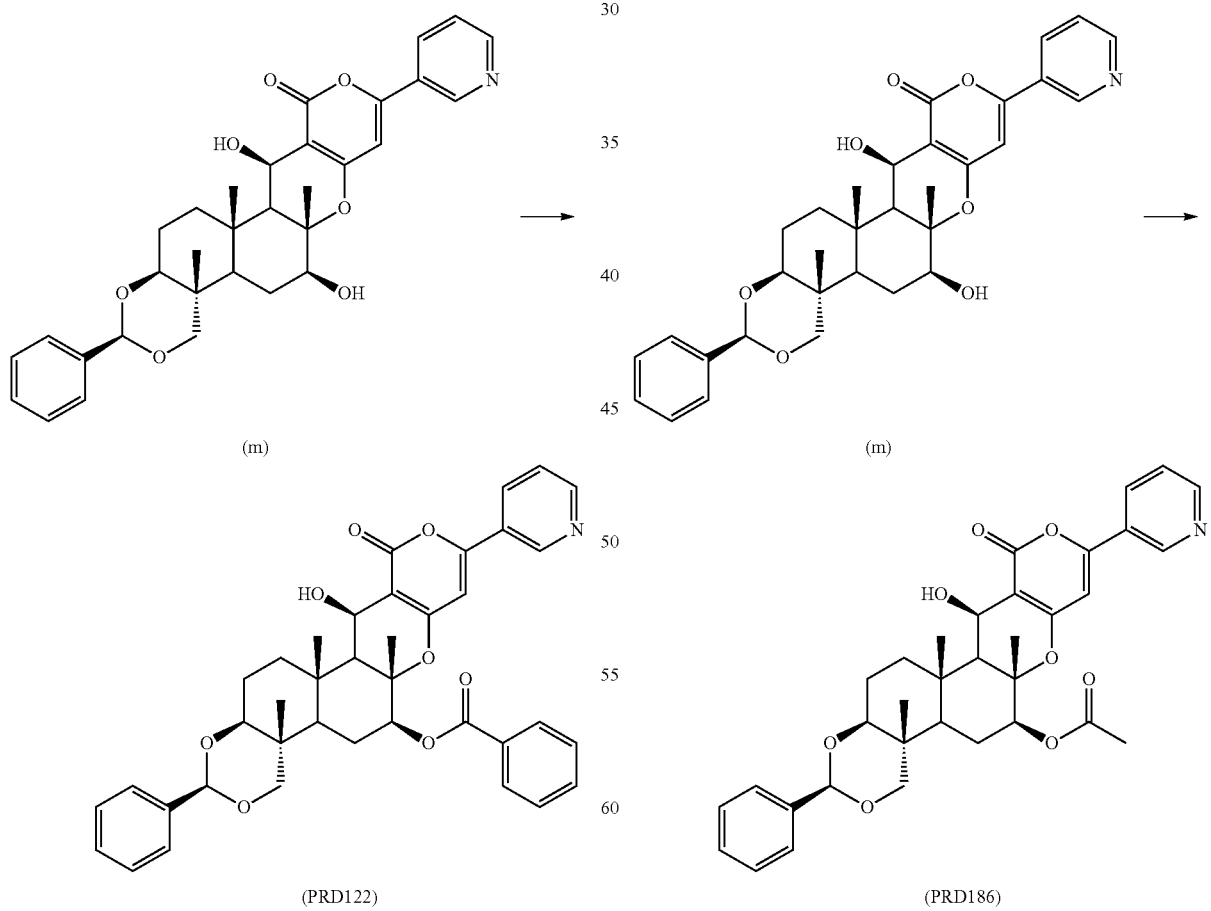

(m)

(PRD122)

(m)

(PRD186)

In a nitrogen atmosphere, benzoic acid (7.0 mg, 55.0 μmol), EDCl (16.0 mg, 82.6 μmol), and a catalytic amount of In a nitrogen atmosphere, $Ac_2O$ (2.9 μL, 30.3 μmol), Et3N (8.4 mL, 60.5 μmol), and a catalytic amount of DMAP were added to a solution of m (15.0 mg, 27.5 μmol) in CH$_2$Cl$_2$ (0.5 mL) and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 186 (13.2 mg, 82%) as a white foam.

$^1$H NMR (CDCl$_3$, 400 MHz) δ9.02 (dd, 1H, H-2", J=0.8, 2.4 Hz), 8.69 (dd, 1H, H-6", J=1.6, 4.8 Hz), 8.10 (ddd, 1H, J=2.0, 2.4, 7.8 Hz), 7.52-7.49 (m, 2H, H—Ar), 7.42-7.39 (m, 1H, H-5"), 7.38-7.34 (m, 3H, H—Ar), 6.46 (s, 1H, H-5'), 5.54 (s, 1H, CHAr), 5.04 (dd, 1H, H-7, J=5.6, 11.6 Hz), 5.01-5.00 (m, 1H, H-13), 3.88 (d, 1H, H-11a, J=10.4 Hz), 3.53-3.47 (m, 2H, H-11b, 1), 2.96 (br d, 1H, OH-13, J=1.6 Hz), 2.25 (d, 1H, H-3a, J=12.8 Hz), 2.16-1.17 (m, 7H, H-2, 3b, 5, 8, 9), 2.18 (s, 3H, Ac), 1.71 (s, 3H, Me), 1.49 (s, 3H, Me), 1.24 (s, 3H, Me);

ESI-LRMS m/z 610 (M+Na$^+$); ESI-HRMS (TFA-Na) calcd. for C$_{34}$H$_{37}$NaNO$_8$ 610.2417 (M+Na+), found 610.2405 (M+Na$^+$).

Example 14

Preparation of 1,11-O-p-dimethylaminobenzylidene-7-O-p-cyanobenzoyl-1,7,11-trideacetylpyripyropene A (PRD 123)

In a nitrogen atmosphere, p-N,N-dimethylaminobenzaldehyde (81.5 mg, 0.547 mmol) and PPTS (2.7 mg, 10.9 μmol) were added to a solution of a (25.0 mg, 109 μmol) in DMF (1.0 mL) and stirred for 72 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1.5×4, MeOH in CH$_2$Cl$_2$ 04%), and the fractions containing the product were concentrated. The resulting residue was dissolved in CH$_2$Cl$_2$ (0.5 mL), and p-cyanobenzoic acid (6.6 mg, 38.2 μmol), EDCl (11.5 mg, 38.2 μmol), and a catalytic amount of DMAP were added to the solution and stirred for 2 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×4, MeOH in CH$_2$Cl$_2$ 0-1.5%) to give PRD 123 (20.0 mg, 2 steps, 47%) as a white foam.

$^1$H NMR (CDCl$_3$, 400 MHz) δ8.96 (dd, 1H, H-2", J=0.8, 2.0 Hz), 8.67 (dd, 1H, H-6", J=1.6, 4.8 Hz), 8.22 (d, 2H, H—Ar, J=4.8 Hz), 8.10 (ddd, 1H, H-4", J=1.6, 2.4, 8.0 Hz), 7.80 (d, 2H, H—Ar, J=4.8 Hz), 7.40-7.36 (m, 1H, H-5"), 7.35 (d, 2H, H—Ar, J=4.4 Hz), 6.71 (d, 2H, H—Ar, J=4.4 Hz), 6.40 (s, 1H, H-5'), 5.47 (s, 1H, CHAr), 5.31 (dd, 1H, H-7, J=5.6, 11.2 Hz), 5.04 (d, 1H, H-13, J=3.2 Hz), 3.86 (d, 1H, H-11a, J=10.0 Hz), 3.52-3.48 (m, 2H, H-11b, 1), 3.03 (br s, 1H, OH-13), 2.93 (s, 6H, NMe$_2$), 2.27 (d, 1H, H-3a, J=12.8 Hz), 1.89-1.18 (m, 7H, H-2, 3b, 5, 8, 9), 1.85 (s, 3H, Me), 1.52 (s, 3H, Me), 1.25 (s, 3H, Me);

ESI-LRMS m/z 718 (MH$^+$); ESI-HRMS (TFA-Na) calcd. for C$_{42}$H$_{44}$N$_3$O$_8$ 718.3128 (MH$^+$), found 718.3145 (M+Na+).

Example 15

Preparation of 1,11-O-o-methylbenzylidene-7-O-p-cyanobenzoyl-1,7,11-trideacetylpyripyropene A (PRD 125)

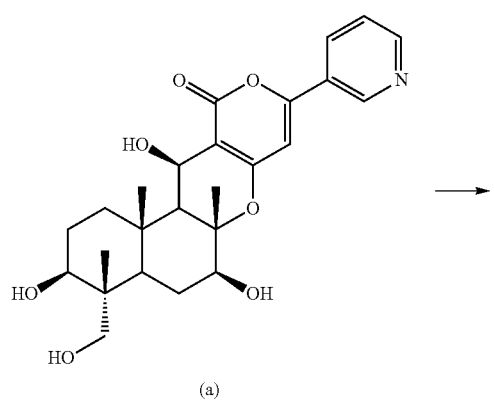

(a)

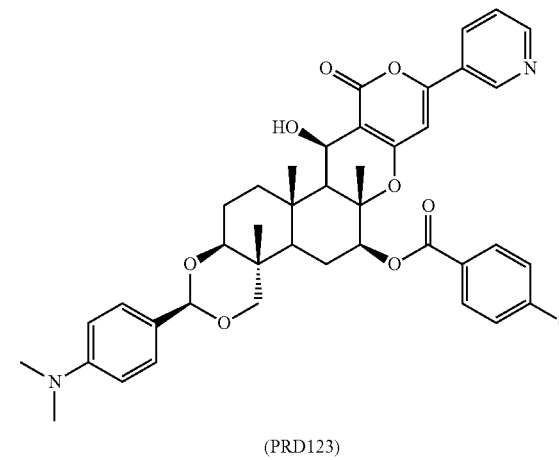

(PRD123)

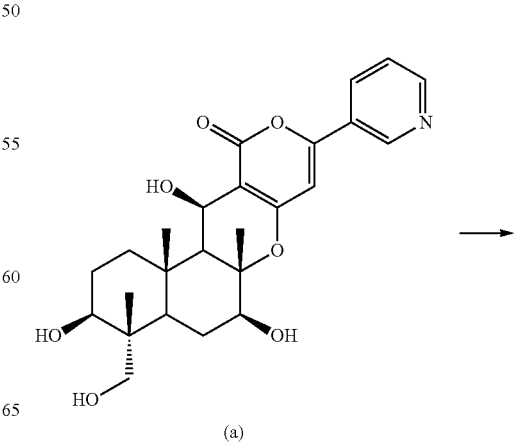

(a)

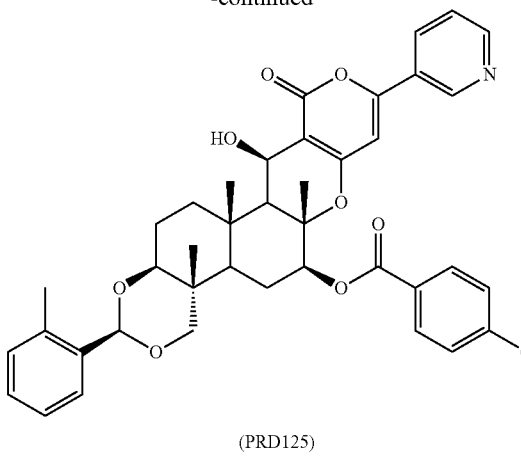

(PRD125)

In a nitrogen atmosphere, o-toluene aldehyde (48.8 μL, 0.410 mmol) and PPTS (0.4 mg, 1.36 μmol) were added to a solution of a (12 mg, 27.3 μmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 05%), and the fractions containing the product were concentrated. The resulting residue was dissolved in $CH_2Cl_2$ (0.5 mL), and p-cyanobenzoic acid (5.3 mg, 35.8 μmol), EDCl (10.3 mg, 53.7 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-1.5%) to give PRD 125 (11.2 mg, 2 steps, 60%) as a white foam.

$^1$H NMR (CDCl$_3$, 400 MHz) δ8.97 (dd, 1H, H-2″, J=0.8, 3.2 Hz), 8.67 (dd, 1H, H-6″, J=2.0, 6.4 Hz), 8.22 (d, 2H, H—Ar, J=11.2 Hz), 8.09-8.05 (m, 1H, H-4″), 7.81 (d, 2H, H—Ar, J=11.2 Hz), 7.65-7.62 (m, 1H, H—Ar), 7.40-7.36 (m, 1H, H-5″), 7.24-7.23 (m, 2H, H—Ar), 7.22-7.13 (m, 1H, H—Ar), 6.40 (s, 1H, H-5′), 5.70 (s, 1H, C<u>H</u>Ar), 5.30 (dd, 1H, H-7, J=8.0, 12.8 Hz), 5.05 (dd, 1H, H-13, J=3.2, 4.8 Hz), 3.90 (d, 1H, H-11a, J=13.6 Hz), 3.58-3.52 (m, 2H, H-11b, 1), 3.00 (br d, 1H, OH-13, J=2.8 Hz), 2.40 (s, 3H, Ar<u>Me</u>), 2.29 (d, 1H, H-3a, J=17.2 Hz), 2.05-1.18 (m, 7H-2, 3b, 5, 8, 9), 1.86 (s, 3H-Me), 1.53 (s, 3H, Me), 1.26 (s, 3H, Me);

ESI-LRMS m/z 689 (MH$^+$); ESI-HRMS (TFA-Na) calcd. for $C_{41}H_{41}N_2O_8$ 689.2863 (MH$^+$), found 689.2885 (MH$^+$).

Example 16

Preparation of 1,11-O-p-methylbenzylidene-7-O-p-cyanobenzoyl-1,7,11-trideacetylpyripyropene A (PRD 126)

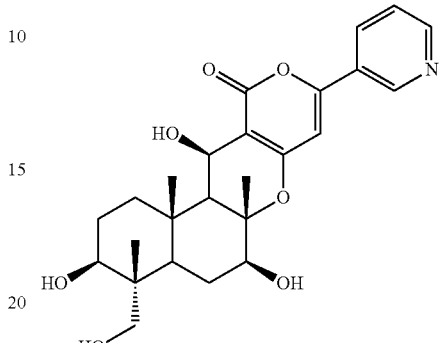

(a)

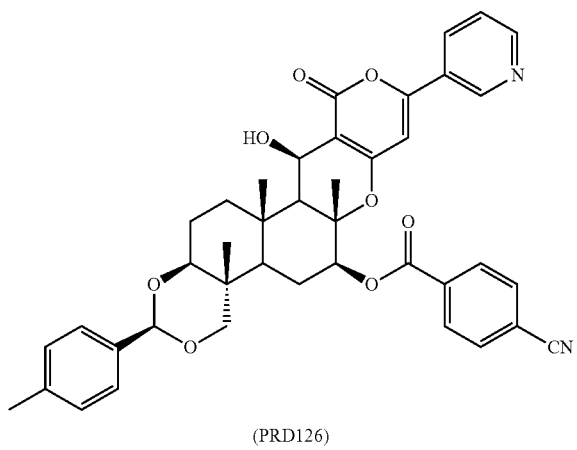

(PRD126)

In a nitrogen atmosphere, p-toluene aldehyde (96.5 μL, 0.820 mmol) and PPTS (0.7 mg, 2.73 μmol) were added to a solution of a (25 mg, 54.5 μmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-5%), and the fractions containing the product were concentrated. The resulting residue was dissolved in $CH_2Cl_2$ (0.5 mL), and p-cyanobenzoic acid (5.3 mg, 35.8 μmol), EDCl (10.3 mg, 53.7 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-1.5%) to give PRD 126 (11.5 mg, 2 steps, 31%) as a white foam.

$^1$H NMR (CDCl$_3$, 400 MHz) δ8.97 (dd, 1H, H-2", J=1.2, 3.2 Hz), 8.67 (dd, 1H, H-6", J=2.0, 6.4 Hz), 8.22 (d, 2H, H—Ar, J=10.8 Hz), 8.07 (ddd, 1H, H-4", J=2.0, 3.2, 10.4 Hz), 7.81 (d, 2H, H—Ar, J=10.8 Hz), 7.39 (d, 2H, H—Ar, J=10.4 Hz), 7.38-7.36 (m, 1H, H-5"), 7.18 (m, 2H, H—Ar, J=10.4 Hz), 6.40 (s, 1H, H-5'), 5.52 (s, 1H, CHAr), 5.31 (dd, 1H, H-7, J=5.6, 11.2 Hz), 5.04 (dd, 1H, H-13, J=4.0, 5.2 Hz), 3.89 (d, 1H, H-11a, J=13.6 Hz), 3.53-3.49 (m, 2H, H-11b, 1), 2.98 (br d, 1H, OH-13, J=2.4 Hz), 2.34 (s, 3H, ArMe), 2.34-1.18 (m, 8H, H-2, 3, 5, 8, 9), 1.86 (s, 3H, Me), 1.52 (s, 3H, Me), 1.25 (s, 3H, Me);

SI-LRMS m/z 689 (MH$^+$); ESI-HRMS (TFA-Na) calcd. for C$_{41}$H$_{41}$N$_2$O$_8$ 689.2863 (MH$^+$), found 689.2858 (MH$^+$).

Example 17

Preparation of 1,11-O-o-methylbenzylidene-7-O-p-fluorobenzoyl-1,7,11-trideacetylpyripyropene A (PRD 155)

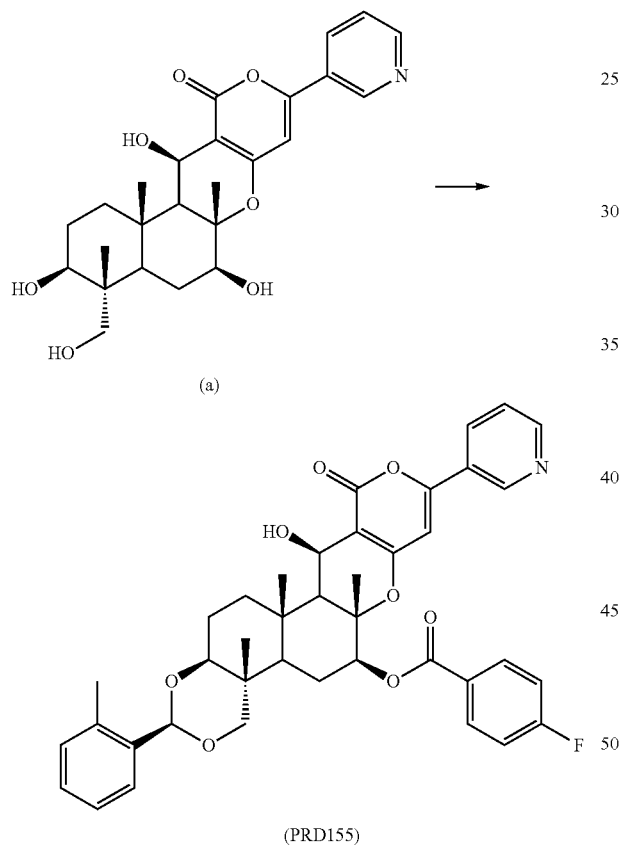

(PRD155)

In a nitrogen atmosphere, o-toluene aldehyde (48.8 μL, 0.410 mmol) and PPTS (0.4 mg, 1.36 μmol) were added to a solution of a (12 mg, 27.3 μmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-fluorobenzoic acid (5.0 mg, 35.8 μmol), EDCl (10.3 mg, 53.7 μmol), and a catalytic amount of DMAP were added to the solution and stirred for 4 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 155 (10.9 mg, 2 steps, 59%) as a white foam.

$^1$H NMR (CDCl$_3$, 400 MHz) δ8.97 (d, 1H, H-2", J=1.6 Hz), 8.66 (dd, 1H, H-6", J=1.6, 5.2 Hz), 8.16-8.12 (m, 2H, H—Ar), 8.08-8.05 (m, 1H, H-4"), 7.65-7.62 (m, 1H, H—Ar), 7.40-7.36 (m, 1H, H-5"), 7.24-7.13 (m, 5H, H—Ar), 6.42 (s, 1H, H-5'), 5.70 (s, 1H, CHAr), 5.27 (dd, 1H, H-7, J=6.4, 11.6 Hz), 5.04 (d, 1H, H-13, J=3.2 Hz), 3.91 (d, 1H, H-11a, J=10.4 Hz), 3.57-3.52 (m, 2H, H-11b, 1), 2.97 (br s, 1H, OH-13), 2.40 (s, 3H, ArMe), 2.29 (dd, 1H, H-3a, J=3.2, 10.4 Hz), 2.00-1.26 (m, 7H, H-2, 3b, 5, 8, 9), 1.85 (s, 3H, Me), 1.52 (s, 314, Me), 1.26 (s, 3H, Me);

ESI-LRMS m/z 704 (M+Na$^+$); ESI-HRMS (TFA-Na) calcd. for C$_{40}$H$_{40}$FNNaO$_8$ 704.2636 (M+Na$^+$), found 704.2636 (M+Na$^+$).

Example 18

Preparation of 1,11-O-p-methylbenzylidene-7-O-p-fluorobenzoyl-1,7,11-trideacetylpyripyropene A (PRD 156)

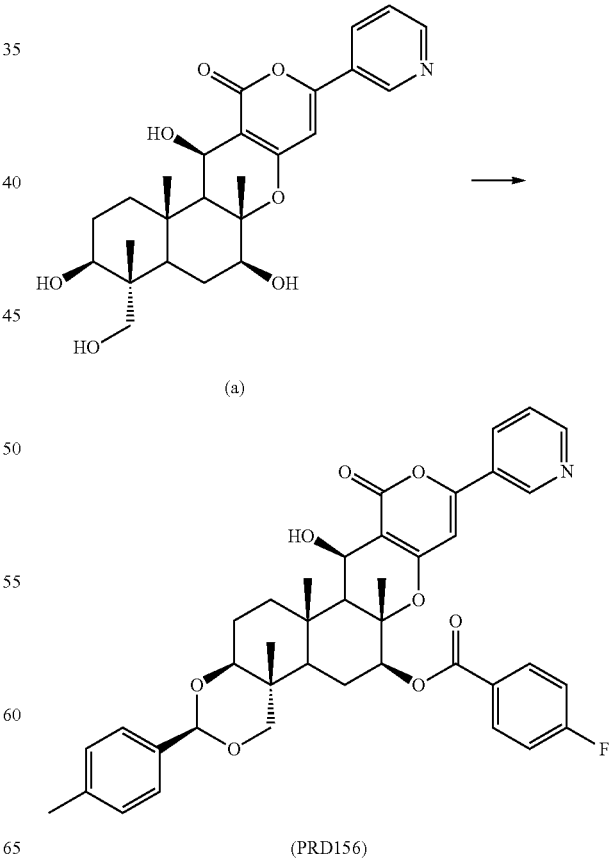

(PRD156)

In a nitrogen atmosphere, p-toluene aldehyde (96.5 μL, 0.820 mmol) and PPTS (0.7 mg, 2.73 μmol) were added to a solution of a (25 mg, 54.5 μmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-fluorobenzoic acid (4.0 mg, 28.6 μmol), EDCl (8.2 mg, 42.9 μmol), and a catalytic amount of DMAP were added to the solution and stirred for 12 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 156 (11.5 mg, 2 steps, 20%) as a white foam.

$^1$H NMR (CDCl$_3$, 400 MHz) δ8.97 (dd, 1H, H-2% J=1.6, 2.4 Hz), 8.67 (dd, 1H, H-6", J=1.6, 4.8 Hz), 8.16-8.12 (m, 2H, H—Ar), 8.08-8.05 (m, 1H, H-4"), 7.40-7.36 (m, 3H, H-5", Ar), 7.20-7.15 (m, 4H, H—Ar), 6.42 (s, 1H, H-5'), 5.52 (s, 1H, C$\underline{H}$Ar), 5.28 (dd, 1H, H-7, J=5.6, 11.2 Hz), 5.05 (dd, 1H, H-13, J=1.6, 3.6 Hz), 3.88 (d, 1H, H-11a, J=10.4 Hz), 3.54-3.49 (m, 2H, H-11b, 1), 2.98 (br d, 1H, OH-13, J=1.6 Hz), 2.34 (s, 3H, Ar$\underline{Me}$), 2.28 (ddd, 1H, H-3a, J=2.8, 6.0, 13.2 Hz), 1.98-1.18 (m, 7H, H-2, 3b, 5, 8, 9), 1.85 (s, 3H, Me), 1.52 (s, 3H, Me), 1.25 (s, 3H, Me);

ESI-LRMS m/z 704 (M+Na$^+$); ESI-HRMS (TFA-Na) calcd. for C$_{40}$H$_{40}$FNNaO$_8$ 704.2636 (M+Na$^+$), found 704.2646 (M+Na$^+$).

Example 19

Preparation of 1,11-O-m-methylbenzylidene-7-O-p-cyanobenzoyl-1,7,11-trideacetylpyripyropene A (PRD 157)

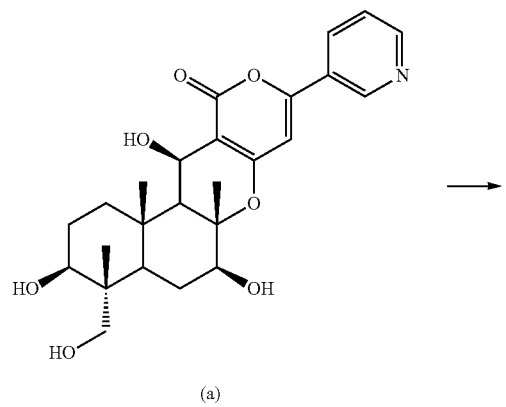

(a)

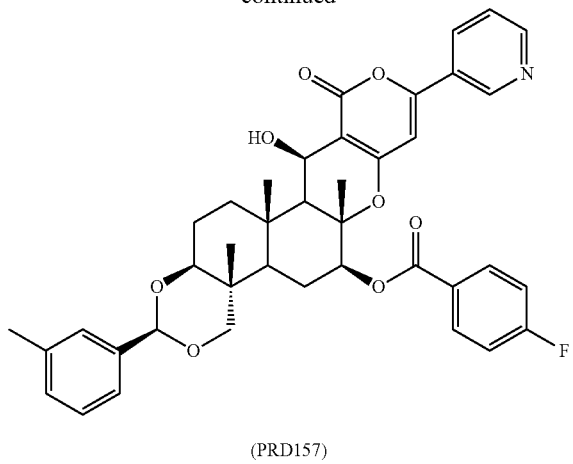

(PRD157)

In a nitrogen atmosphere, m-toluene aldehyde (232 μL, 0.820 mmol) and PPTS (0.7 mg, 2.73 μmol) were added to a solution of a (60.0 mg, 131 μmol) in DMF (1.0 Ml) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×13, MeOH in CH$_2$Cl$_2$ 0-4%). A portion of the resulting product (10 mg, 17.9 μmol) was dissolved in CH$_2$Cl$_2$ (0.5 mL), and p-cyanobenzoic acid (3.2 mg, 21.5 μmol), EDCl (5.1 mg, 26.9 μmol), and a catalytic amount of DMAP were added to the solution and stirred for 3 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 157 (12.4 mg, quantitative) as a white foam.

$^1$H NMR (CDCl$_3$, 400 MHz) δ8.97 (dd, 1H, J=0.8, 2.0 Hz), 8.67 (dd, 1H, H-6", J=2.0, 4.8 Hz), 8.22 (d, 2H, H—Ar, J=8.4 Hz), 8.07 (ddd, 1H, H-4", J=1.6, 2.4, 8.4 Hz), 7.81 (d, 2H, H—Ar, J=8.4 Hz), 7.40-7.33 (m, 1H, H-5"), 7.24 (s, 1H, H—Ar), 7.17-7.15 (m, 2H, H—Ar), 7.15 (dd, 1H, H—Ar, J=0.8, 7.6 Hz), 6.40 (s, 1H, H-5'), 5.52 (s, 1H, C$\underline{H}$Ar), 5.31 (dd, 1H, H-7, J=5.6, 11.6 Hz), 5.05 (dd, 1H, H-13, J=2.0, 8.0 Hz), 3.89 (d, 1H, H-11a, J=10.4 Hz), 3.55-3.51 (m, 2H, H-11b, 1), 2.98 (br d, 1H, OH-13, J=2.0 Hz), 2.36 (s, 3H, Ar$\underline{Me}$), 2.30 (d, 1H, H-3a, J=9.6 Hz), 2.00-1.26 (m, 7H, H-2, 3b, 5, 8, 9), 1.86 (s, 3H, Me), 1.53 (s, 3H, Me), 1.26 (s, 3H, Me);

SI-LRMS m/z 689 (MH$^+$); ESI-HRMS (TFA-Na) calcd. for C$_{41}$H$_{41}$N$_2$O$_8$ 689.2863 (MH$^+$), found 689.2864 (MH$^+$).

Example 20

Preparation of 1,11-O-m-methylbenzylidene-7-O-p-fluorobenzoyl-1,7,11-trideacetylpyripyropene A (PRD 158)

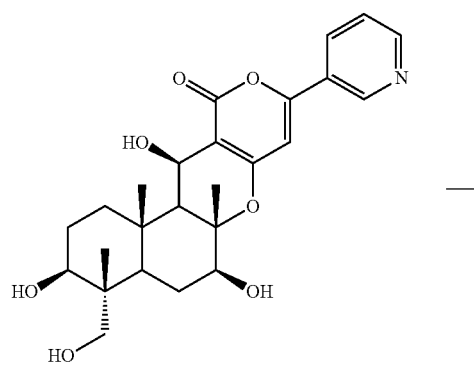

(a)

(PRD158)

In a nitrogen atmosphere, m-toluene aldehyde (232 μL, 0.820 mmol) and PPTS (0.7 mg, 2.73 μmol) were added to a solution of a (60.0 mg, 131 μmol) in DMF (1.0 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×13, MeOH in $CH_2Cl_2$ 0-4%). A portion of the resulting product (10 mg, 17.9 μmol) was dissolved in $CH_2Cl_2$ (0.5 mL), and p-fluorobenzoic acid (3.8 mg, 26.8 μmol), EDCI (6.2 mg, 26.8 μmol), and a catalytic amount of DMAP were added to the solution and stirred for 8 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC ($CH_2Cl_2$:MeOH=20:1) to give PRD 158 (11.9 mg, 98%) as a white foam.

$^1$H NMR (CDCl$_3$, 400 MHz) δ8.97 (dd, 1H, H-2", J=0.4, 2.4 Hz), 8.67 (dd, 1H, H-6", J=1.6, 4.8 Hz), 8.16-8.12 (m, 2H, H—Ar), 8.07 (ddd, 1H, H-4", J=1.6, 2.4, 8.2 Hz), 7.39-7.33 (m, 1H, H-5"), 7.30 (s, 1H, H—Ar), 7.28-7.17 (m, 2H, H—Ar), 7.16-7.14 (m, 3H, H—Ar), 6.42 (s, 1H, H-5'), 5.52 (s, 1H, C<u>H</u>Ar), 5.29 (dd, 1H, H-7, J=6.0, 11.2 Hz), 5.04 (dd, 1H, H-13, J=2.0, 4.0 Hz), 3.90 (d, 1H, H-11a, J=10.4 Hz), 3.55-3.50 (m, 2H, H-11b, 1), 2.96 (br d, 1H, OH-13, J=2.0 Hz), 2.36 (s, 3H, Ar<u>Me</u>), 2.30 (d, 1H, H-3a, J=9.6 Hz), 2.00-1.26 (m, 7H, H-2, 3b, 5, 8, 9), 1.86 (s, 3H, Me), 1.53 (s, 3H, Me), 1.26 (s, 3H, Me);

ESI-LRMS m/z 704 (M+Na$^+$); ESI-HRMS (TFA-Na) calcd. for $C_{40}H_{40}FNNaO_8$ 704.2636 (M+Na$^+$), found 704.2636 (M+Na$^+$).

Example 21

Preparation of 1,11-O-o,p-dimethylbenzylidene-7-O-p-cyanobenzoyl-1,7,11-trideacetylpyripyropene A (PRD 159)

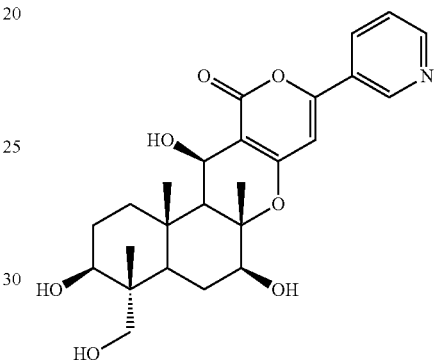

(a)

(PRD159)

In a nitrogen atmosphere, 2,4-dimethylbenzaldehyde (137 μL, 0.985 mmol) and a catalytic amount of PPTS were added to a solution of a (30 mg, 65.5 μmol) in DMF (1.0 mL) and stirred for 48 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-5%), and the fractions containing the product were concentrated. The resulting residue was dissolved in $CH_2Cl_2$ (0.5 mL), and p-cyanobenzoic acid (2.3 mg, 15.9 μmol), EDCl (4.0 mg, 20.7 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 159 (7.5 mg, 2 steps, 20%) as a white foam.

$^1$H NMR (CDCl$_3$, 400 MHz) δ8.97 (dd, 1H, H-2", J=1.6, 2.4 Hz), 8.67 (dd, 1H, H-6", J=1.6, 4.8 Hz), 8.16-8.12 (m, 2H, H—Ar), 8.08-8.05 (m, 1H, H-4"), 7.40-7.36 (m, 3H, H-5", Ar), 7.20-7.15 (m, 3H, H—Ar), 6.42 (s, 1H, H-5'), 5.52 (s, 1H, CHAr), 5.28 (dd, 1H, H-7, J=5.6, 11.2 Hz), 5.05 (dd, 1H, H-13, J=1.6, 3.6 Hz), 3.88 (d, 1H, H-11a, J=10.4 Hz), 3.54-3.49 (m, 2H, H-11b, 1), 2.98 (br d, 1H, H-13, J=1.6 Hz), 2.34 (s, 3H, ArMe), 2.29 (s, 3H, ArMe), 1.96-1.25 (m, 8H, H-2, 3, 5, 8, 9), 1.85 (s, 3H, Me), 1.52 (s, 3H, Me), 1.25 (s, 3H, Me);

AB-LRMS m/z 703 (MH$^+$); FAB-HRMS (CHCl$_3$) calcd. for C$_{42}$H$_{43}$N$_2$O$_8$ 703.3019 (MH$^+$), found 703.3039 (MH$^+$).

Example 22

Preparation of 1,11-O-o,p-dimethylbenzylidene-7-O-p-fluorobenzoyl-1,7,11-trideacetylpyripyropene A (PRD 160)

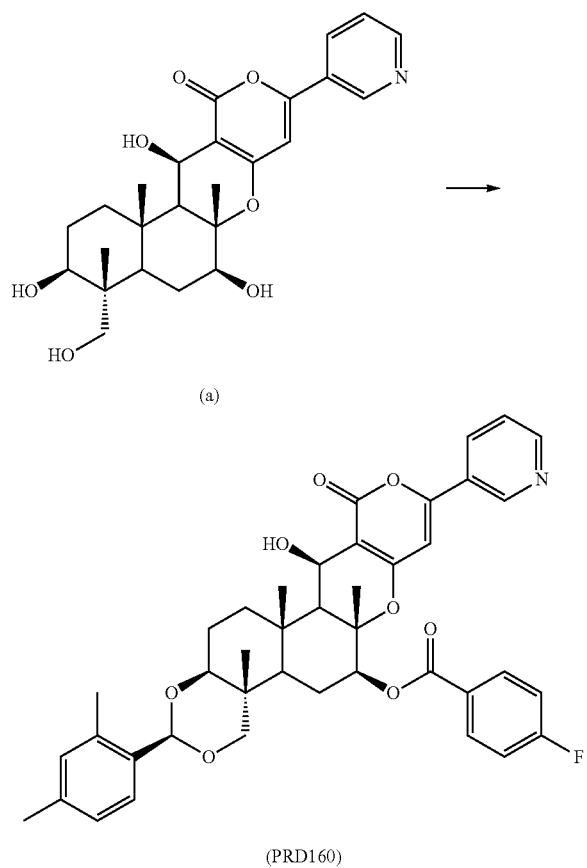

(PRD160)

In a nitrogen atmosphere, 2,4-dimethylbenzaldehyde (137 μL, 0.985 mmol) and a catalytic amount of PPTS were added to a solution of a (30 mg, 65.5 μmol) in DMF (1.0 mL) and stirred for 48 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-fluorobenzoic acid (2.6 mg, 18.3 μmol), EDCl (4.7 mg, 24.4 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 160 (3.7 mg, 2 steps, 8.1%) as a white foam.

$^1$H NMR (CDCl$_3$, 300 MHz) δ8.98 (dd, 1H, H-2", J=2.0, 2.8 Hz), 8.67 (dd, 1H, H-6", J=2.4, 46.8 Hz), 8.16-8.11 (m, 2H, H—Ar), 8.09-8.05 (in, 1H, H-4"), 7.51 (d, 1H, H—Ar, J=10.4 Hz), 7.40-7.36 (m, 1H, H-5"), 7.18 (dt, 2H, H—Ar, J=2.8, 11.6 Hz), 7.02 (d, 1H, H—Ar, J=10.4 Hz), 6.96 (s, 1H, H—Ar), 6.42 (s, 1H, H-5'), 5.66 (s, 1H, CHAr), 5.27 (dd, 1H, H-7, J=8.4, 14.4 Hz), 5.04 (dd, 1H, H-13, J=2.4, 4.8 Hz), 3.90 (d, 1H, H-11a, J=13.6 Hz), 3.55-3.89 (m, 2H, H-11b, 1), 2.91 (br d, 1H, OH-13, J=2.4 Hz), 2.35 (s, 3H, ArMe), 2.31 (s, 3H, ArMe), 2.31-1.22 (m, 8H, H-2, 3, 5, 8, 9), 1.85 (s, 3H, Me), 1.57 (s, 3H, Me), 1.25 (s, 3H, Me);

ESI-LRMS m/z 718 (M+Na$^+$); ESI-HRMS (TFA-Na) calcd. for C$_{41}$H$_{42}$FNNaO$_8$ 718.2792 (M+Na$^{30}$), found 718.2798 (M+Na$^+$).

Example 23

Preparation of 1,11-O-o-methoxybenzylidene-7-O-p-cyanobenzoyl-1,7,11-trideacetylpyripyropene A (PRD 161)

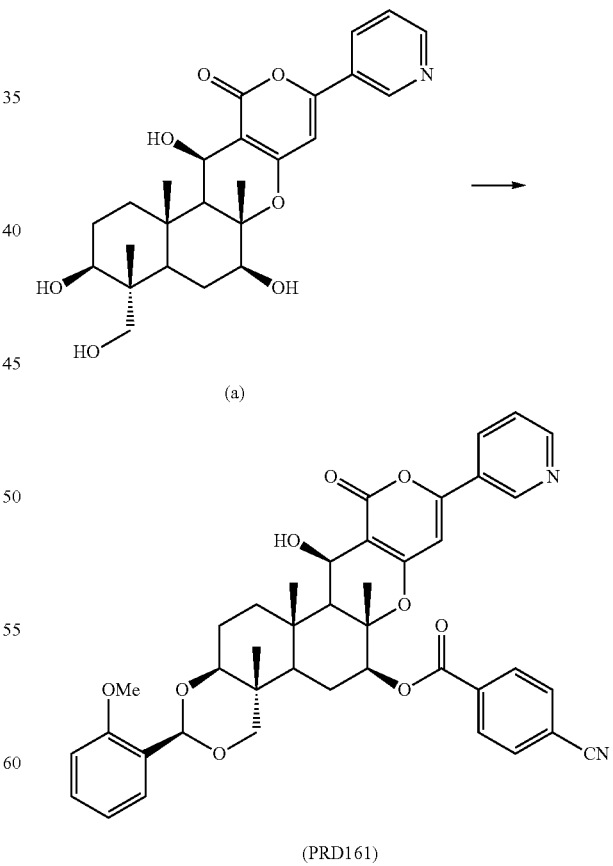

(PRD161)

In a nitrogen atmosphere, o-anisaldehyde (73.6 μL, 0.607 mmol) and a catalytic amount of PPTS were added to a solution of a (18.5 mg, 40.3 µmol) in DMF (1.0 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 and p-cyanobenzoic acid (3.3 mg, 22.6 µmol), EDCl (5.0 mg, 26.1 µmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 161 (13.0 mg, 2 steps, 50%) as a white foam.

$^1$H NMR (CDCl$_3$, 400 MHz) δ8.97 (dd, 1H, H-2", J=0.4, 2.0 Hz), 8.70 (dd, 1H, H-6", J=1.6, 5.2 Hz), 8.22 (d, 2H, H—Ar, J=8.8 Hz), 8.08-8.05 (m, 1H, H-4"), 7.80 (d, 2H, H—Ar, J=8.8 Hz), 7.64 (dd, 1H, H—Ar, J=2.0, 8.0 Hz), 7.40-7.36 (m, 1H, H-5"), 7.33-7.28 (m, 1H, H—Ar), 6.99 (dt, 1H, H—Ar, J=0.8, 7.6 Hz), 6.89 (dd, 1H, H—Ar, J=0.8, 8.0 Hz), 6.40 (s, 1H, H-5'), 5.96 (s, 1H, CHAr), 5.30 (dd, 1H, H-7, J=5.6, 11.2 Hz), 5.04 (dd, 1H, H-13, J=2.4, 4.0 Hz), 3.88 (d, 1H, H-11a, J=10.0 Hz), 3.85 (s, 3H, OMe), 3.58-3.53 (m, 2H, H-11b, 1), 2.99 (br d, 1H, OH-13, J=2.0 Hz), 2.30-2.27 (m, 1H, H-3a), 1.89-1.26 (m, 7H, H-2, 3b, 5, 8, 9), 1.86 (s, 3H, Me), 1.53 (s, 3H, Me), 1.26 (s, 3H, Me);

ESI-LRMS m/z 727 (M+Na$^+$); ESI-HRMS (TFA-Na) calcd. for C$_{41}$H$_{40}$N$_2$NaO$_9$ 727.2632 (M+Na$^+$), found 727.2634 (M+Na$^+$).

Example 24

Preparation of 1,11-O-o-methoxybenzylidene-7-O-p-fluorobenzoyl-1,7,11-trideacetylpyripyropene A (PRD 162)

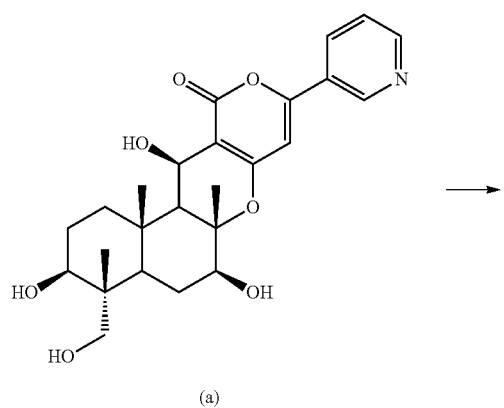

(a)

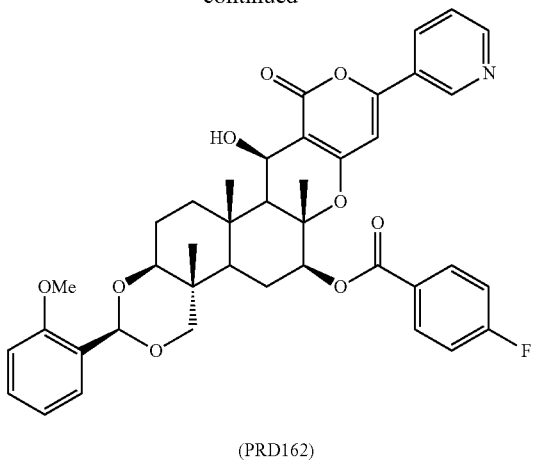

(PRD162)

In a nitrogen atmosphere, o-anisaldehyde (59.7 µL, 0.492 mmol) and a catalytic amount of PPTS were added to a solution of a (15.0 mg, 32.7 µmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-fluorobenzoic acid (3.3 mg, 22.6 µmol), EDCl (5.0 mg, 26.1 µmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 162 (9.2 mg, 2 steps, 41%) as a white foam.

$^1$H NMR (CDCl$_3$, 400 MHz) δ8.97 (dd, 1H, H-2", J=1.6, 2.4 Hz), 8.67 (dd, 1H, H-6", J=1.6, 4.4 Hz), 8.16-8.12 (m, 2H, H—Ar), 8.06 (ddd, 1H, H-4", J=1.6, 2.4, 8.0 Hz), 7.65 (dd, 1H, H—Ar, J=2.0, 8.0 Hz), 7.39-7.36 (m, 1H, H-5"), 7.32-7.28 (m, 1H, H—Ar), 7.20-7.15 (m, 2H, H—Ar), 6.99 (dt, 1H, H—Ar, J=0.8, 3.2 Hz), 6.87 (d, 1H, H—Ar, J=7.6 Hz), 6.42 (s, 1H, H-5'), 5.96 (s, 1H, CHAr), 5.28 (dd, 1H, H-7, J=6.0, 11.6 Hz), 5.04 (dd, 1H, H-13, J=2.0, 4.0 Hz), 3.88 (d, 1H, H-11a, J=10.4 Hz), 3.84 (s, 3H, OMe), 3.57-3.52 (m, 2H, H-11b, 1), 2.95 (br d, 1H, OH-13, J=2.0 Hz), 2.29-2.26 (m, 1H, H-3a), 1.95-1.25 (m, 7H, H-2, 3b, 5, 8, 9), 1.85 (s, 3H, Me), 1.52 (s, 3H, Me), 1.28 (s, 3H, Me);

ESI-LRMS m/z 720 (M+Na$^+$); ESI-HRMS (TFA-Na) calcd. for C$_{40}$H$_{40}$FNNaO$_9$ 720.2585 (M+Na$^+$), found 720.2582 (M+Na$^+$).

Example 25

Preparation of 1,11-O-o-fluorobenzylidene-7-O-p-cyanobenzoyl-1,7,11-trideacetylpyripyropene A (PRD 163)

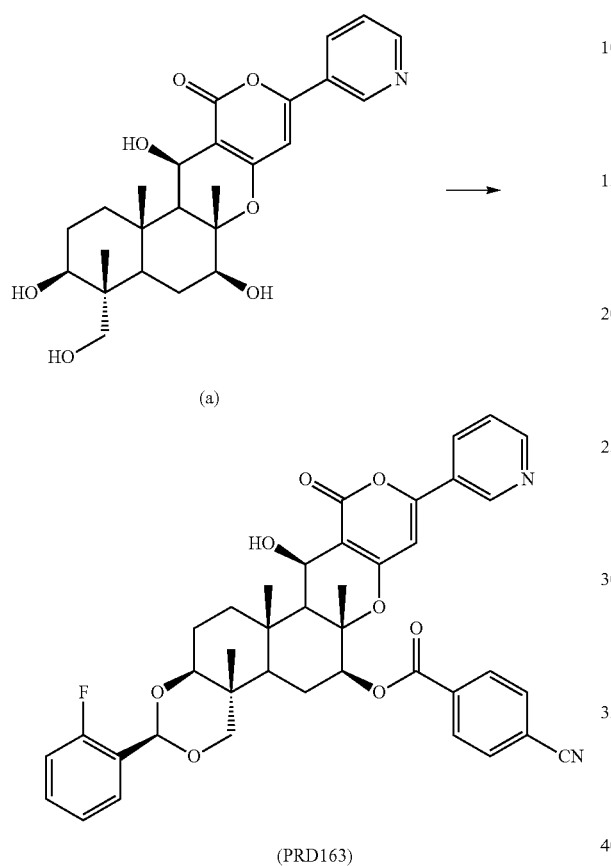

(a)

(PRD163)

In a nitrogen atmosphere, o-fluorobenzaldehyde (85.5 μL, 0.820 mmol) and a catalytic amount of PPTS were added to a solution of a (25.0 mg, 54.5 μmol) in DMF (1.0 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-5%), and the fractions containing the product were concentrated. The resulting residue was dissolved in $CH_2Cl_2$ (0.5 mL), and p-cyanobenzoic acid (2.0 mg, 13.7 μmol), EDCl (3.3 mg, 17.5 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC ($CH_2Cl_2$:MeOH=20:1) to give PRD 163 (7.8 mg, 2 steps, 21%) as a white foam.

$^1$H NMR (CDCl$_3$, 400 MHz) δ 8.97 (dd, 1H, J=0.4, 2.0 Hz), 8.67 (dd, 1H, H-6", J=1.6, 4.8 Hz), 8.22 (d, 2H, H—Ar, J=8.4 Hz), 8.06 (ddd, 1H, H-4", J=1.6, 2.4, 8.0 Hz), 7.81 (d, 2H, H—Ar, J=8.4 Hz), 7.66-7.64 (d, 1H, H—Ar), 7.40-7.37 (m, 1H, H-5"), 7.34-7.32 (m, 1H, H—Ar), 7.26-7.15 (m, 1H, H—Ar), 7.07-7.02 (m, 1H, H—Ar), 6.40 (s, 1H, H-5'), 5.87 (s, 1H, C$\underline{H}$Ar), 5.31 (dd, 1H, H-7, J=5.6, 11.6 Hz), 5.04 (dd, 1H, H-13, J=2.0, 3.6 Hz), 3.90 (d, 1H, H-11a, J=10.4 Hz), 3.59-3.54 (m, 2H, H-11b, 1), 2.97 (br d, 1H, OH-13, J=2.0 Hz), 2.31-2.28 (m, 1H, H-3a), 1.90-1.25 (m, 7H, H-2, 3b, 5, 8, 9), 1.86 (s, 3H, Me), 1.53 (s, 3H, Me), 1.28 (s, 3H, Me);

ESI-LRMS m/z 693 (MH$^+$); ESI-HRMS (TFA-Na) calcd. for $C_{40}H_{38}FN_2O_8$ 693.2612 (MH$^+$), found 693.2607 (MH$^+$).

Example 26

Preparation of 1,11-O-o-fluorobenzylidene-7-O-p-fluorobenzoyl-1,7,11-trideacetylpyripyropene A (PRD 164)

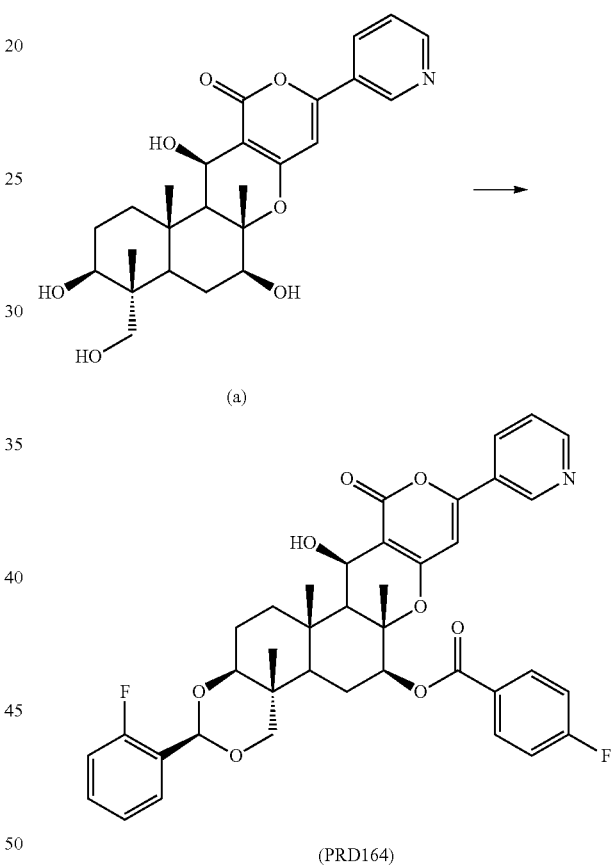

(a)

(PRD164)

In a nitrogen atmosphere, o-fluorobenzaldehyde (85.5 μL, 0.820 mmol) and a catalytic amount of PPTS were added to a solution of a (25.0 mg, 54.5 μmol) in DMF (1.0 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in $CH_2Cl_2$ 0-5%), and the fractions containing the product were concentrated. The resulting residue was dissolved in $CH_2Cl_2$ (0.5 mL), and p-fluorobenzoic acid (2.0 mg, 14.6 μmol), EDCl (3.3 mg, 17.5 mol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 164 (4.9 mg, 2 steps, 13%) as a white foam.

$^1$H NMR (CDCl$_3$, 400 MHz) δ8.97 (dd, 1H, H-2", J=0.8, 2.4 Hz), 8.67 (dd, 1H, H-6", J=1.6, 4.8 Hz), 8.16-8.12 (m, 2H, H—Ar), 8.07 (ddd, 1H, H-4", J=1.6, 2.4, 8.0 Hz), 7.66-7.63 (d, 1H, H—Ar), 7.40-7.32 (m, 2H, H-5", Ar), 7.20-7.07 (m, 3H, H—Ar), 7.07-7.02 (m, 1H, H—Ar), 6.42 (s, 1H, H-5'), 5.87 (s, 1H, CHAr), 5.28 (dd, 1H, H-7, J=4.2, 11.2 Hz), 5.04 (dd, 1H, H-13, J=2.0, 3.6 Hz), 3.90 (d, 1H, H-11a, J=8.1 Hz), 3.59-3.53 (m, 2H, H-11b, 1), 2.93 (br d, 1H, OH-13, J=1.6 Hz), 2.31-2.28 (m, 1H, H-3a), 1.88-1.25 (m, 7H, H-2, 3b, 5, 8, 9), 1.85 (s, 3H, Me), 1.53 (s, 3H, Me), 1.28 (s, 3H, Me);

ESI-LRMS m/z 686 (MH$^+$); ESI-HRMS (TFA-Na) calcd. for C$_{39}$H$_{38}$F$_2$NO$_8$ 686.2565 (MH$^+$), found 686.2544 (MH$^+$).

Example 27

Preparation of 1,11-O-o-naphthylidene-7-O-p-cyanobenzoyl-1,7,11-trideacetylpyripyropene A (PRD 180)

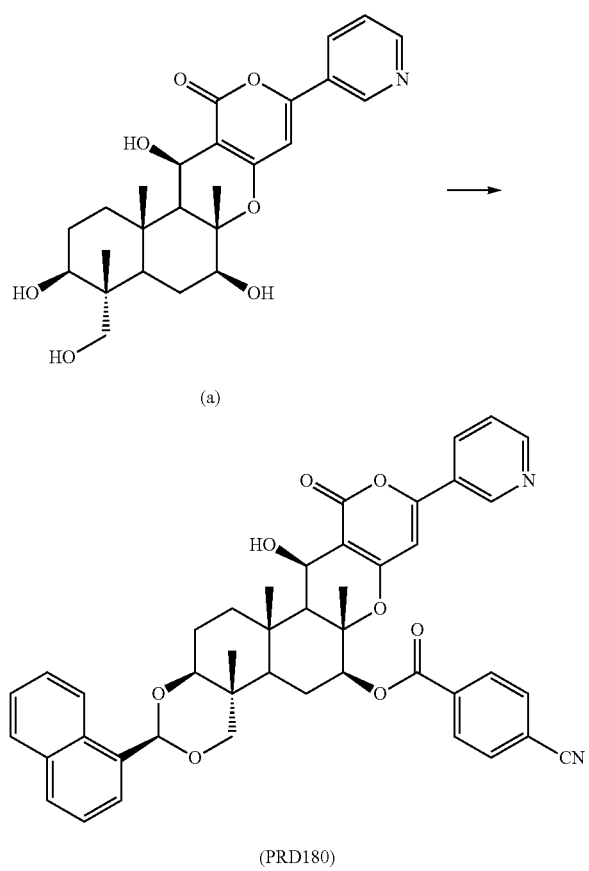

(PRD180)

In a nitrogen atmosphere, 1-(dimethoxymethyl)naphthalene (52.5 μL, 0.260 mmol) and a catalytic amount of PPTS were added to a solution of a (17.7 mg, 38.7 μmol) in DMF (0.5 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-cyanobenzoic acid (5.6 mg, 37.8 μmmol), EDCl (14.5 mg, 75.6 μmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 180 (23.4 mg, 2 steps, 83%) as a white foam.

$^1$H NMR (CDCl$_3$, 400 MHz) δ8.98 (dd, 1H, H-2", J=0.8, 2.4 Hz), 8.67 (dd, 1H, H-6", J=2.0, 4.8 Hz), 8.22 (d, 2H, H—Ar, J=8.8 Hz), 8.15 (d, 1H, H—Ar, J=8.0 Hz), 8.07 (ddd, 1H, H-4", J=1.6, 2.0, 8.0 Hz), 7.86-7.82 (m, 5H, H—Ar), 7.55-7.45 (m, 3H, H—Ar), 7.38 (ddd, 1H, H-5", J=0.8, 4.8, 8.0 Hz), 6.41 (s, 1H, H-5'), 6.19 (s, 1H, CHAr), 5.32 (dd, 1H, H-7, J=6.0, 11.6 Hz), 5.05 (dd, 1H, H-13, J=2.4, 4.0 Hz), 4.00 (d, 1H, H-11a, J=10.4 Hz), 3.71-3.66 (m, 2H, H-11b, 1), 3.04 (br d, 1H, OH-13, J=2.8 Hz), 2.33-2.29 (m, 1H, H-3a), 1.92-1.25 (m, 7H, H-2, 3b, 5, 8, 9), 1.88 (s, 3H, Me), 1.54 (s, 3H, Me), 1.31 (s, 3H, Me);

ESI-LRMS m/z 725 (MH$^+$); ESI-HRMS (TFA-Na) calcd. for C$_{44}$H$_{41}$N$_2$O$_8$ 725.2863 (MH$^+$), found 725.2885 (MH$^+$).

Example 28

Preparation of 1,11-O-o,o-dimethylbenzylidene-7-O-p-cyanobenzoyl-1,7,11-trideacetylpyripyropene A (PRD 181)

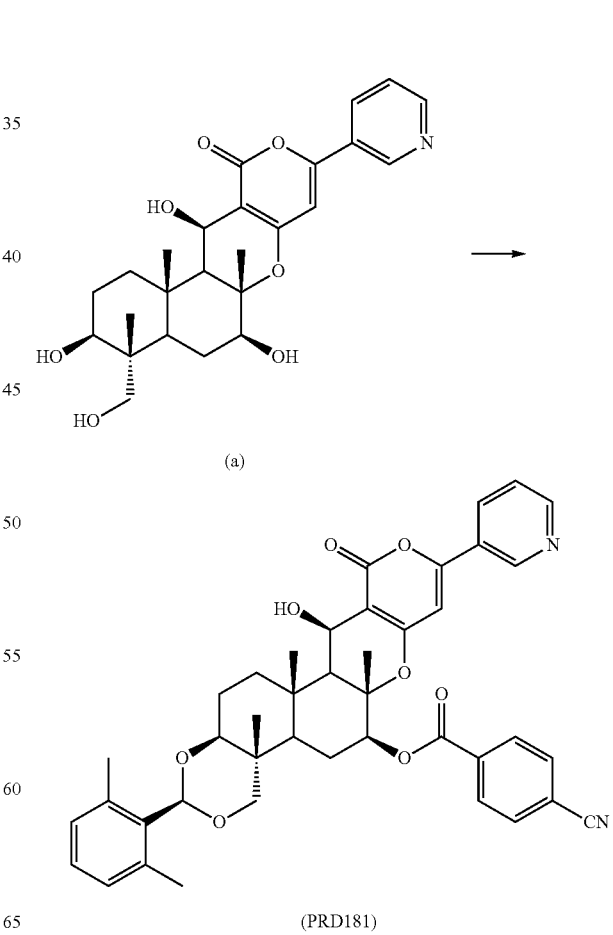

(PRD181)

In a nitrogen atmosphere, o,o-dimethylbenzaldehyde (109 µL, 0.813 mmol) and a catalytic amount of PPTS were added to a solution of a (37.2 mg, 81.3 µmol) in DMF (1.0 mL) and stirred for 24 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 0-5%), and the fractions containing the product were concentrated. The resulting residue was dissolved in CH$_2$Cl$_2$ (0.5 mL), and p-cyanobenzoic acid (5.8 mg, 39.2 µmol), EDCl (15.1 mg, 78.6 µmol), and a catalytic amount of DMAP were added to the solution and stirred for 1 h at room temperature. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by preparative TLC (CH$_2$Cl$_2$:MeOH=20:1) to give PRD 181 (21.4 mg, 2 steps, 38%) as a white foam.

$^1$H NMR (CDCl$_3$, 400 MHz) δ8.97 (dd, 1H, H-2", J=0.8, 2.4 Hz), 8.67 (dd, 1H, H-6", J=1.6, 4.8 Hz), 8.22 (d, 2H, H—Ar. J=8.4 Hz), 8.06 (ddd, 1H, H-4", J=1.6, 2.0, 8.0 Hz), 7.81 (d, 2H, H—Ar, J=8.4 Hz), 7.38 (ddd, 1H, H-5", J=0.8, 4.8, 8.0 Hz), 7.26-7.07 (m, 1H, H—Ar), 6.98 (d, 2H, H—Ar, J=7.2 Hz), 6.41 (s, 1H, H-5'), 5.89 (s, 1H, CHAr), 5.29 (dd, 1H, H-7, J=5.6, 11.6 Hz), 5.05 (dd, 1H, H-13, J=2.0, 4.0 Hz), 3.92 (d, 1H, H-11a, J=10.8 Hz), 3.53-3.49 (m, 2H, H-11b, 1), 3.03 (br d, 1H, OH-13, J=2.0 Hz), 2.52 (s, 6H, ArMe×2), 2.29 (dd, 1H, H-3a, J=3.2, 10.0 Hz), 1.90-1.25 (m, 7H, H-2, 3b, 5, 8, 9), 1.86 (s, 3H, Me), 1.53 (s, 3H, Me), 1.32 (s, 3H, Me);

ESI-LRMS m/z 703 (MH$^+$); ESI-HRMS (TFA-Na) calcd. for C$_{42}$H$_{43}$N$_2$O$_8$ 703.3019 (MH$^+$), found 703.3035 (MH$^+$).

Example 29

Preparation of 7-O-p-cyanobenzoyl-11-deacetoxymethyl-7-deacetyl-11-carboxy-pyripyropene A (PRD 069)

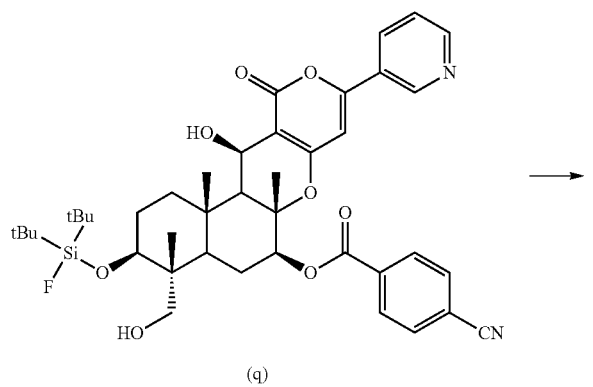

(q)

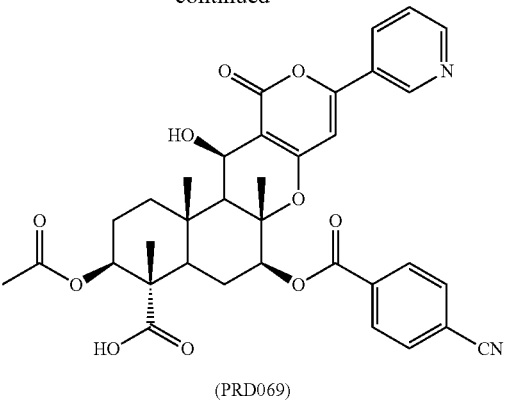

(PRD069)

2.8M Jones reagent (2.66 mL) was added to a solution of q (354 mg, 474 µmol) in aqueous 95% acetone (140 ml) and stirred for 12 h at room temperature. The reaction was terminated by addition of iPrOH to the reaction mixture, which was then filtered through Celite. The filtrate was concentrated and then diluted with EtOAc. The organic layer was washed with water and dried over anhydrous sodium sulfate. The solution was filtered, and the filtrate was concentrated in vacuo. The resulting residue was roughly purified by neutral flash silica gel column chromatography (2×6, MeOH in CH$_2$Cl$_2$ 0-1.5%), and the fractions containing the product were concentrated. The resulting residue was dissolved in MeOH (60 mL), and NaBH$_4$ (54.8 mg, 1.45 mmol) and CeCl$_3$.7H$_2$O (540 mg, 1.45 mmol) were added to the solution and stirred for 30 min at 0° C. The reaction was terminated by addition of acetone to tire reaction mixture, which was then concentrated in vacuo. The resulting residue was roughly purified by neutral flash silica gel column chromatography (2×8, MeOH in CH$_2$Cl$_2$ 0-3%), and the fractions containing the product were concentrated. The resulting residue was dissolved in THF (2.0 mL), and after addition of Et$_3$N.3HF (80.2 µL, 492 µmol), the mixture was stirred for 20 min at room temperature. The reaction mixture was concentrated in vacuo, and the resulting residue was roughly purified by neutral flash silica gel column chromatography (2×5, MeOH in CH$_2$Cl$_2$ 2-5%), and the fractions containing the product were concentrated. The resulting residue was dissolved in CH$_2$Cl$_2$ (3.0 mL), and Ac$_2$O (17.0 µL, 180 µmol, Et$_3$N (27.4 µL, 197 µmol), and a catalytic amount of DMAP were added to the solution and stirred for 4 h at 0° C. MeOH was added to the reaction mixture to terminate the reaction, and EtOAc was then added for dilution. The organic layer was washed with water and dried over anhydrous sodium sulfate. The solution was filtered, and the filtrate was concentrated in vacuo. The resulting residue was purified by neutral flash silica gel column chromatography (2×5, MeOH in CH$_2$Cl$_2$ 0-3%) to give PRD 069 (137 mg, 4 steps, 44%) as a white foam.

$^1$H NMR (CDCl$_3$, 400 MHz) δ8.96 (br s, 1H, H-2"), 8.64 (brs, 1H, H-6"), 8.35 (br d, J=8.0 Hz), 7.71 (d, 2H, H—Ar. J=8.0 Hz), 7.60 (br s, 1H, H-5"), 7.50 (d, 2H, H—Ar. J=8.0 Hz), 7.20 (s, 1H, H-5'), 5.40 (dd, 1H, H-7, J=4.8, 11.6 Hz), 5.17 (dd, 1H, H-1, J=4.4, 12.0 Hz), 5.02 (d, 1H, H-13, J=2.4 Hz), 2.19-1.21 (m, 8H, H-2, 3, 5, 8, 9), 1.96 (s, 3H, Ac), 1.84 (s, 3H-1, Me), 1.44 (s, 3H, Me), 1.18 (s, 3H, Me);

ESI-LRMS m/z 643 (MH+); ESI-HRMS (TFA-Na) calcd. for $C_{35}H_{35}N_2O_{10}$ 643.2292 (MH+), found 643.2285 (MH+).

Example 30

Preparation of 7-O-p-cyanobenzoyl-11-deacetoxymethyl-7-deacetyl-11-methoxy-carbonylpyripyropene A (PRD 070)

ESI-LRMS m/z 679 (M+Na+); ESI-HRMS (TFA-Na) calcd. for $C_{36}H_{36}N_2NaO_{10}$ 679.2268 (M+Na+), found 679.2254 (M+Na+).

Example 31

Preparation of 7-O-p-cyanobenzoyl-11-deacetoxymethyl-7-deacetyl-11-(2,4-dimethoxybenzylamino)carbonylpyripyropene A (PRD 071)

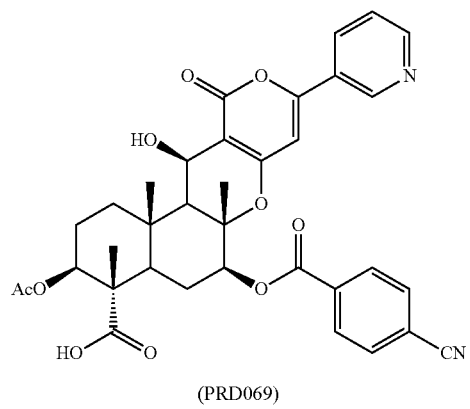

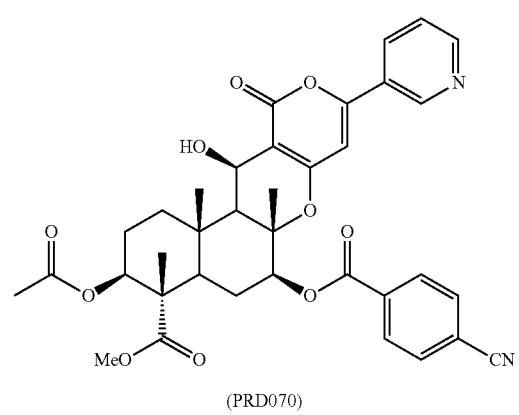

To a solution of PRD 069 (22.3 mg, 34.7 μmol) in MeOH/benzene (1:2, 0.6 mL) was added (trimethylsilyl)diazomethane (2.0M hexane solution, 52.0 μL, 0.104 mmol) and stirred for 5 min at room temperature. The reaction was terminated by addition of AcOH to the reaction mixture, which was then concentrated. The resulting residue was purified by preparative TLC (CH$_2$Cl$_2$:MeOH=15:1) to give PRD 070 (12.5 mg, 55%) as a white foam.

$^1$H NMR (CDCl$_3$, 300 MHz) δ8.96 (dd, 1H, H-2", J=0.9, 2.4 Hz), 8.67 (dd, 1H, H-6", J=1.5, 4.8 Hz), 8.19 (d, 2H, H—Ar. J=9.0 Hz), 8.07 (ddd, 1H, H-4", J=1.5, 2.1, 8.1 Hz), 7.79 (d, 2H, H—Ar, J=9.0 Hz), 7.38 (ddd, 1H, H-5", J=1.5, 4.8, 8.1 Hz), 6.40 (s, 1H, H-5'), 5.29 (dd, 1H, H-7, J=5.7, 12.0 Hz), 5.23 (dd, 1H, H-1, J=4.8, 11.7 Hz), 5.04 (d, 1H, H-13, J=3.3 Hz), 3.72 (s, 3H-1, CO$_2$Me), 2.98 (br s, 1H, OH-13), 2.13-1.59 (m, 8H, H-2, 3, 5, 8, 9), 2.01 (s, 3H, Ac), 1.83 (s, 3H, Me), 1.48 (s, 3H, Me), 1.25 (s, 3H, Me);

To a solution of PRD 069 (16.0 mg, 21.0 μmol) in DMF (0.5 mL), 2,4-dimethoxybenzylamine (16.0 μL, 105 μmol), BOP (40.0 mg, 105 μmol), and a catalytic amount of DMAP were added and stirred for 1 h at room temperature. MeOH was added to the reaction mixture to terminate the reaction, and EtOAc was then added for dilution. The organic layer was washed with 1N HCl and water and dried over anhydrous sodium sulfate. The solution was filtered, and the filtrate was concentrated in vacuo. The resulting residue was purified by neutral flash silica gel column chromatography (1×3, MeOH in CH$_2$Cl$_2$ 1-2%) to give PRD 071 (16.3 mg, 85%) as a white foam.

$^1$H NMR (CDCl$_3$, 300 MHz) δ8.96 (d, 1H, H-2", J=1.5 Hz), 8.66 (dd, 1H, H-6", J=1.5, 5.1 Hz), 8.19 (d, 2H, H—Ar. J=8.4 Hz), 8.09-8.04 (m, 1H, H-4"), 7.80 (d, 2H, H—Ar, J=8.4 Hz), 7.37 (dd, 1H, H-5", J=4.8, 8.1 Hz), 6.39-6.28 (m, 5H, H—Ar, 5', NH), 5.34 (dd, 1H, H-7, J=6.6, 11.7 Hz), 5.17-5.20 (m, 1H, H-1), 5.01 (d, 1H, H-13, J=3.9 Hz), 4.39-4.33 (m, 2H, benzyl), 3.80 (s, 3H, Ar—OMe), 3.71 (s, 3H, Ar—OMe), 3.00 (br s, 1H, H-13), 2.20-1.50 (m, 8H, H-2, 3, 5, 8, 9), 1.78 (s, 3H, Ac), 1.77 (s, 3H, Me), 1.47 (s, 3H, Me), 1.24 (s, 3H, Me);

ESI-LRMS m/z 814 (M+Na$^+$); ESI-HRMS (TFA-Na) calcd. for $C_{44}H_{45}N_3NaO_{11}$ 814.2972 (M+Na$^+$), found 814.2954 (M+Na$^+$).

Example 32

Preparation of 1,11-O-benzylidene-1,7,11-trideacetyl-7-O-(1-methoxy-1-p-methoxyphenyl)methylpyripyropene A (PRD 073)

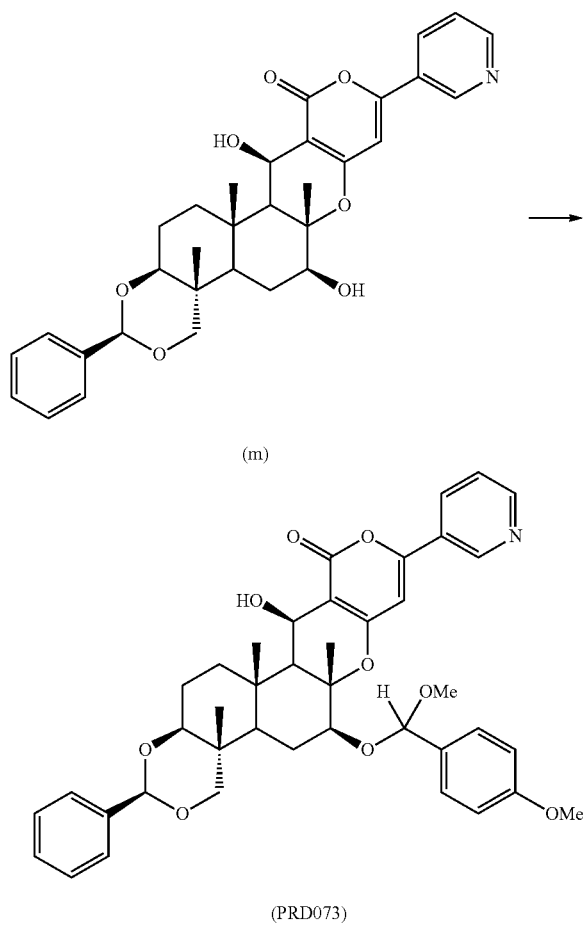

In a nitrogen atmosphere, p-anisaldehyde dimethyl acetal (0.5 mL) and a catalytic amount of PPTS were added to a solution of m (15.0 mg, 27.5 μmol) in DMF (1.0 mL) and stirred for 12 h at room temperature. The reaction mixture was diluted with EtOAc, and the organic layer was washed with water and dried over anhydrous sodium sulfate. The solution was filtered, and the filtrate was concentrated in vacuo. The resulting residue was purified by neutral flash silica gel column chromatography (1×5, MeOH in $CH_2Cl_2$ 1.5%) to give PRD 073 (17.8 mg, quantitative) as a white foam.

ESI-LRMS m/z 718 (M+Na$^+$); ESI-HRMS (TFA-Na) calcd. for $C_{41}H_{45}NaNO_9$ 718.2992 (M+Na$^+$), found 718.3001 (M+Na$^+$).

Test 1

Analysis of Stability Against Metabolizing Enzymes in the Liver

A test of stability of pyripyropene derivatives against metabolizing enzymes in the liver was carried out by the method of Ishigami et al. (Drug Meta. Dispos., Vol. 30, pp. 904-910, 2002). The enzyme source which was used was a hepatic microsome prepared from female SD rats (XenoTech). To a 100 mM sodium phosphate buffer (pH 7.4), 180 pmol (P450)/mL, of hepatic microsome, 1 mM ethylene diamine tetraacetate (Wako), glucose hexaphosphate (SIGMA), 1 mM nicotinamide adenine dinucleotide phosphate (SIGMA), 1.5 units of glucose hexaphosphate dehydrogenase (SIGMA), and the particular pyripyropene derivative to be tested (6 μg/mL) were added so as to give a total volume of 200 μL, and the mixture was allowed to react for 30, 120, 360, or 540 min at 37° C.

Subsequently, 500 μL of ethyl acetate were added to terminate the reaction, and 300 μL of distilled water were added and thoroughly stirred. The mixture was centrifuged to separate into an aqueous layer and an ethyl acetate layer, and a 300 μL aliquot of the ethyl acetate layer was collected into a 1.5 mL tube (Eppendorf, Catalog No. 3810). The collected liquid was evaporated to dryness by a centrifugal evaporator (Tokyo Rikakikai Co., Ltd.) and redissolved in 150 μL of methanol. A 5 μL portion of the resulting solution was used for analysis.

The analysis was conducted using a ultra high performance liquid chromatography (system: Shimadzu Prominence, column: Shim Pack XR-ODS, 2.0 φ×75 mm, 40° C., Shimadzu Corporation). Elution was carried out with a linear concentration gradient starting with an aqueous 0.1% phosphoric acid solution containing 5% acetonitrile and terminating after 6 min with an aqueous 0.1% phosphoric acid solution containing 95% acetonitrile while detection was conducted at a wavelength of 320 nm.

The peak area of each pyripyropene derivative was calculated using analytic software (LCMS solution, Shimadzu Corporation), and the amount of the pyripyropene derivative remaining after each reaction period was calculated taking the peak area of the pyripyropene derivative immediately before the commencement of reaction as 100%.

The time elapsed until the remaining amount reached 50% (half-life) was calculated and is shown in Table 1.

TABLE 1

| Name of compound | Half-life |
| --- | --- |
| PRD069 | >9 h |
| PRD070 | >9 h |
| PRD071 | >9 h |
| PRD073 | >9 h |
| PRD074 | >9 h |
| PRD079 | >9 h |
| PRD080 | >9 h |
| PRD081 | >9 h |
| PRD119 | >9 h |
| PRD121 | >9 h |
| PRD122 | >9 h |
| PRD123 | >9 h |
| PRD125 | >9 h |
| PRD126 | >9 h |
| PRD143 | >9 h |
| PRD155 | >9 h |
| PRD156 | >9 h |
| PRD157 | >9 h |

TABLE 1-continued

| Name of compound | Half-life |
|---|---|
| PRD158 | >9 h |
| PRD159 | >9 h |
| PRD160 | >9 h |
| PRD161 | >9 h |
| PRD162 | >9 h |
| PRD163 | >9 h |
| PRD164 | >9 h |
| PRD166 | >9 h |
| PRD167 | >9 h |
| PRD177 | >9 h |
| PRD180 | >9 h |
| PRD181 | >9 h |
| PRD186 | >9 h |
| PRD187 | >9 h |
| PPA | <1 h |
| PRD007 | <1 h |
| PRD009 | <1 h |
| PRD021 | <1 h |
| PRD024 | <1 h |
| PRD025 | <1 h |
| PRD026 | <1 h |
| PRD043 | >9 h |
| PRD056 | >9 h |

As shown in Table 1, while the half-lives of known compounds PPA, PRD 007, PRD 009, PRD 021, PRD 024, PRD 025, and PRD 026 were each 1 h, known compounds PRD 043 and PRD 056 as well as novel compounds PRD 069, PRD 071, PRD 073, PRD 074, PRD 079, PRD 081, PRD 119, PRD 121, PRD 122, PRD 123, PRD 125, PRD 126, PRD 143, PRD 155, PRD 156, PRD 157, PRD 158, PRD 159, PRD 160, PRD 161, PRD 162, PRD 163, PRD 164, PRD 166, PRD 167, PRD 177, PRD 180, PRD 181, PRD 186, and PRD 187 exhibited a very high stability as demonstrated by their half-lives of at least 9 h.

Among the known compounds used for comparison, PPA is pyripyropene A, and the remaining PRD 007, PRD 009, PRD 021, PRD 024, PRD 025, PRD 026, PRD 043, and PRD 056 are the compounds having the following formulas.

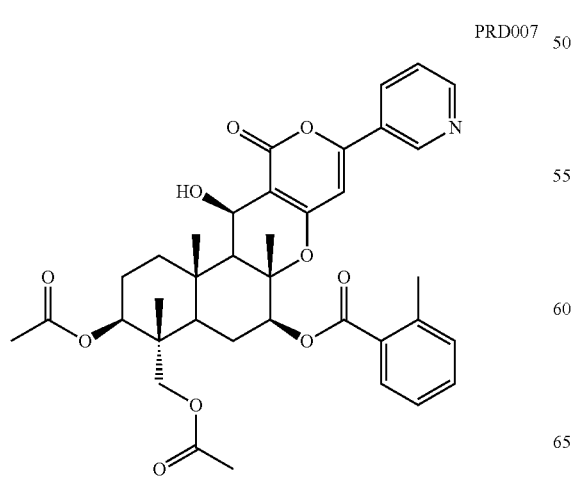

PRD007

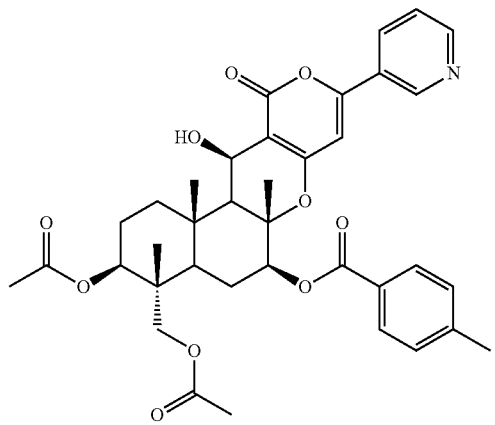

PRD009

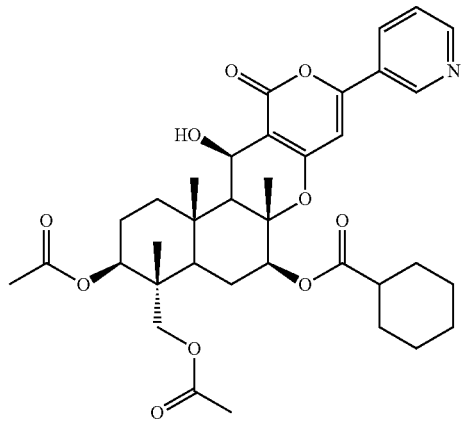

PRD021

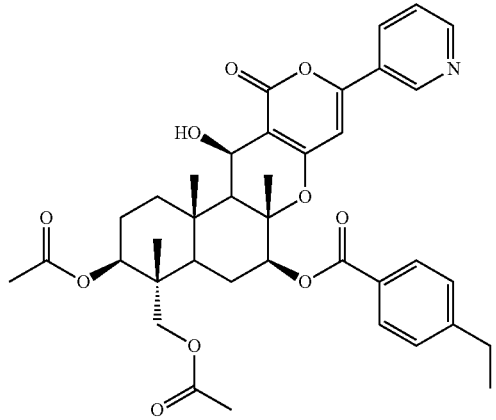

PRD024

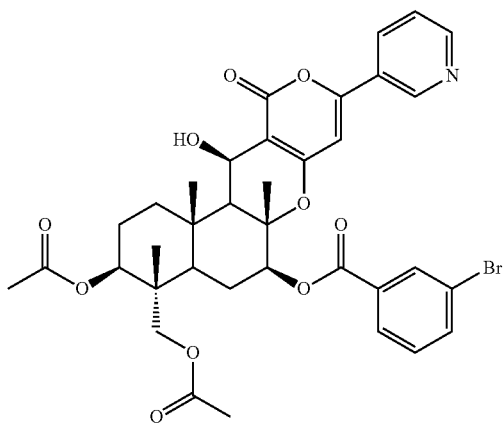
PRD025

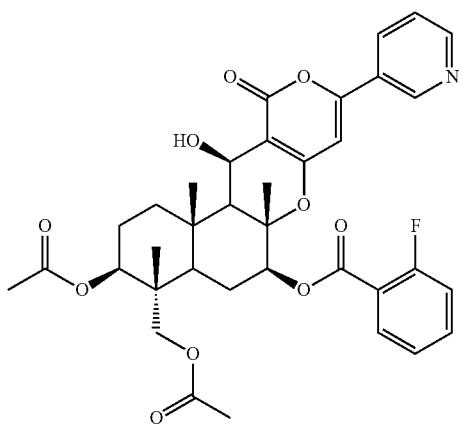
PRD026

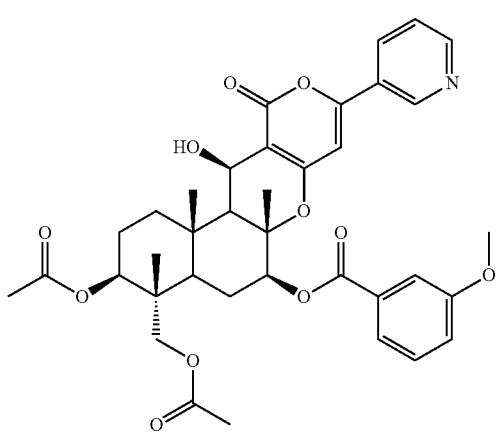
PRD043

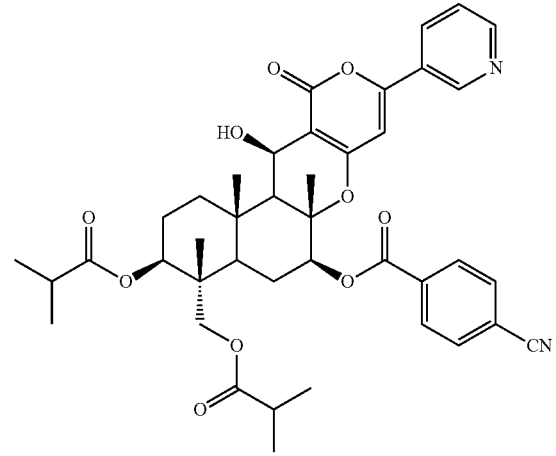
PRD056

Test 2
Measurement of ACAT2-Inhibiting Activity
[Preparation of Enzyme Source of ACAT2]

An enzyme source was prepared according to the method of Uelmen et al. (J. Biol. Chem., Vol. 270, pp. 26192-26201, 1995) which was partly modified. The enzyme source which was used was a membrane fraction derived from murine hepatic microsome. Mouse livers were homogenized in buffer solution A (50 mM Tris HCl solution (pH 7.8), 1 mM ethylene diamine tetraacetate, and 1 mM phenylmethanesulfonyl fluoride) using a Potter-type homogenizer (Tokyo-Riko). The homogenate was centrifuged at 12000×g, and the supernatant was subjected to ultracentrifugation at 100000× g. The resulting sediment was collected as a microsome fraction, and this fraction was adjusted so as to have a protein concentration of 5 mg/mL using buffer solution A.

[Measurement of ACAT-Inhibiting Activity]

Measurement of the ACAT-inhibiting activity of the pyripyropene derivative prepared in each example was carried out in accordance with the method of Field et al. (Gastroenterology, Vol. 83, pp. 873-880, 1982). The above-described enzyme source (200 µg as protein), 200 mM bovine serum albumin, [1-$^{14}$C]oleoyl coenzyme A (final concentration 170 µM, 0.090 µCi), and the particular pyripyropene derivative to be tested (10 µL of a methanol solution with a concentration of 1, 0.1, 0.01, 0.001, 0.0001, or 0.00001 mg/mL) were added to buffer solution A so as to give a total volume of 200 µL, and the mixture was allowed to react for 5 min at 37° C. As a control, 10 µL of methanol were used in place of the pyripyropene derivative.

Subsequently, the reaction was terminated by adding 1.2 mL of chloroform/methanol (1:2), and the lipid was collected by the method of Bligh & Dyer (Can. J. Biochem. Physiol., Vol. 37, pp. 911-917, 1959). The chloroform layer was evaporated to dryness and was used to spot a thin layer chromatography plate (silica gel plate, Merck, 0.5 mm thickness). Elution for separation was carried out using hexane/diethyl ether/acetic acid (70:30:1, v/v) as an eluant. The amount of [$^{14}$C] cholesteryl oleate which was formed was determined by a BAS 2000 bio-image analyzer (Fuji Film), and the inhibitory activity of the test compound was calculated according to the following equation by comparison with the result in the control:

% Inhibition=100−[(radioactivity when the test compound was added)−(background)]/[(radioactivity in the control)−(background)]

wherein the background is the radioactivity of a thin layer chromatography plate which was not spotted.

The concentration at which 50% inhibition of the enzyme activity was achieved ($IC_{50}$) was calculated. In addition, the specific activity relative to PRD 043, which is a known compound having an ACAT2-inhibiting activity (Tomoda et al., Pyripiropene Derivatives having ACAT2-Inhibiting Activities, WO 2009/081957), was calculated by the following equation:

Specific activity=($IC_{50}$ of the test compound)/($IC_{50}$ of PRD 043).

The results of inhibitory activity and specific activity are shown in Table 2. The meanings of the symbols used in the table are as follows:

Inhibitory activity: Concentration required for 50% inhibition of ACAT 2

(=$IC_{50}$)

\*\*\*: inhibitory activity<0.5 nM

\*\*: 0.5 nM≤inhibitory activity<1.0 nM

\*: 1.0 nM≤inhibitory activity<10.0 nM

Specific activity: (($IC_{50}$ of the test compound)/($IC_{50}$ of PRD 043)

++++: 20<specific activity

+++: 10<specific activity≤20

++: 5<specific activity≤10

+: 1<specific activity≤5

−: 0.1≤specific activity<1

−−: 0.01≤specific activity<0.1

TABLE 2

| Name of compound | Inhibitory activity | Specific activity |
|---|---|---|
| PRD069 | *** | ++++ |
| PRD070 | ** | +++ |
| PRD071 | *** | ++++ |
| PRD073 | ** | +++ |
| PRD074 | ** | +++ |
| PRD079 | ** | +++ |
| PRD080 | ** | +++ |
| PRD081 | * | +++ |
| PRD119 | ** | ++++ |
| PRD121 | ** | +++ |
| PRD122 | ** | +++ |
| PRD123 | *** | ++++ |
| PRD125 | ** | +++ |
| PRD126 | ** | +++ |
| PRD143 | ** | +++ |
| PRD155 | ** | +++ |
| PRD156 | *** | ++++ |
| PRD157 | *** | ++++ |
| PRD158 | * | +++ |
| PRD159 | ** | +++ |
| PRD160 | ** | +++ |
| PRD161 | ** | +++ |
| PRD162 | * | +++ |
| PRD163 | ** | +++ |
| PRD164 | ** | +++ |
| PRD166 | ** | +++ |
| PRD167 | ** | +++ |
| PRD177 | * | +++ |
| PRD180 | * | +++ |
| PRD181 | ** | +++ |
| PRD186 | * | +++ |
| PRD187 | ** | +++ |
| PPA | (*) | −− |
| PRD043 | (*) | 1 |
| PRD056 | (*) | − |

Compared to the known compounds PPA and PRD 043 and PRD 056 both having a half-life of 9 h or longer which are shown as comparative examples, the compounds according to the present invention exhibit an extremely high inhibitory activity against ACAT 2.

Thus, compared to known compounds, a novel compound according to the present invention not only exhibits a higher inhibitory activity against ACAT2 but has a longer half-life against metabolism by hepatic enzymes, or it is less metabolizable in the liver, so its high inhibitory activity lasts longer. Accordingly, a novel compound according to the present invention is expected to be useful as a specific ACAT2 inhibitor of high activity and prolonged action in the treatment of arteriosclerosis.

A method for testing the ACAT2-inhibiting activity is not limited to the above-described method. For example, a microsome prepared by the small intestine or liver of an animal such as a rat or monkey may be used as a source of ACAT2 enzyme. Alternatively, cultured cells (such as Caco-2 intestinal cells, primarily cultured hepatic cells, or HepG2 hepatic cells) or a microsome prepared from cultured cells having highly expressed ACAT2 can be used as a source of ACAT2 enzyme.

The invention claimed is:

1. A compound having the following formula (III) or a pharmaceutically acceptable salt, solvate, or hydrate thereof:

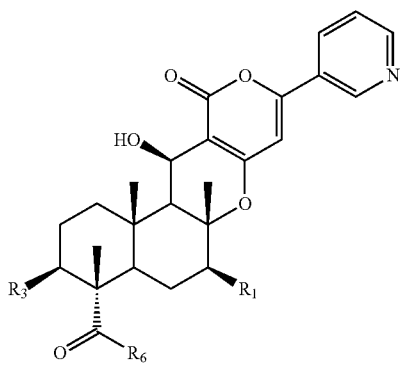

(III)

wherein $R_6$ is a hydroxyl group (OH), a lower alkoxy group benzylamino or an arylmethylamino group which may be substituted on the aromatic ring, and $R_1$ and $R_3$ may be the same or different and each represent a group selected from a lower alkylcarbonyloxy, a substituted or unsubstituted arylcarbonyloxy, and a cycloalkylcarbonyloxy.

2. An ACAT2 inhibitor comprising as an active ingredient the compound as set forth in claim 1 or a pharmaceutically acceptable salt, solvate, or hydrate thereof.

3. A pharmaceutical composition for ACAT2 inhibition comprising the compound as set forth in claim 1 or a pharmaceutically acceptable salt, solvate, or hydrate thereof in an effective amount for inhibition of ACAT2 and a pharmaceutically acceptable carrier.

4. A compound having the following structure (PRD125) or a pharmaceutically acceptable salt, solvate, or hydrate thereof:

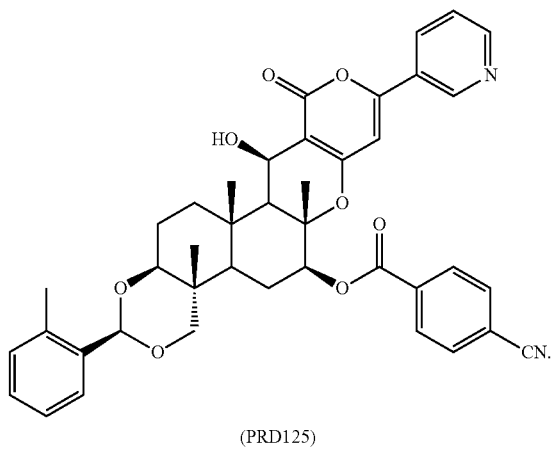

(PRD125)

5. An ACAT2 inhibitor comprising as an active ingredient the compound as set forth in claim 4 or a pharmaceutically acceptable salt, solvate, or hydrate thereof.

6. A pharmaceutical composition for ACAT2 inhibition comprising the compound as set forth in claim 4 or a pharmaceutically acceptable salt, solvate, or hydrate thereof in an effective amount for inhibition of ACAT2 and a pharmaceutically acceptable carrier.

7. (2R,4aR,6S,6aS,12R,12bS,14aS)-12-hydroxy-4a,6a,12b-trimethyl-11-oxo-9-(pyridin-3-yl)-2-(o-tolyl)-4a,4b,5,6,6a,11,12,12a,12b,13,14,14a-dodecahydro-4H-[1,3]dioxino[5',4':3,4]benzo[1,2-f]pyrano[4,3-b]chromen-6-yl 4-cyanobenzoate.

8. An ACAT2 inhibitor comprising as an active ingredient the compound as set forth in claim 7 or a pharmaceutically acceptable salt, solvate, or hydrate thereof.

9. A pharmaceutical composition for ACAT2 inhibition comprising the compound as set forth in claim 7 or a pharmaceutically acceptable salt, solvate, or hydrate thereof in an effective amount for inhibition of ACAT2 and a pharmaceutically acceptable carrier.

* * * * *

UNITED STATES PATENT AND TRADEMARK OFFICE
CERTIFICATE OF CORRECTION

PATENT NO.        : 9,187,492 B2  
APPLICATION NO.   : 13/638332  
DATED             : November 17, 2015  
INVENTOR(S)       : Hiroshi Tomoda et al.

Page 1 of 1

It is certified that error appears in the above-identified patent and that said Letters Patent is hereby corrected as shown below:

IN THE CLAIMS

Column 64, Approx. Line 48, Claim 1, after the words "a lower alkoxy group" insert -- , --

Signed and Sealed this  
Twenty-ninth Day of March, 2016

Michelle K. Lee  
*Director of the United States Patent and Trademark Office*